(12) United States Patent
Zhang et al.

(10) Patent No.: US 9,333,179 B2
(45) Date of Patent: May 10, 2016

(54) AMPHIPHILIC COMPOUND ASSISTED NANOPARTICLES FOR TARGETED DELIVERY

(75) Inventors: Liangfang Zhang, San Diego, CA (US); Aleksandar F. Radovic-Moreno, Cambridge, MA (US); Frank X. Gu, Waterloo (CA); Frank Alexis, Greenville, SC (US); Robert S. Langer, Newton, MA (US); Omid C. Farokhzad, Chestnut Hill, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 271 days.

(21) Appl. No.: 12/573,591

(22) Filed: Oct. 5, 2009

(65) Prior Publication Data
US 2010/0203142 A1 Aug. 12, 2010

Related U.S. Application Data

(63) Continuation of application No. PCT/US2008/059480, filed on Apr. 4, 2008.

(60) Provisional application No. 60/986,202, filed on Nov. 7, 2007, provisional application No. 60/910,097, filed on Apr. 4, 2007, provisional application No. 60/938,590, filed on May 17, 2007, provisional application No. 60/985,104, filed on Nov. 2, 2007, provisional application No. 60/990,250, filed on Nov. 26, 2007.

(51) Int. Cl.
*A61K 9/51* (2006.01)
*A61K 47/48* (2006.01)
*B82Y 5/00* (2011.01)

(52) U.S. Cl.
CPC ............. *A61K 9/5123* (2013.01); *A61K 9/5153* (2013.01); *A61K 9/5192* (2013.01); *A61K 47/48238* (2013.01); *A61K 47/48907* (2013.01); *A61K 47/48915* (2013.01); *B82Y 5/00* (2013.01)

(58) Field of Classification Search
None
See application file for complete search history.

(56) References Cited

U.S. PATENT DOCUMENTS

| | | |
|---|---|---|
| 3,766,774 A | 10/1973 | Clark |
| 4,270,537 A | 6/1981 | Romaine |
| 4,446,122 A | 5/1984 | Chu et al. |
| 4,596,556 A | 6/1986 | Morrow et al. |
| 4,631,211 A | 12/1986 | Houghten |
| 4,638,045 A | 1/1987 | Kohn et al. |
| 4,790,824 A | 12/1988 | Morrow et al. |
| 4,795,436 A | 1/1989 | Robinson |
| 4,806,621 A | 2/1989 | Kohn et al. |
| 4,818,542 A | 4/1989 | DeLuca |
| 4,839,416 A | 6/1989 | Orenstein |
| 4,862,851 A | 9/1989 | Washino et al. |
| 4,886,499 A | 12/1989 | Cirelli et al. |
| 4,902,615 A | 2/1990 | Freeman et al. |
| 4,904,479 A | 2/1990 | Illum |
| 4,940,460 A | 7/1990 | Casey et al. |
| 4,941,880 A | 7/1990 | Burns |
| 4,946,929 A | 8/1990 | D'Amore et al. |
| 4,959,219 A | 9/1990 | Chow |
| RE33,405 E | 10/1990 | Chu et al. |
| 4,970,299 A | 11/1990 | Bazinet et al. |
| 4,976,968 A | 12/1990 | Steiner |
| 5,010,167 A | 4/1991 | Ron et al. |
| 5,015,235 A | 5/1991 | Crossman |
| 5,019,379 A | 5/1991 | Domb et al. |
| 5,055,404 A | 10/1991 | Ueda et al. |
| 5,064,413 A | 11/1991 | McKinnon et al. |
| 5,069,936 A | 12/1991 | Yen |
| 5,093,246 A | 3/1992 | Cech et al. |
| 5,118,528 A * | 6/1992 | Fessi et al. ............... 427/213.36 |
| 5,141,496 A | 8/1992 | Dalto et al. |
| 5,162,504 A | 11/1992 | Horoszewicz |
| 5,174,930 A * | 12/1992 | Stainmesse et al. ........... 264/4.6 |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |

(Continued)

FOREIGN PATENT DOCUMENTS

| | | |
|---|---|---|
| CA | 2453959 | 1/2003 |
| CA | 2649149 | 10/2007 |

(Continued)

OTHER PUBLICATIONS

Scholfield, C. R. "Composition of soybean lecithin." Journal of the American Oil Chemists Society 58.10 (1981): 889-892.*

(Continued)

*Primary Examiner* — David J Blanchard
*Assistant Examiner* — Peter Anthopolos
(74) *Attorney, Agent, or Firm* — Pabst Patent Group LLP

(57) ABSTRACT

The present invention generally relates to nanoparticles with an amphiphilic component. One aspect of the invention is directed to a method of developing nanoparticles with desired properties. In one set of embodiments, the method includes producing libraries of nanoparticles having highly controlled properties, which can be formed by mixing together two or more macromolecules in different ratios. One or more of the macromolecules may be a polymeric conjugate of a moiety to a biocompatible polymer. In some cases, the nanoparticle may contain a drug. Other aspects of the invention are directed to methods using nanoparticle libraries.

19 Claims, 15 Drawing Sheets

(56) References Cited

U.S. PATENT DOCUMENTS

| | | |
|---|---|---|
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz |
| 5,417,662 A | 5/1995 | Hjertman et al. |
| 5,449,513 A | 9/1995 | Yokoyama |
| 5,466,220 A | 11/1995 | Brenneman |
| 5,472,704 A | 12/1995 | Santus et al. |
| 5,480,381 A | 1/1996 | Weston |
| 5,500,161 A | 3/1996 | Andrianov et al. |
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A | 11/1996 | Domb et al. |
| 5,595,877 A | 1/1997 | Gold et al. |
| 5,599,302 A | 2/1997 | Lilley et al. |
| 5,622,699 A | 4/1997 | Ruoslahti |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A | 2/1999 | Yah et al. |
| 5,871,747 A | 2/1999 | Gengoux-Sedlik |
| 5,874,218 A | 2/1999 | Drolet et al. |
| 5,876,727 A | 3/1999 | Swain |
| 5,879,712 A | 3/1999 | Bomberger |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,060,306 A | 5/2000 | Flatt |
| 6,083,505 A | 7/2000 | Miller |
| 6,095,148 A | 8/2000 | Shastri et al. |
| 6,107,094 A | 8/2000 | Crooke |
| 6,110,462 A | 8/2000 | Barbas et al. |
| 6,120,666 A | 9/2000 | Jacobson |
| 6,123,727 A | 9/2000 | Vacanti et al. |
| 6,127,533 A | 10/2000 | Cook et al. |
| 6,139,870 A | 10/2000 | Verrecchia |
| 6,184,364 B1 | 2/2001 | Pieken et al. |
| 6,190,913 B1 | 2/2001 | Singh |
| 6,197,346 B1 | 3/2001 | Mathiowitz |
| 6,225,460 B1 | 5/2001 | Bischofberger et al. |
| 6,232,082 B1 | 5/2001 | Ennifar |
| 6,235,313 B1 | 5/2001 | Mathiowitz |
| 6,238,705 B1 | 5/2001 | Liu et al. |
| 6,242,246 B1 | 6/2001 | Gold et al. |
| 6,245,776 B1 | 6/2001 | Skwierczynski |
| 6,254,890 B1 | 7/2001 | Hirosue et al. |
| 6,265,608 B1 | 7/2001 | SumnerJr |
| 6,288,040 B1 | 9/2001 | Muller |
| 6,291,673 B1 | 9/2001 | Fuchs |
| 6,344,318 B1 | 2/2002 | Gold et al. |
| 6,348,462 B1 | 2/2002 | Gerster |
| 6,365,187 B2 | 4/2002 | Mathiowitz et al. |
| 6,376,190 B1 | 4/2002 | Gold et al. |
| 6,395,718 B1 | 5/2002 | Slusher |
| 6,399,754 B1 | 6/2002 | Cook |
| 6,403,779 B1 | 6/2002 | Kawasaki et al. |
| 6,429,200 B1 | 8/2002 | Monahan et al. |
| 6,444,782 B1 | 9/2002 | Hamlin |
| 6,451,527 B1 | 9/2002 | Larocca et al. |
| 6,458,539 B1 | 10/2002 | Gold et al. |
| 6,458,543 B1 | 10/2002 | Gold et al. |
| 6,482,594 B2 | 11/2002 | Gold et al. |
| 6,492,554 B2 | 12/2002 | Dalton et al. |
| 6,506,559 B1 | 1/2003 | Fire et al. |
| 6,506,577 B1 | 1/2003 | Deming et al. |
| 6,528,499 B1 | 3/2003 | Kozikowski |
| 6,558,951 B1 | 5/2003 | Tomai |
| 6,569,896 B2 | 5/2003 | Dalton et al. |
| 6,589,562 B1 | 7/2003 | Shefer et al. |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming et al. |
| 6,656,469 B1 | 12/2003 | Svensson |
| 6,686,446 B2 | 2/2004 | Deming et al. |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold et al. |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming et al. |
| 6,838,484 B2 | 1/2005 | Steiner et al. |
| 6,875,605 B2 | 4/2005 | Ma |
| 6,875,886 B2 | 4/2005 | Frangioni |
| 6,902,743 B1 | 6/2005 | Setterstrom |
| 6,932,971 B2 | 8/2005 | Bachmann et al. |
| 6,984,393 B2 | 1/2006 | Amsden |
| 6,995,284 B2 | 2/2006 | Dalton et al. |
| 6,998,500 B2 | 2/2006 | Dalton et al. |
| 7,008,411 B1 | 3/2006 | Mandrusov et al. |
| 7,022,870 B2 | 4/2006 | Dalton et al. |
| 7,026,500 B2 | 4/2006 | Dalton et al. |
| 7,029,859 B2 | 4/2006 | Thompson |
| 7,030,228 B1 | 4/2006 | Schmitz |
| 7,056,704 B2 | 6/2006 | Tuschl et al. |
| 7,078,196 B2 | 7/2006 | Tuschl et al. |
| 7,097,837 B2 | 8/2006 | Nielsen |
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |

(56) References Cited

U.S. PATENT DOCUMENTS

| | | |
|---|---|---|
| 7,422,902 B1 | 9/2008 | Wheeler |
| 7,427,629 B2 | 9/2008 | Kedl |
| 7,488,792 B2 | 2/2009 | Ruoslahti |
| 7,550,441 B2 | 6/2009 | Farokhzad et al. |
| 7,727,969 B2 | 6/2010 | Farokhzad |
| 7,762,803 B2 | 7/2010 | Nakazato |
| 7,767,803 B2 | 8/2010 | Diener |
| 8,277,812 B2 | 10/2012 | Iannacone |
| 8,323,698 B2 | 12/2012 | Gu |
| 8,343,497 B2 | 1/2013 | Shi |
| 8,343,498 B2 | 1/2013 | Alexis |
| 8,562,998 B2 | 10/2013 | Shi |
| 8,574,564 B2 | 11/2013 | Renner |
| 8,637,028 B2 | 1/2014 | Alexis |
| 2001/0012890 A1 | 8/2001 | Thompson |
| 2002/0009466 A1 | 1/2002 | Brayden |
| 2002/0064780 A1 | 5/2002 | Gold et al. |
| 2002/0068091 A1 | 6/2002 | Davis et al. |
| 2002/0086356 A1 | 7/2002 | Tuschl et al. |
| 2002/0099036 A1 | 7/2002 | Dalton et al. |
| 2002/0099096 A1 | 7/2002 | Dalton et al. |
| 2002/0102613 A1 | 8/2002 | Hoogenboom |
| 2002/0106647 A1 | 8/2002 | Segal |
| 2002/0116054 A1 | 8/2002 | Lundell |
| 2002/0119473 A1 | 8/2002 | Lupold |
| 2002/0119916 A1 | 8/2002 | Hassan |
| 2002/0150578 A1 | 10/2002 | He et al. |
| 2002/0151004 A1 | 10/2002 | Craig |
| 2002/0153251 A1 | 10/2002 | Sassi et al. |
| 2002/0156125 A1 | 10/2002 | Broder et al. |
| 2002/0173495 A1 | 11/2002 | Dalton et al. |
| 2003/0003103 A1 | 1/2003 | Thompson |
| 2003/0003114 A1 | 1/2003 | Pan |
| 2003/0009029 A1 | 1/2003 | Buchholz et al. |
| 2003/0022868 A1 | 1/2003 | Dalton et al. |
| 2003/0035804 A1 | 2/2003 | D'Amico et al. |
| 2003/0054360 A1 | 3/2003 | Gold et al. |
| 2003/0087301 A1 | 5/2003 | Smith et al. |
| 2003/0099668 A1 | 5/2003 | Bachmann |
| 2003/0108611 A1 | 6/2003 | Bosch et al. |
| 2003/0108923 A1 | 6/2003 | Tuschl et al. |
| 2003/0133988 A1 | 7/2003 | Fearon |
| 2003/0134810 A1 | 7/2003 | Springate et al. |
| 2003/0138557 A1 | 7/2003 | Allison |
| 2003/0143184 A1 | 7/2003 | Seo |
| 2003/0162761 A1 | 8/2003 | Steiner et al. |
| 2003/0165478 A1 | 9/2003 | Sokoll |
| 2003/0175950 A1 | 9/2003 | McSwiggen |
| 2003/0219766 A1 | 11/2003 | Raitano et al. |
| 2003/0225040 A1 | 12/2003 | Dalton et al. |
| 2003/0228603 A1 | 12/2003 | Cload |
| 2003/0232013 A1 | 12/2003 | Sieckman et al. |
| 2003/0232792 A1 | 12/2003 | Dalton et al. |
| 2003/0235619 A1* | 12/2003 | Allen et al. .................. 424/490 |
| 2004/0014789 A1 | 1/2004 | Lau |
| 2004/0014975 A1 | 1/2004 | Dalton et al. |
| 2004/0022727 A1 | 2/2004 | Stanton |
| 2004/0022840 A1 | 2/2004 | Nagy et al. |
| 2004/0029913 A1 | 2/2004 | Dalton et al. |
| 2004/0043923 A1 | 3/2004 | Parma et al. |
| 2004/0052727 A1 | 3/2004 | Dalton et al. |
| 2004/0054190 A1 | 3/2004 | Pomper |
| 2004/0059094 A1 | 3/2004 | Bachmann et al. |
| 2004/0067196 A1 | 4/2004 | Brunke et al. |
| 2004/0067503 A1 | 4/2004 | Tan et al. |
| 2004/0067979 A1 | 4/2004 | Dalton et al. |
| 2004/0072234 A1 | 4/2004 | Parma et al. |
| 2004/0086544 A1 | 5/2004 | Bezemer |
| 2004/0087810 A1 | 5/2004 | Dalton et al. |
| 2004/0092470 A1 | 5/2004 | Leonard et al. |
| 2004/0136961 A1 | 7/2004 | Prokop |
| 2004/0141958 A1 | 7/2004 | Steinaa |
| 2004/0147489 A1 | 7/2004 | Dalton et al. |
| 2004/0147550 A1 | 7/2004 | Dalton et al. |
| 2004/0156846 A1 | 8/2004 | Daum et al. |
| 2004/0167103 A1 | 8/2004 | Dalton et al. |
| 2004/0192626 A1 | 9/2004 | McSwiggen et al. |
| 2004/0241790 A1 | 12/2004 | Eriksen et al. |
| 2004/0247680 A1 | 12/2004 | Farokhzad |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1 | 2/2005 | Farokhzad et al. |
| 2005/0048063 A1 | 3/2005 | Ruoslahti et al. |
| 2005/0069910 A1 | 3/2005 | Turner et al. |
| 2005/0079152 A1 | 4/2005 | Bot |
| 2005/0079533 A1 | 4/2005 | Samuelson |
| 2005/0079553 A1 | 4/2005 | Ayyoub |
| 2005/0080128 A1 | 4/2005 | Tsukamoto et al. |
| 2005/0100877 A1 | 5/2005 | Xu et al. |
| 2005/0107322 A1 | 5/2005 | O'Hagan |
| 2005/0122550 A1 | 6/2005 | Plewa et al. |
| 2005/0136258 A1 | 6/2005 | Nie |
| 2005/0142582 A1 | 6/2005 | Doyle |
| 2005/0158390 A1 | 7/2005 | Rana et al. |
| 2005/0191294 A1 | 9/2005 | Arap et al. |
| 2005/0207940 A1 | 9/2005 | Butler |
| 2005/0214378 A1* | 9/2005 | Hoarau et al. ................. 424/490 |
| 2005/0233948 A1 | 10/2005 | D'Amico et al. |
| 2005/0239134 A1 | 10/2005 | Gorenstein |
| 2005/0244863 A1 | 11/2005 | Mir |
| 2005/0249799 A1 | 11/2005 | Jacob et al. |
| 2005/0256071 A1 | 11/2005 | Davis |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |
| 2006/0009529 A1 | 1/2006 | Dalton et al. |
| 2006/0035966 A1 | 2/2006 | Dalton et al. |
| 2006/0057219 A1 | 3/2006 | Nagasaki |
| 2006/0062787 A1 | 3/2006 | Hitraya |
| 2006/0083711 A1 | 4/2006 | Berry et al. |
| 2006/0110460 A1 | 5/2006 | Ferret |
| 2006/0111271 A1 | 5/2006 | Cerny |
| 2006/0165987 A1 | 7/2006 | Hildgen |
| 2006/0173170 A1 | 8/2006 | Chamberlian et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |
| 2006/0287547 A1 | 12/2006 | Dalton et al. |
| 2007/0014807 A1 | 1/2007 | Maida |
| 2007/0041901 A1 | 2/2007 | Diener |
| 2007/0043066 A1 | 2/2007 | Sum |
| 2007/0053845 A1 | 3/2007 | Sengupta |
| 2007/0116768 A1 | 5/2007 | Chorny |
| 2007/0184068 A1 | 8/2007 | Renner |
| 2007/0224225 A1 | 9/2007 | IracheGarreta |
| 2007/0225213 A1 | 9/2007 | Kosak |
| 2008/0019908 A1 | 1/2008 | Akitsu |
| 2008/0026000 A1 | 1/2008 | Ennifar |
| 2008/0031899 A1 | 2/2008 | Reddy |
| 2008/0057102 A1 | 3/2008 | Roorda |
| 2008/0081074 A1 | 4/2008 | Gu et al. |
| 2008/0124400 A1 | 5/2008 | Liggins |
| 2008/0171059 A1 | 7/2008 | Howland |
| 2008/0193381 A1 | 8/2008 | Babich |
| 2008/0213377 A1 | 9/2008 | Bhatia |
| 2008/0268063 A1 | 10/2008 | Jon et al. |
| 2008/0299177 A1 | 12/2008 | Hardy |
| 2009/0004118 A1 | 1/2009 | Nie |
| 2009/0028910 A1 | 1/2009 | DeSimone et al. |
| 2009/0061010 A1 | 3/2009 | Zale |

(56) References Cited

U.S. PATENT DOCUMENTS

| | | |
|---|---|---|
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad et al. |
| 2010/0022680 A1 | 1/2010 | Karnik et al. |
| 2010/0068285 A1 | 3/2010 | Zale |
| 2010/0068286 A1 | 3/2010 | Troiano |
| 2010/0069426 A1 | 3/2010 | Zale |
| 2010/0092425 A1 | 4/2010 | Von Andrian et al. |
| 2010/0104655 A1 | 4/2010 | Zale |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang |
| 2010/0216804 A1 | 8/2010 | Zale |
| 2010/0226986 A1 | 9/2010 | Grayson |
| 2010/0233251 A1 | 9/2010 | Von Andrian et al. |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| JP | 2006528954 | 5/2006 |
| KR | 0418916 | 3/2002 |
| KR | 0041712 | 6/2004 |
| WO | WO 88/04300 | 6/1988 |
| WO | WO 90/11364 | 3/1990 |
| WO | 9006430 | 6/1990 |
| WO | 9006433 | 6/1990 |
| WO | 9106286 | 5/1991 |
| WO | 9106287 | 5/1991 |
| WO | 9503356 | 2/1995 |
| WO | 9503357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | 99/01498 | 1/1999 |
| WO | WO 99/34850 | 7/1999 |
| WO | 9955715 | 11/1999 |
| WO | 0059538 | 1/2000 |
| WO | WO 00/21572 | 4/2000 |
| WO | WO 00/27363 | 5/2000 |
| WO | 0032239 | 6/2000 |
| WO | WO 00/44895 | 8/2000 |
| WO | WO 01/75164 | 10/2001 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/000777 | 1/2003 |
| WO | WO 03/004654 | 1/2003 |
| WO | 03033592 | 4/2003 |
| WO | WO 03/028657 | 4/2003 |
| WO | WO 03/030941 | 4/2003 |
| WO | WO 03/051304 | 6/2003 |
| WO | 03074679 | 9/2003 |
| WO | WO 03/072637 | 9/2003 |
| WO | WO 03/102708 | 12/2003 |
| WO | 2004009116 | 1/2004 |
| WO | 2004030608 | 4/2004 |
| WO | WO 2004/030608 | 4/2004 |
| WO | WO 2004/071493 | 8/2004 |
| WO | 2004096140 | 11/2004 |
| WO | WO 2004/096998 | 11/2004 |
| WO | 2004105782 | 12/2004 |
| WO | WO 2005/012407 | 2/2005 |
| WO | WO 2005/028539 | 3/2005 |
| WO | 2005046572 | 5/2005 |
| WO | WO 2005/042573 | 5/2005 |
| WO | WO 2005/072710 | 8/2005 |
| WO | 2005105056 | 11/2005 |
| WO | WO 2005/111192 | 11/2005 |
| WO | 2005112885 | 12/2005 |
| WO | 2005112886 | 12/2005 |
| WO | WO 2005/121181 | 12/2005 |
| WO | 2006025627 | 3/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | 2006093991 | 9/2006 |
| WO | 2006099445 | 9/2006 |
| WO | WO 2006/096754 | 9/2006 |
| WO | WO 2006/117217 | 11/2006 |
| WO | WO 2006/133271 | 12/2006 |
| WO | WO 2006/138463 | 12/2006 |
| WO | 2007001448 A2 | 1/2007 |
| WO | 2007052058 | 1/2007 |
| WO | WO 2007/021142 | 2/2007 |
| WO | 2007024026 | 3/2007 |
| WO | 2007034479 | 3/2007 |
| WO | 2007131972 | 5/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | WO 2007/109364 | 9/2007 |
| WO | WO 2007/118653 | 10/2007 |
| WO | 2007133807 | 11/2007 |
| WO | 2007137117 | 11/2007 |
| WO | 2007144807 A2 | 12/2007 |
| WO | WO 2007/150030 | 12/2007 |
| WO | 2008019142 | 2/2008 |
| WO | 2008041703 | 4/2008 |
| WO | 2008043157 | 4/2008 |
| WO | 2008058192 | 5/2008 |
| WO | WO 2008/051291 | 5/2008 |
| WO | 2008105772 | 9/2008 |
| WO | 2008105773 | 9/2008 |
| WO | 2008121949 | 10/2008 |
| WO | 2008124632 | 10/2008 |
| WO | 2008124634 | 10/2008 |
| WO | 2008124639 | 10/2008 |
| WO | 2008147456 | 12/2008 |
| WO | WO 2009/051837 | 4/2009 |
| WO | 2009109428 | 9/2009 |
| WO | WO 2009/109428 | 9/2009 |
| WO | 2010005721 | 1/2010 |
| WO | 2010005723 | 1/2010 |
| WO | 2010005725 | 1/2010 |
| WO | 2010005726 | 1/2010 |
| WO | 2010068866 | 6/2010 |
| WO | 2010075072 | 7/2010 |
| WO | 2010114768 | 10/2010 |
| WO | 2010114770 | 10/2010 |
| WO | 2011072218 | 6/2011 |

OTHER PUBLICATIONS

CAS Reg. No. 1069-79-0 (Nov. 16, 1984).*

Bilati, Ugo, Eric Allémann, and Eric Doelker. "Development of a nanoprecipitation method intended for the entrapment of hydrophilic drugs into nanoparticles." European Journal of Pharmaceutical Sciences 24.1 (2005): 67-75.*

Zhang, Liangfang, et al. "Self-assembled lipid-polymer hybrid nanoparticles: a robust drug delivery platform." ACS nano 2.8 (2008): 1696-1702.*

(56) References Cited

OTHER PUBLICATIONS

Chan, Juliana M., et al. "PLGA-lecithin-PEG core-shell nanoparticles for controlled drug delivery." Biomaterials 30.8 (2009): 1627-1634.*
Bies et al., Lectin-medicated drug targeting: history and applications, *Advanced Drug Delivery Reviews*, 56:425-435 (2004).
Bocca, et al., "Phagocytic uptake of fluorescent stealth solid lipid nanoparticles", *Int. J. Pharmaceutics*, 175:185-193 (1998).
Brooking et al., "Transport of Nanoparticles Across the Rat Nasal Mucosa", *Journal of Drug Targeting*, 9(4):267-279 (2001).
Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).
Chandy, et al., "5-Fluorouracil-loaded chitosan coated polylactic acid pmicrospheres as biodegradable drug carriers for cerebral tumors", *J. Microencapsulation*, 17(5):625-638 (2000).
Cheng, et al., "Formulation of functionatized PLGA-PEG nanoparticles for in vivo targeted drug delivery", *Biomaterrials*, 28:869-875 (2007).
Coppi, et al., "Chitosan-Alginate Microparticles as a Protein Carrier", *Drug Development and Industrial Pharmacy*, 27(5):393-400 (2001).
Elvassore, et al., "Production iof Insulin-Loaded Poly(Ethylene Glycol)/Poly(/-Lactide) (PEG/PLA) Nanoparticles by Gas Antisolvent Techniques", *Journal of Pharmaceutical Sciences*, 90(10):1628-36 (2001).
Ermak and Giannasca, "Microparticle targeting to M cells", *Advanced Drug Delivery Reviews*, 34:261-283 (1998).
Fi Li Povic-Grcic et al., "Mucoadhesive chitosan-coated liposomes: characteristics and stability", *J. Microencapsulation*, 18 1:3-12 (2001).
Gaserod et al., "The enhancement of the bioadhesive properties of calcium alginate gel beads by coating with chitosan", *Intl. J. of Pharmaceutics*, 175:237-246 (1998).
Hejazi et al ., "Stomach-specific anti-H. pylon therapy. I: preparation and characterization of tetracyline-loaded chitosan microshpheres", *Intl. J. of Pharmaceutics*, 235:87-94 (2002).
Huang et al., "Microencapsulation of Chlorpheniramine Maleate-Resin Particles with Crosslinked Chitosan for Sustained Release", *Pharmaceutical Development and Technology*, 41:107-115 (1999).
Janes et al., "Chitosan nanoparticles as delivery systems for doxorubicin", *Journal of Controlled Release*, 73:255-267 (2001).
Jayasena, "Aptamers: An Emerging Class of Molecules That Rival Antibodies in Diagnostics", *Clinical Chemistry*, 45(9):1628-1650 (1999).
Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(1):77-85 (2000).
Khandare, et al., "Polymer-drug conjugates: Progress in polymeric prodrugs," *Progress in Polymer Science*, 31(4): 359-397 (2006).
Kim, et al., "Target-specific cellular uptake of PLGA nanoparticles coated with poly(L-lysine)-poly(ethyleneglycol)-folate conjugate", *Langmuir*, 21(19): 8852-8857 (2005).
Lehr, "Lectin-mediated drug delivery: The second generation of bioadhesives", *J. of Controlled Release*, 65:19-29 (2000).
Lim et al., "Preparation and evaluation of the in vitro drug release properties and mucoadhesion of novel microspheres of hyaluronic acid and chitosan", *J. of Controlled Release*, 66:281-292 (2000).
Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).
Olivier, et al., "Drug Transport to Brain with Targeted Nanoparticles", *J. of the Am. Society of Experimental Neuro Therapeutics*, 2:108-119 (2005).
Pimentel, et al., "Peptide nanoparticles as novel immunogens: design and analysis of a prototypic severe acute respiratory syndrome vaccine", *Chemical Biology & Drug Design*, 73(1):53-61 (2009).

Ponchel, et al., "Specific and non-specific bioadhesive particulate systems for oral delivery to the gastrointestinal tract", *Advanced Drug Delivery Reviews*, 34:191-219 (1998).
Shimoda, et al., "Bioadhesive Characteristics of Chitosan Mircroshperes to the Mucosa of Rat Small Intestine", *Drug Delvelopment and Inustrial Pharmacy*, 27(6):567-576 (2001).
Simberg, et al., "Biomimetic amplification of nanoparticle homing to tumors", *Nat'l. Acad Sic. USA*, 104(3):921-936 (2007).
Takeuchi, et al., "Enteral Absorption of Insulin in Rats from Mucoadhesive Chitosan-Coated Liposomes", *Pharmaceutical Research*, 13(6):896-901 (1996).
Takeuchi et al., "Mucoashesive Lipsomes Coated with Chitosan or Carbopol for Oral Administration of Peptide Drugs", *Proceed. Intl. Symp. Control. Rel. Bioact. Mater.*, 26:988-989 (1999).
Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).
Tavitian, et al., "In vivo imaging with oligonucleotides for diagnosis and drug development", *Gut, 52 Su*, I IV :40-47 (2003).
Tobio, et al "Role of PEG on the stability in digestive fluids and in vivo fate of PEG-PLA nanoparticles following oral administration", *Colloids and Surfaces B: Biointerferences*, 18:315-323 (2000).
Vila, et al., "Design of biodegradable particles for protein delivery", *Journal of Controlled Release*, 78:15-24 (2002).
Vila, et al., "PLA-PEG Nanospheres: New Carriers for Transmucosal Delivery of Proteins and Plasmid DNA", *Poly. Adv. Technol.*, 13:851-858 (2002).
Yamada, et al., "In Vitro and in Viva Evaluation of Sustained Release Chitosan-Coat Ketoprofen Microparticles", *Yakugaku Zesshi*, 121(3):239-245 (2001).
Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).
Yuan, et al., "Intranasal immunization with chitosan/pCETP nanoparticles inhibits atherosclerosis in a rabbit model of atherosclerosis", *Vaccine, Bitterworth Scientific*, 26:29-30 (2008).
Heald, et al., "Poly(lactic acid)-poly(ethylene oxide) (PLA-PEG) nanoparticles: NMR studies of the central solidlike PLA core and the liquid PEG corona", *Langmuir*, 18:3669-3675 (2002).
Tomai, et al., "Resiquimod and other immune response modifiers as vaccine adjuvants", Expert Rev Vaccines, 6:835-847 (2007) Abstract Only.
Villa, et al., "PLA-PEG particles as nasal protein carriers: the influence of the particle size", *Int. J Pharmaceut.*, 292:43-52 (2005).
Sarkar, et al., "Ligand-DNA interaction in a nanocage of reverse micelle", Biopolymer., 83(6):675-86 (2006).
International Search Report mailed Jul. 8, 2008.
U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,465, filed May 5, 2010, Farokhzad, et al.
U.S. Appl. No. 12/526,300, filed Aug. 11, 2010, Moretti, et al.
Abad, et al., "Comparison of a Monoclonal Antibody-Based Enzyme-Linked Immunosorbent Assay and Gas Chromatography for the Determination of Nicotine in Cigarette Smoke Condensates", *Anal. Chem.*, 65:3227-3231 (1993).
Ackermand & Cresswell, "Cellular mechanisms governing cross-presentation of exogenous antigens", *Nat. Immunol.*, 5(7):678-684 (2004).
Aime, et al., "Lanthanide(III) chelates for NMR biomedical applications", *Chemical Society Reviews*, 27:19-29 (1998).
Akaishi, et al., "Targeting Chemotherapy Using Antibody-Combined Liposome against Human Pancreatic Cancer Cell-Line", *Tohoku J. Exp. Med.*, 175(1):29-42 (1995).
Allen, et al., "Nano-engineering block copolymer aggregates for drug delivery.", *Colloids Surfaces B-Biointerfaces*, 16:3-27 (1999).
Allison, et al., "The mode of action of immunological adjuvants.", *Dev. Biol. Stand.*, 92:3-11 (1998).
Altschul, et al., "Basic local alignment search tool.", *J. Mol Biol.*, 215(3):403-10 (1990).
Altschul, et al., "Gapped BLAST and PSI-BLAST: a new generation of protein database search programs.", *Nucleic Acids Res.*, 25(17):3389-3402 (1997).

(56) References Cited

OTHER PUBLICATIONS

Angelucci, et al., "Neuroendocrine transdifferentiation induced by VPA is mediated by PPARγ activation and confers resistance to antiblastic therapy in prostate carcinoma", *The Prostate*, 68(6):588-598 (2008).
Astete and Sabliov, "Synthesis and characterization of PLGA nanoparticles", *J. Biomat. Sci.,-Polymer Ed.*, 17:247-289 (2006).
Atkinson, et al., "Conjugation of folate via gelonin carbohydrate residues retains ribosomal-inactivating properties of the toxin and permits targeting to folate receptor positive cells.", *J. Biol. Chem.*, 276(30):27930-27935 (2001).
Baba, et al., "Human neutralizing monoclonal antibodies of the IgG1 subtype protect against mucosal simian-human immunodeficiency virus infection.", *Nat. Med.*, 6(2):200-206 (2000).
Babaian, et al., "Radioimmunological imaging of metastatic prostatic cancer with 111indium-labeled monoclonal antibody PAY 276.", *J. Urol.*, 137(3):439-443 (1987).
Bachmann, et al., "T helper cell-independent neutralizing B cell response against vesicular stomatitis virus: role of antigen patterns in B cell induction?", *Eur. J. Immunol.*, 25(12):3445-3451 (1995).
Bagalkot, et al., "An Aptamer-Doxorubicin Physical Conjugate as a Novel Targeted Drug-Delivery Platform", *Angew. Chem. Int. Ed.*, 45(48):8149-8152 (2006).
Bander, et al., "Targeting metastatic prostate cancer with radiolabeled monoclonal antibody J591 to the extracellular domain of prostate specific membrane antigen.", *J. Urol.*, 170(5):1717-1721 (2003).
Barchet, et al., "Virus-induced interferon alpha production by a dendritic cell subset in the absence of feedback signaling in vivo.", *J. Exp. Med.*, 195(4):507-516 (2002).
Barrera, et al., "Synthesis and RGD peptide modification of a new biodegradable copolymer: poly(lactic acid-co-lysine)", *J. Am. Chem. Soc.*, 115(23):11010-11011 (1993).
Bauer, et al., "SMS 201-995: a very potent and selective octapeptide analogue of somatostatin with prolonged action.", *Life Sci.*, 31(11):1133-1140 (1982).
Beaurepaire, et al., "Functionalized Fluorescent Oxide Nanoparticles: Artificial Toxins for Sodium Channel Targeting and Imaging at the Single-Molecule Level", *Nano Letters*, 4(11):2079-2083 (2004).
Bennett, et al., "Inhibition of the Aminopeptidase from Aeromonas Proteolytica by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *EMBO J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", *J. Exp. Med.*, 196(12):1627-1638 (2002).
Bottausci, et al., "Mixing in the shear superposition micromixer: three-dimensional analysis", *Philosophical Transactions of the Royal Society of London Series a-Mathematical Physical and Engineering Sciences*, 362:1001-1018 (2004).
Boussif, et al., "A versatile vector for gene and oligonucleotide transfer into cells in culture and in vivo: polyethylenimine.", *Proc. Natl. Acad. Sci., USA*, 1995, 92:7297-7301 (1995).
Bozzacco, et al., "DEC-205 receptor on dendritic cells mediates presentation of HIV gag protein to CD8+ T cells in a spectrum of human MHC I haplotypes.", *Proc. Natl. Acad. Sci., USA*, 104(4):1289-1294 (2007).
Brito, et al., "Nanoparticulate carriers for the treatment of coronary restenosis.", *Int J Nanomedicine*, 2(2):143-161 (2007).
Burmeister, et al., "Direct in vitro selection of a 2'-O-methyl aplamer to VEGF.", *Chem Biol*, 12(1):25-33 (2005).
Carino, et al., "Nanosphere based oral insulin delivery," *J. Control. Release*, 65(1-2):261-9 (2000).
Casola, et al., "B cell receptor signal strength determines B cell fate.", *Nat. Immunol.*, 5(3):317-327 (2004).
Castro & Prieto, "Nicotine Antibody Production: Comparison of two nicotine conjugates in different animal species", *Biochem. Biophys. Res. Comm.*, 67(2):583-589 (1975).
Castro, et al., "Nicotine Antibodies: Comparison of Ligand Specificities of Antibodies Produced against Two Nicotine Conjugates", *Eur. J. Biochem.*, 104:331-340 (1980).
Chacon, et al., "Optimized preparation of poly D,L (lactic-glycolic) microspheres and nanoparticles for oral administration", *Int'l J. Pharmaceutics*, 141:81-91 (1996).
Chaires, et al., "Preferential binding of daunomycin to 5'ATCG and 5'ATGC sequences revealed by footprinting titration experiments.", *Biochemistry*, 29(26):6145-6153 (1990).
Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).
Cheng, et al., "Formulation of functionalized PLGA-PEG nanoparticles for in vivo targeted drug delivery.", *Biomaterials*, 28(5):869-876 (2007).
Christian, et al., "Nucleolin expressed at the cell surface is a marker of endothelial cells in angiogenic blood vessels.", *J. Cell Biol.*, 163(4):871-878 (2003).
Chu, et al., "Aptamer mediated siRNA delivery", *Nuc. Acid Res.*, 34:e73 (2006).
Chu, et al., "Labeling tumor cells with fluorescent nanocrystal-aptamer bioconjugates.", *Biosens. Bioelectron.*, 21:1859-1866 (2006).
Clark, "The reticulum of lymph nodes in mice studied with the electron microscope.", *Am. J. Anat.*, 110:217-257 (1962).
Connor, et al., "Ex vivo evaluation of anti-EpCAM immunocytokine huKS-IL2 in ovarian cancer.", *J. Immunother.*, 27(3):211-219 (2004).
Croy and Kwon, "Polymeric micells for drug delivery", *Curr. Pharm. Design*, 12:4669-4684 (2006).
D'Antonio, et al., "Longitudinal analysis of androgen deprivation of prostate cancer cells identifies pathways to androgen independence", *The Prostate*, 68(7):698-714 (2008).
Dang and Rock, "Stimulation of B lymphocytes through surface Ig receptors induces LFA-1 and ICAM-1-dependent adhesion.", *J. Immunol.*, 146(10):3273-3279 (1991).
De Graaf, et al., "A fully human anti-Ep-CAM scFv-beta-glucuronidase fusion protein for selective chemotherapy with a glucuronide prodrug.", *Br. J. Cancer*, 86(5):811-818 (2002).
De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4):473-483 (2000).
Delemarre, et al., "Repopulation of macrophages in popliteal lymph nodes of mice after liposome-mediated depletion.", *J. Leukoc. Biol.*, 47(3):251-257 (1990).
Demello and Demello, "Microscale reactors: nanoscale products.", *Lab on a Chip*, 4(2):11N-15N (2004).
Demello, "Control and detection of chemical reactions in microfluidic systems.", *Nature*, 442(7101):394-402 (2006).
Deming, et al., "Facile synthesis of block copolypeptides of defined architecture.", *Nature*, 390(6658):386-389 (1997).
Derfus, et al., "Intracellular Delivery of Quantum Dots for Live Cell Labeling and Organelle Tracking", *Advanced Materials*, 16:961-966 (2004).
Dimarco and Arcamone, "DNA complexing antibiotics: Daunomycin, adriamycin and their derivates.", *Arzneim-Forsch. (Drug Res.)*, 25:368-375 (1975).
Ding, et al., "Syntheses of conformationally constricted molecules as potential NAALADase/PSMA inhibitors.", *Org. Lett.*, 6(11):1805-1808 (2004).
Dinkla, et al., "Identification of a streptococcal octapeptide motif involved in acute rheumatic fever.",*J. Biol. Chem.*, 282(26):18686-18693 (2007).

(56) References Cited

OTHER PUBLICATIONS

Dykxhoorn, et al., "Killing the messenger: short RNAs that silence gene expression.", *Nat. Rev. Mol. Cell Biol.*, 4(6):457-467 (2003).
Eklund, et al., "Denileukin diftitox: a concise clinical review.", *Expert Rev. Anticancer Ther.*, 5(1):33-38 (2005).
Elbashir, et al., "RNA interference is mediated by 21- and 22-nucleotide RNAs.", *Genes Dev.*, 15(2):188-200 (2001).
Eldridge, et al., "Biodegradable microspheres as a vaccine delivery system," *Mol. Immunol.*, 28(3):287-94 (1991).
Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).
Farokhazad, et al., "Nanoparticle-Aptamer Bioconjugates: A New Approach for Targeting Prostate Cancer Cells," *Cancer Research*, 64:7668-7672 (2004).
Farokhzad, et al., "Nanoparticle-aptamer bioconjugates for cancer targeting", *Expert Opin. Drug Delivery*, 3(3):311-324 (2006).
Farokhzad, et al., "Targeted nanoparticle-aptamer bioconjugates for cancer chemotherapy in vivo.", *Proc. Natl. Acad. ScL, USA*, 103(16):6315-6320 (2006).
Farr, et al., "The structure of the sinus wall of the lymph node relative to its endocytic properties and transmural cell passage.", *Am. J. Anat.*, 157(3):265-284 (1980).
Fire, et al., "Potent and specific genetic interference by double-stranded RNA in Caenorhabditis elegans.", *Nature*, 391(6669):806-811 (1998).
Fonseca, et al., "Paclitaxel-loaded PLGA nanoparticles: preparation, physicochemical characterization and in vitro anti-tumoral activity.", *J. Control. Release*, 83(2):273-286 (2002).
Fracasso, et al., "Anti-tumor effects of toxins targeted to the prostate specific membrane antigen.", *Prostate*, 53(1):9-23 (2002).
Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).
Frederick, et al., "Structural comparison of anticancer drug-DNA complexes: adriamycin and daunomycin.", *Biochemistry*, 29(10):2538-2549 (1990).
Froidevaux, et al., "Somatostatin analogs and radiopeptides in cancer therapy.", *Biopolymers*, 66(3):161-183 (2002).
Fujita, et al., "Cytokine profiling of prostatic fluid from cancerous prostate glands identifies cytokines associated with extent of tumor and inflammation", *The Prostate*, 68(8):872-882 (2008).
Gao, et al., "A method for the generation of combinatorial antibody libraries using pIX phage display," *Proc. Natl. Acad. Sci. U.S.A.*, 99(20): 12612-6 (2002).
Gao, et al., "In vivo cancer targeting and imaging with semiconductor quantum dots.", *Nat. Biotechnol.*, 22(8):969-976 (2004).
Gao, et al., "In vivo molecular and cellular imaging with quantum dots.", *Curr. Op. Biotechnol.*, 16:63-72 (2005).
Gershlick, "Treating atherosclerosis: local drug delivery from laboratory studies to clinical trials," *Atherosclerosis*, 160(2): 259-71 (2002).
Gillies, et al., "An anti-CD20-IL-2 immunocytokine is highly efficacious in a SCID mouse model of established human B lymphoma.", *Blood*, 105(10):3972-3978 (2005).
Grauer, et al., "Identification, purification, and subcellular localization of prostate-specific membrane antigen PSM' protein in the LNCaP prostatic carcinoma cell line.", *Cancer Res.*, 58(21):4787-4789 (1998).
Gref, et al., "Biodegradable long-circulating polymeric nanospheres.", *Science*, 263(5153):1600-1603 (1994).
Haensler, et al., "Polyamidoamine cascade polymers mediate efficient transfection of cells in culture", *Bioconjugate Chem.*, 4(5):372-379 (1993).

Haj, et al., "New findings in the study on the intercalation of bisdaunorubicin and its monomeric analogues with naked and nucleus DNA.", *Chem. Biol. Interact.*, 145(3):349-358 (2003).
Hanes, et al., "Polymer microspheres for vaccine delivery.", *Pharm. Biotechnol.*, 6:389-412 (1995).
Hangartner, et al., "Antiviral immune responses in gene-targeted mice expressing the immunoglobulin heavy chain of virus-neutralizing antibodies.", *Proc. Natl. Acad. Sci., USA*, 100:12883-12888 (2003).
Hannon, et al., "Unlocking the potential of the human genome with RNA interference", *Nature*, 431(7006):371-378 (2004).
Harada and Kataoka, "Supramolecular assemblies of block copolymers in aqueous media as nanocontainers relevant to biological applications", *Progress Polymer Sci.*, 31(11):949-982 (2006).
Harper, et al., "Efficacy of a bivalent L1 virus-like particle vaccine in prevention of infection with human papillomavirus types 16 and 18 in young women: a randomised controlled trial.", *Lancet*, 364(9447):1757-1765 (2004).
Haseloff and Gerlach, "Simple RNA enzymes with new and highly specific endoribonuclease activities.", *Nature*, 334(6183):585-591 (1988).
Hawiger, et al., "Dendritic cells induce peripheral T cell unresponsiveness under steady state conditions in vivo.", *J. Exp. Med.* 194(6):769-779 (2001).
He, et al., "A microRNA polycistron as a potential human oncogene," *Nature*, 435(7043): 828-833 (2005).
Hélène, "The anti-gene strategy: control of gene expression by triplex-forming-oligonucleotides.", *Anticancer Drug Des.* 6(6):569-584 (1991).
Helene, et al., "Control of gene expression by triple helix-forming oligonucleotides. The antigene strategy.", *Ann, N.Y. Acad. Sci.* 660:27-36 (1992).
Hermann and Patel, "Adaptive recognition by nucleic acid aptamers," *Science*, 287: 820-825 (2000).
Hieda, et al., "Active Immunization Alters the Plasma Nicotine Concentration in Rats", *J. Pharmacol. Exp. Therapeutics*, 283:1076-1081 (1997).
Hieda, et al., "Immunization of rats reduces nicotine distribution to brain", *Psychopharmacology*, 143:150-157 (1999).
Horoszewicz, et al., "Monoclonal antibodies to a new antigenic marker in epithelial prostatic cells and serum of prostatic cancer patients.", *Anticancer Res.*, 7(5B):927-935 (1987).
Houghton, "General method for the rapid solid-phase synthesis of large numbers of peptides: Specificity of antigen-antibody interaction at the level of individual amino acids", *Immunol.*, 82:5131-5135 (1985).
Jackson, et al., "Design and pharmacological activity of phosphinic acid based NAALADase inhibitors.", *J. Med. Chem.*, 44(24):4170-4175 (2001).
Jackson, et al., "Design of NAALADase inhibitors: a novel neuroprotective strategy.", *Curr. Med. Chem.*, 8(8):949-957 (2001).
Johnson and Prud'homme, "Mechanism for rapid self-assembly of block copolymer nanoparticles.", *Phys. Rev. Lett.*, 91(11):118302 (2003).
Jones and Leroux, "Polymeric micelles—a new generation of colloidal drug carriers", *Eur. J. Pharmaceutics Biopharmaceutics*, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).
Junt, et al., "Subcapsular sinus macrophages in lymph nodes clear lymph-borne viruses and present them to antiviral B cells", *Nature*, 450:110-116 (2007).
Kabanov, et al., "DNA Complexes with Polycations for the Delivery of Genetic Material into Cells", *Bioconjugate Chem.*, 6(1):7-20 (1995).
Kamentsky, "Laser scanning cytometry.", *Methods Cell Biol.*, 63:51-87 (2001).
Kanashiro, et al., "Inhibition of mutant p53 expression and growth of DMS-153 small cell lung carcinoma by antagonists of growth hor-

(56) References Cited

OTHER PUBLICATIONS mone-releasing hormone and bombesin.", *Proc. Natl. Acad. Sci., USA*, 100(26):15836-15841 (2003).
Karlin and Altschul, "Applications and statistics for multiple high-scoring segments in molecular sequences.", *Proc. Natl Acad. Sci. USA*, 90(12):5873-5877 (1993).
Karlin and Altschul, "Methods for assessing the statistical significance of molecular sequence features by using general scoring schemes.", *Proc. Natl Acad Sci. USA*, 87:2264-2268 (1990).
Karrer, et al., "On the key role of secondary lymphoid organs in antiviral immune responses studied in alymphoplastic (aly/aly) and spleenless (Hox11(−)/−) mutant mice.", *J. Exp. Med.*, 185(12):2157-2170 (1997).
Kelly, et al., "The Optical Properties of Metal Nanoparticles: The Influence of Size, Shape, and Dielectric Environment", *J. Phys. Chem. B.*, 107(3):668-677 (2003).
Khademhosseini, et al., "Cell docking inside microwells within reversibly sealed microfluidic channels for fabricating multiphenotype cell arrays," *Lab Chip*, 5(12):1380-6 (2005).
Knight, et al., "Hydrodynamic Focusing on a Silicon Chip: Mixing Nanoliters in Microseconds", *Phys. Rev. Lett.*, 80:3863-3866 (1998).
Köhrer and Rajbhandary, "Proteins carrying one or more unnatural amino acids," In Ibba, et al., (eds.), *Aminoacyl-tRNA Synthetases*, Landes Bioscience, Chapter 31(2005).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).
Köhrer, et al., "Import of amber and ochre suppressor tRNAs into mammalian cells: a general approach to site-specific insertion of amino acid analogues into proteins.", *Proc. Natl. Acad. Sci., USA*, 98(25):14310-14315 (2001).
Koivunen, et al., "Phage libraries displaying cyclic peptides with different ring sizes: ligand specificities of the RGD-directed integrins.", *Biotechnology (NY)*, 13(3):265-270 (1995).
Koivunen, et al., "Tumor targeting with a selective gelatinase inhibitor ", *Nat. Biotechnol.*, 17:768-774 (1999).
Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).
Kozikowski, et al., "Synthesis of urea-based inhibitors as active site probes of glutamate carboxypeptidase II: efficacy as analgesic agents.", *J. Med. Chem.*, 47(7):1729-1738 (2004).
Krieg, et al., "CpG motifs in bacterial DNA trigger direct B-cell activation.", *Nature*, 374(6522):546-549 (1995).
Kreitman, et al., "Efficacy of the anti-CD22 recombinant immunotoxin BL22 in chemotherapy-resistant hairy-cell leukemia.", *N. Engl J. Med.*, 345(4):241-347 (2001).
Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).
Kukowska-Latallo, et al., "Efficient transfer of genetic material into mammalian cells using Starburst polyamidoamine dendrimers", *Proc. Natl. Acad. Sci., USA*, 93(10):4897-4902 (1996).
Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).
Kwon, et al., "Pseudopoly(amino acids): A study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci., USA*, 101(25):9381-9386 (2004).
Labhasetwar, et al., "Arterial uptake of biodegradable nanoparticles: Effect of surface modifications ," *J. Pharm. Sci.*, 87(10): 1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and γ-(3-Pyridyl)- γ-oxo-N-methylbutyramide", *Met. Enzymol.*, 84:628-640 (1982).
Leamon, et al., "Cytotoxicity of folate-Pseudomonas exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al, "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).
Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).
Liu, et al., "Folate-targeted enzyme prodrug cancer therapy utilizing penicillin-V amidase and a doxorubicin prodrug.", *J. Drug Target.*, 7:43-53 (1999).
Liu, et al., "Hypermethylation of MCAM gene is associated with advanced tumor stage in prostate cancer", *The Prostate*, 68(4):418-426 (2008).
Liu, et al., "Monoclonal antibodies to the extracellular domain of prostate-specific membrane antigen also react with tumor vascular endothelium.", *Cancer Res.*, 57(17):3629-3634 (1997).
Low, et al., "Folate receptor-targeted drugs for cancer and inflammatory diseases.", *Adv. Drug Deliv. Rev.*, 56(8):1055-1058 (2004).
Lu, et al., "MicroRNA expression profiles classify human cancers", *Nature*, 435(7043):834-838 (2005).
Ludewig, et al., "Induction of optimal anti-viral neutralizing B cell responses by dendritic cells requires transport and release of virus particles in secondary lymphoid organs.", *Eur. J. Immunol.*, 30(1):185-196 (2000).
Lupold, et al., "Identification and characterization of nuclease-stabilized RNA molecules that bind human prostate cancer cells via the prostate-specific membrane antigen.", *Cancer Res.*, 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).
Maher, "DNA triple-helix formation: An approach to artificial gene repressors?", *Bioassays* 14:807-815 (1992).
Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).

(56) References Cited

OTHER PUBLICATIONS

Manolova, et al., "Nanoparticles target distinct dendritic cell populations according to their size", *Eur. J. Immunol.*, 38:1404-1413 (2008).
Manz, et al., "Capillary electrophoresis on a chip", *J. Chromatography*, 593:253-258 (1992).
Mathiowitz, et al., "Polyanhydride Microspheres as Drug Carriers I. Hot Melt Encapsulation", *J. Control. Release*, 5:13-22 (1987).
Mathiowitz, et al., "Novel microcapsules for delivery systems", *Reactive Polymers*, 6:275-283 (1987).
Mathiowitz, et al., "Polyanhydride Microspheres as Drug Carriers. II.Microencapsulation by Solvent Removal", *J. Appl. Polymer Sci.*, 35:755-774 (1988).
Mattheakis, et al., "Optical coding of mammalian cells using semiconductor quantum dots.", *Analytical Biochemistry*, 327(2):200-208 (2004).
Maung, et al., "Probing for a hydrophobic a binding register in prostate-specific membrane antigen with phenylalkylphosphonamidates.", *Bioorg. Med. Chem.*, 12(18):4969-4979 (2004).
McDevitt, et al., "An alpha-particle emitting antibody ([213Bi]J591) for radioimmunotherapy of prostate cancer.", *Cancer Res.*, 60(21):6095-6100 (2000).
McDevitt, et al., "Tumor therapy with targeted atomic nanogenerators.", *Science*, 294(5546):1537-1540 (2001).
Mead, et al., "Laboratory vector competence of black flies (Diptera:simuliidae) for the Indiana serotype of vesicular stomatitis virus.", *Ann. N.Y. Acad. Sci.*, 916:437-443 (2000).
Meister, et al., "Mechanisms of gene silencing by double-stranded RNA.", *Nature*, 431(7006):343-349 (2004).
Melani, et al., "Targeting of interleukin 2 to human ovarian carcinoma by fusion with a single-chain Fv of antifolate receptor antibody.", *Cancer Res.*, 58(18):4146-4154 (1998).
Mempel, et al., "T-cell priming by dendritic cells in lymph nodes occurs in three distinct phases.", *Nature*, 427(6970):154-159 (2004).
Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).
Meyers, et al., "Development of monoclonal antibody imaging of metastatic prostatic carcinoma.", *Prostate*, 14(3):209-220 (1989).
Milligan and Uhlenbeck, "Synthesis of small RNAs using T7 RNA polymerase," *Methods in Enzymology*, 180: 51-62 (1989).
Moghimi, et al., "Long-circulating and target-specific nanoparticles: theory to practice," *Pharmacol. Rev.*, 53(2): 283-318 (2001).
Mulligan, "The basic science of gene therapy," *Science*, 260(5110):926-32 (1993).
Murphy, et al., "Isolation and characterization of monoclonal antibodies specific for the extracellular domain of prostate specific membrane antigen.", *J. Urol.*, 160(6 Pt 2):2396-2401 (1998).
Murray, et al., "Synthesis and characterization of monodisperse nanocrystals and close-packed nanocrystal assemblies", *Ann. Rev. Mat. Sci.*, 30:545-610 (2000).
Myers and Miller, *CABIOS* (1988.
Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).
Neidle, "The molecular basis for the action of some DNA-binding drugs.", *Prog. Med. Chem.*, 16:151-221 (1979).
Nguyen and Wu, "Micromixers—a review.", *J. Micromechan. Microeng.*, 15:R1 (2005).
Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).
Ochsenbein, et al., "Protective T cell-independent antiviral antibody responses are dependent on complement.", *J. Exp. Med.*, 190(8):1165-1174 (1999).

Ochsenbein, et al., "Control of early viral and bacterial distribution and disease by natural antibodies.", *Science*, 286(5447):2156-2159 (1999).
O'Donnell, et al., "c-Myc-regulated microRNAs modulate E2F1 expression," *Nature*, 435(7043): 839-843 (2005).
Okada, et al., "Antigen-engaged B cells undergo chemotaxis toward the T zone and form motile conjugates with helper T cells.", *PLoS Biol.*, 3(6):e150 (2005).
Oliver, et al., "Conformational and SAR analysis of NAALADase and PSMA inhibitors.", *Bioorg. Med. Chem.*, 11(20):4455-4461 (2003).
Pape, et al., "The humoral immune response is initiated in lymph nodes by B cells that acquire soluble antigen directly in the follicles.", *Immunity*, 26(4):491-502 (2007).
Papisov, "Acyclic Polyacetals from Polysaccharides: Biomimetic Biomedical "Stealth" Polymers", *ACS Symposium Series*, 786:301-314 (2001).
Parekh, et al., "Biomarkers for Prostate Cancer Detection", *The Journal of Urology*, 178(6):2252-2259 (2007).
Pasqualini, et al., "Aminopeptidase N is a receptor for tumor-homing peptides and a target for inhibiting angiogenesis.", *Cancer Res.*, 60(3):722-727 (2000).
Patri, et al., "Synthesis and in Vitro Testing of J591 Antibody-Dendrimer Conjugates for Targeted Prostate Cancer Therapy", *Bioconj. Chem.*, 15:1174-1181 (2004).
Pellegrino, et al., "On the development of colloidal nanoparticles towards multifunctional structures and their possible use for biological applications.", *Small*, 1(1):48-63 (2005).
Pfohl, et al., "Trends in microfluidics with complex fluids.",*Chemphyschem*, 4(12):1291-1298 (2003).
Phillips, et al., "Enhanced antibody response to liposome-associated protein antigens: preferential stimulation of IgG2a/b production.", *Vaccine*, 10(3):151-158 (1992).
Porkka, et al., "A fragment of the HMGN2 protein homes to the nuclei of tumor cells and tumor endothelial cells in vivo.", *Proc. Natl. Acad. Sci., USA*, 99(11):7444-7449 (2002).
Putnam, et al., "Poly(4-hydroxy-l-proline ester): Low-Temperature Polycondensation and Plasmid DNA Complexation", *Macromolecules*, 32(11):3658-3662 (1999).
Qi, et al., "Extrafollicular activation of lymph node B cells by antigen-bearing dendritic cells", *Science*, 312(5780):1672-1676 (2006).
Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34+ progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci., USA*, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor 1/2 ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form

(56) References Cited

OTHER PUBLICATIONS of the Pseudomonas exotoxin termed PE-38 (TP-38) for the treatment of malignant brain tumors.", *J. Neurooncol.*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci., USA*, 97(3):996-1001(2000).
Shaida, et al., "Expression of BNIP3 correlates with hypoxia-inducible factor (HIF)-1α, HIF-2α and the androgen receptor in prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).
Smith-Jones, et al., "In vitro characterization of radiolabeled monoclonal antibodies specific for the extracellular domain of prostate-specific membrane antigen.", *Cancer Res.*, 60(18):5237-5243 (2000).
Sondel, et al., "Preclinical and clinical development of immunocytokines.", *Curr. Opin. Investig. Drugs*, 4(6):696-700 (2003).
Song, et al., "A Microfluidic System for Controlling Reaction Networks in Time", *Angewandte Chemie—Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al., "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).
Taylor, et al., "Macrophage receptors and immune recognition.", *Annu. Rev. Immunol.*, 23:901-944 (2005).
Tindall, et al., "The Rationale for Inhibiting 5α-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).

Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: A fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor signaling directs membrane trafficking.", *Curr., Opin., Immunol.*, 19(1):93-98 (2007).
Vihko, et al., "Radioimaging of Prostatic Carcinoma With Prostatic Acid Phosphatase—Specific Antibodies", *Biotechnology in Diagnostics*, 131-134 (1985).
Von Allmen, et al., "V domain of RAGE interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4):1152-1163 (1987).
Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci., USA*, 92(25):11490-11494 (1995).
Whelan, et al., "Efficient recovery of infectious vesicular stomatitis virus entirely from cDNA clones.", *Proc. Natl. Acad. Sci., USA*, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for cellular research.", *J. Magn. Reson.*, 147(2):371-377 (2000).
Wlotzka, et al., "In vivo properties of an anti-GnRH Spiegelmer: an example of an oligonucleotide-based therapeutic substance class," *Proc. Natl. Acad. Sci. U. S. A.*, 99(13):8898-902 (2002).
Wright, et al., "Cyclophosphamide/granulocyte colony-stimulating factor causes selective mobilization of bone marrow hematopoietic stem cells into the blood after M phase of the cell cycle.", *Blood*, 97(8):2278-2285 (2001).
Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(11:25-33 (2000).

(56) References Cited

OTHER PUBLICATIONS

Zauner, et al., "Polylysine-basedtransfection systems utilizing receptor-mediated delivery.", Adv. Drug Del. Rev., 30:97-113 (1998).
Zhang, et al., "The proliferative effect of estradiol on human prostate stromal cells is mediated through activation of ERK", The Prostate, 68(5):508-516 (2008).
Zheng, et al., "Highly fluorescent, water-soluble, size-tunable gold quantum dots.", Phys. Rev. Lett., 93(7):077402 (2004).
Zhou, et al., "Investigation on a novel core-coated microspheres protein delivery system.", J. Control. Release, 75(1-2):27-36 (2001).
Zhou, et al., "Preparation of poly(L-serine ester): a structural analog of conventional poly(L-serine)", Macromolecules, 23(14):3399-3406 (1990).
Zuker, "Mfold web server for nucleic acid folding and hybridization prediction", Nuc. Acid. Res., 31:3406-3415 (2003).
Cerchia, et al. "Neutralizing aptamers from whole-cell SELEX inhibit the RET receptor tyrosine kinase", PLoS Biology, 3(4):849-60 (2005).
Foss, et al., "Radiolabeled small-molecule ligands for prostate-specific membrane antigen: in vivo imaging in experimental models of prostate cancer", Clin. Cancer Res., 11:4022-28 (2005).
Govender, et al., "Defining the drug incorporation properties of PLA-PEG nanoparticles", Intl J of Pharmaceutics, 1999:95-110(2000).
Mitra, et al., "Tumour targeted delivery of encapsulated dextran-doxorubicin conjugate using chitosan nanoparticles as carrier", J Controlled Release, 74:317-23 (2001).
Wu, et al., ng-circulation Poly(ethylene glycol)-poly(D,L-lactide) block copolymermicelles with modulated surace chane, J Contl Rel., 77:27-38 (2001).
Zhou, et al., "NAAG peptidase inhibitors and their potential for diagnosis and therapy", Nature Rev. Drug Disc., 4:1015-26 (2005).
Adams, et al., Amphiphilic block copolymers for drug delivery, J. Pharm. Sci., 92(7):1343-55 (2003).
Astete and Sabliov, "Synthesis and characterization of PLGA nanoparticles", J. Biomat. Sci.,—Polymer Ed., 17:247-289 (2006).
Balenga, et al., "Protective efficiency of dendrosomes as novel nano-sized adjuvants for DNA vaccination against birch pollen allergy", J Biotech., 123(3):602-14 (2006).
Barinka, et al., "Interactions between human glutamate carboxypeptidase II and urea-based inhibitors: Structural characterization", J Med. Chem.,51:7737-43 (2008).
Barinka, et al., "Structural insight into the pharmacophore pocket of human glutamate carboxypoeptidase II", J. Med Chem., 50:3267-73 (2007).
Beck, et al., "A New Long-acting Injectable Microcapsule System for the Administration of Progesterone," Fertil. & Steril., 31(5):545-55 (1979).
Benita, et al., "Characterization of Drug-Loaded Poly(d,/-lactide) Microspheres," J. Pharm. Sci. 73(12):1721-24 (1984).
Caliceti, et al. "Effective protein release from PEG/PLA nano-particles produced by compressed gas anti-solvent precipitation techniques", J of Cont. Release, 94:195-205 (2004).
Ch'ng, et al., "Bioadhesive Polymers as Platforms for Oral Controlled Drug Delivery II: Synthesis and Evaluation of Some Swelling, Water-Insoluble Bioadhesive Polymers," J. Pharm. Sci. 74: 399-405 (1988).
Chandran, at al, "Characterization of a targeted nanoparticle functionalized with a Urea-based inhibitor of prostate-specific membrane antigen (PSMA)", Cancer Biol & Therapy, 7(4):1-9 (2008).
Chen, et al., "Radiohalogenated prostate-specific membrane antigen (PSMA)-based ureas as imaging agents for prostate cancer", J Med Chem., 51(24):7933-43 (2008).
Chickering & Mathiowitz, "Bioadhesive microspheres: i. A novel electrobalance-based method to study adhesive interactions between individual microspheres and intestinal mucosa," J. Control. Release 34:251-62 (1995).
Dancey, et al., "Therapeutic Targets:MTOR an related pathways", Cancer Biol. Ther., 5(9)1065-73 (2006).

Duchene, et al., "Pharmaceutical and Medical Aspects of Bioadhesive Systems for Drug Administration," Drug Development &. Ind. Pharm, 14(2&3):283-31 (1988).
Ewesuedo and Ratain, "Systemically administered drugs", Drug Delivery Systems in Cancer, Humana Press, Chapter 1:3-14 (2004).
Farokhzad, et al., "Cancer nanotechnology: drug encapsulated nanoparticle-aptmer bioconjugates for targeted delivery to prostate cancer cells", 13th Eu. Cancer Conf., Oct. 30-Nov. 3, Paris France (2005).
Gu, et al "Precise engineering of targeted nanoparticles by using self-assembled . biointegrated block copolymers", PNAS, 105(7):2586-91 (2008).
Gurney, et al., "Bioadhesive intraoral release systems: design, testing and analysis," Biomaterials 5:336-40 (1984).
Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).
Hong, et al., "Enhanced and prolonged cross-presentation following endosomal escape of exogenous antigens encapsulated in biodegradable nanoparticles", Immunol., 117(1):78-88 (2006).
Hotter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
Humblet, et al. "An HPLC/mass spectrometry platform for the development of multimodality contrast agents and targeted therapeutics: prostate-specific membrane antigen small derivatives", Contrast Med. Mol, Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Igaku, "Intracellular trafficking of lipid antigens and their immune recognition by the CD1 system", Exp. Med., 24(7):936-40 (2006).
Illum, "Bioadhesive Microspheres as Potential Nasal Drug Delivery System," Int'l J. Pharm. 39: 189-99 (1987).
Jiang, et al., "Preparation of PLA and PLGA nanoparticles y binary organic solvent diffusion method", J. Cent. South Univ Technol, 10(3):202-06 (2003).
Kozikowski, et al. "Design of remarkably simple, yet potent urea-based inhibitors of glutamate carboxypeptidase II (NAALADase)", J. Med Chem, 44:298-301 (2001).
Labat-Robert & Decaens, "Glycoproteines du mucus gastrique: structure, fonctions et pathologie," Pathologie Biologie 24:241 (Paris 1979).
Lee, et al. "Adaptations of Nanoscale Viruses and Other Protein Cages for Medical Applications" Nanomedicine-Nanotechnology Biology and Medicine. 2 (3):137-149 (2006).
Lehr, et al., "In vitro evaluation of mucoadhesive properties of chitosan and some other natural polymers," International J. Pharmaceutics 78: 43-48 (1992).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Leon-Bay, et al, "Microsphere formation and drug delivery in a series of derivatized amino acids," Winter conference of Medicinal Chemistry (Steamboat Springs, Colarodo 1995).
Maresca, et al., "A series of halogenated heterodimeric inhibitors of prostate specific membrane antigen(PSMA) as radiolabeled probes for targeting prostate cancer", J. Med Chem., 52(2):347-57 (2009).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mathiowitz, et al., "Morphology of polyanhydride microsphere delivery systems," Scanning Microscopy 4(2):329-340 (1990).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14 (10):3036-43 (2008).
Mikos, et al., "Interaction of Polymer Microspheres with Mucin Gels as a Means of Characterizing Polymer Retention on Mucus," J. Colloid & Interface Sci. 143(2):366-73 (1991).

(56) References Cited

OTHER PUBLICATIONS

Misra, et al., "Production of multimeric prostrate-specific membrane antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6 (2005).
Pulkkinen, et al., "Three-step tumor of paclitaxel using blotinylated PLA-PEG nanoparticles and avidin-biolin technology: Formulation developing and in vitro anticancer activity", Eur. J Pharm, Biopharm., 70:66-74 (2008).
Raghuvanshi, et al., "Improved immune response from biodegradable polymer particles entrapping tetanus toxoid by use of different immunization protocol and adjuvants", Int J Pharm., 245(1-2):109-21 (2002).
Sapra, et al., "Ligan-targeted liposomal anticancer drugs", Pergamon, Progress in Lipid Research, 42:439-462 (2003).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol. 36:295-99 (1984).
Spiro, "Glycoproteins," Annual Review of Biochemistry 39:599-638 (Snell, ed. 1970).
Surgery Frontier, "What's new in surgery frontier", 13(3):290-3 (2006).
Sweetman, "Entry for Docetaxel" , Martindaie:the complete drug reference, 33rd ed., p. 534 (2002).
Tobio, et al.,"Stealth PLA-PEG nanoparticlea as protein carriera for nasal administration", Pharm. Res., 15(2):270-75 (1998).
Walter, et al., "Hydrophillic poly (DL-lactide-co-glycolide) microspheres for the delivery of DNA to human-derived macrophages and dendritic cells", J Control Release, 76(1-2):149-68 (2001).
Yamamoto, et al., " Long-circulation Poly(ethylene glycol)-poly(D,L-lactide) block copolymermicelles with modulated surace chane", J Contl Rel., 77:27-38 (2001).
Yang, et al., "Micelles formed by self-assmbling of polylactide(ethylene glycol) block copolymers in aqueous solutions", J Colloid Interfac Si., 314:470-77 (2007).
Akagi, et al., "Multifunctional conjugation of proteins on/into bio-nanoparticles prepared by amphiphilic poly(gamma-glutamic acid)", J Biomat Sci Polym Ed., 17 (8):875-92 (2006).
Akagi, et al., "Development of vaccine adjuvants using polymeric nanoparticles and their potential applications for anti-HIV vaccine", Yakugaku Zasshi, 127(2):307-17 (2007) English Abstract.
Argov-Argaman, et al., "Lactosomes: Structural and compositional classification of unique nanometer-sized protein lipid particles of human milk", J Agric Food Chem., 58:11234-42 (2010).
Avgoustakis, "Pegylated poly(lactide) and poly(lactide-co-glycolide) nanoparticles: preparation, properties and possible applications in drug delivery", Curr Drug Deliv., 1:321-33 (2004).
Chu, et al, "Aptamer:toxin conjugates that specifically target prostate tumor cells", Cancer Res., 66:5989-92 (2006).
Elamanchili, et al., ""Pathogen-mimicking" nanoparticles for vaccine delivery to dendritic cells, J Cont. Rel., 30(4):378-95 (2007).
Gorelik, at al., "Scanning surface confocal microscopy for simultaneous topographical and fluorescence imaging: application to single virus-like particle entry into a cell", PNAS, 99(25):16018-23 (2002).
Hallahanm, et al., "Integrin-mediated targeting of drug delivery to irradiated tumor blood vessels", Cancer Cell, 3:63-74 (2003).
Harris, et al., "Proteolytic actuation o nanoparticle self-assembly", Angewandte Chemie, 118:3233-7 (2006).
Hennenfent, et al., "Novel formulations of taxanes: a review. Old wine in a new bottle", Ann Oncol., 17:735-49 (2005).
Jayaprakash, et al., "Design and synthesis of a PSMA inhibitor-doxorubicin conjugate for targeted prostate cancer therapy", Chem Med Chem., 1:299-302 (2006).

Kawamura, et al., "Dendritic cells that endocytosed antigen-containing IgG-liposomes elicit effective antitumor immunity", J Immunother., 29(2):165-74 (2006).
Koenig, et al., "Immunologic factors in human milk: the effects of gestational age and pasteurization", J Human Lactation, 21:439-43 (2002).
Lamalle-Bernard, et al., "Coadsorption of HIV-1 p24 and gp120 proteins to surfactant-free anionic PLA nanoparticles preserves antigenicity and immunogenicity" , J Control Rel., 115(1):57-67 (2006).
Martin, et al., "Crystal structure at 2.8 A of an FcRn/heterodimeric Fc complex: mechanism of pH-dependent binding.", Mol Cell, 7:867-77 (2001).
Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).
McNeil, "Nanotechnology for the biologist", J Leukoc Biol., 78:575-94 (2005).
Moon, et al., "Engineering Nano- and microparticles to tune immunity", Adv Mater., DOI:10.1002/adma.201200446 (2012).
Oyewumi, et al., "Comparison of cell uptake, biodistribution and tumor retention of folate-coated and PEG-coated gadolinium nanoparticles in tumor-bearing mice", J Control Rel., 93:613-26 (2004).
Oyewumi, et al., "Nano-microparticles as immune adjuvants: correlating particle sizes and the resultant immune responses", Exp Rev Vaccines, 9(9):1095-1107 (2010).
Riley, et al., "Colloidal stability and drug incorporation aspects of micellar-like PLA-PEG nanoparticles", Colloids Surfaces B Biointerfaces, 16:147-59 (1999).
Riley, et al., "Physicochemical evaluation of nanoparticles assembled from Poly(lactic acid)-Poly(ethylene glycol) (PLA_PEG) block copolymers as drug delivery vehicles", Langmuir, 17;3168-74 (2001).
Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).
Shim, "One target different effects: a comparison of distinct therapeutic antibodies against the same targets", Exp Mole Med.,43(10):539-49 (2011).
Suzuki, et al., "Development of effective antigen delivery carrier to dendritic cells via Fc receptor in cancer immunotherapy",Yakugaku Zasshi, 127(2):301-6 (2007). English Abstract.
Taylor, et al., "Development of a specific system for targeting protein to metallophilic macrophages", PNAS, 101(7):1963-8 (2004).
Uto, et al., "Targeting of antigen to dendritic cells with poly(gamma-glutamic acid) nanoparticles induces antigen-specific humoral and cellular immunity", J Immunology, 178(5):2979-86 (2007).
Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).
Yu, et al., "Engineered bio-nanocapsules, the selective vector for drug delivery system", IUBMB Like, 58(1):1-6 (2006).
Akagi, et al., "Preparation and characterization of biodegradable nanoparticles based on poly0gamma-glutamic acid) with L-Phenylalanine as a protein carrier", J Control Release, 108:226-36 (2005).
Akagi, et al., "Protein direct delivery to dendritic cells using nanoparticles based on amphiphilic poly(amino acid) derivatives", Biomaterials, 28:3427-36 (2007).
Akerman, et al., "Nanocrystal targeting in vivo", PNAS, 99(20):12617-21 (2002).
Anderson, et al., "Biodegradation and biocompatibility of PLA and PLGA microspheres", Adv Drug Delivery, 28:5-24 (1997).
Chen, et al., "Beta-arrestin 2 mediates endocytosis of type II TGF-beta receptor and down-regulation of its signaling", Science, 301:1394-7 (2003).
Deng, et al., Optimization of preparative conditions for poly-DL-lactide-polyethylene glycol microspheres with entrapped Vibrino Cholera antigens, J Control Release, 58(2):123-31 (1999).

(56) References Cited

OTHER PUBLICATIONS

Diwan, et al., "Biodegradable nanoparticle mediated antigen delivery to human cord blood derivced dendritic cells for induction of primary T cell repsonses", J Drug Targeting, 11(8-10):495-507 (2003).
Drug Delivery Systems, 22(3):289 (2007).
Fahmy, et al., "Targeted for drug delivery", Nano Today, 18-26 (2005).
Farokhzad, "Nanotechnology for drug delivery: the perfect partnership", Exp Opin Drug Deliv., 5(9):927-9 (2008).
Henrickson, et al., "T cell sensing of antigen dose governs interactive behavior wit dendritic cells and sets a threshold for T cell activation", Nat Immunol., 9(3):282-91 (2008).
Journal of Pediatric Practice, 64(9):1389-94 (2001).
Life Technologies, retrieved from the internet http://www.lifetechnologies.com/us/en/home/references/protocols/nucleic-acid-purification-and-analysis/ma-protocal/agarose-gel-electrophoresis-of-ma.html, retrieved May 30, 2014.
Morein, et al., "Current status and potential application of ISCOMs in veterinary medicine", Adv Drug Deliv Rev., 56:1367-82 (2004).
Nobs, et al., "Surface modification of poly(lactic acid) nanoparticles by covalent attahcment of thiol groups by means of three methods", Intl J Pharma., 250:327-37 (2003).
Ohuchi, et al., "Selection of RNA aptamers against recombinant transforming growth factor-$^2$ type III receptor displayed on cell surface", Biochimie, 88:897-904 (2006).
Olszewski, et al., "NAAG peptidase inhibition reduces locomotor activity and some stereotypes in the PCP model of schizophrenia via group II mGluR", J Neurochem., 89:876-85 (2004).
Ponchel, et al., "Mucoadhesion of colloidal particulate systems in the gastrointestinal tract", Eu J Pharma Biopharma., 44:25-31 (1997).
Raghavan, et al., "Fc receptors and their interactions with immunoglobulins", Annu Rev Cell Dev.,12:181-220 (1996) Abstract Only.
Ravetch and Bolland, "IgG Fc Receptors", Ann Rev Immunol., 19:275-90 (2001).
Schiffelers, et al., "Cancer siRNA theraphy by tumor selective delivery with ligand-targeted sterically stabilized nanoparticle", Nucleic Acids Res., 32(19):1-10 (2004).
Shadidi and Sioud, "Selection of peptides for specific delivery of oligonucleotides into cancer cells", Methods Molecular Biol., 252:569-80 (2004).
Singh, et al., "Nanoparticles and microparticles as vaccine-delivery systems", Expert Rev. Vaccines, 6(5):797-808 (2007).
Tamura, et al., "Regulation of Th2 responses by CpG motifs", Respiration, 121(12):1147-55 (2002).
Truong-Le, et al., "Gene transfer by DNA-Gelation nanospheres", Biochem and Biophy., 381:47-55 (1999).
Van de Winkel, et al., "Human Igl Fc receptor heterogeneity: molecular aspects and clinical implications", Immunology Today, 14(5):215-21 (1993).
Wakita, et a.., "Mechanisms for complete eradication of large tumor mass by liposome-CpG nanoparticle tumor vaccine", Clinical Immunology, 45(5):483-90 (2006).
Wei, et al., "Preparation of uniform-sized PELA microspheres with high encapsulation efficiency of antigens by premix membrane emulsification", J Colliod Interface Sci., 323(2):267-73 (2008).
Wu, et al.,"Selection of oligonucleotide apatamers with enhanced uptake and activation of human leukemia B cell", Human Gene, 14:849-60 (2003).
Yamamoto, et al., "Antinociceptive effects of N-acetylaspartyiglutamate (NAAG) peptidase inhibitors ZJ-11, ZJ-17 and ZJ-43 in the rat formalin test and in the rat neuropathic pain model", Eur J Neurosci., 20(2):483-94 (2004).
Yoo and Park, "Folate receptor targeted biodegradable polymeric doxorubicin micelles", J Cont. Rel., 96:273-83 (2004).
Zhou, et al., "Poly-D,L-lactide-co-poly(ethylene glycol) microspheres as potential vaccine delivery systems", J Control Release, 86:195-205 (2003).

\* cited by examiner

NP-Aptamer & LNCaP cells (Prostate cancer cells)

Non-targeted NP & LNCaP cells (Prostate cancer cells)

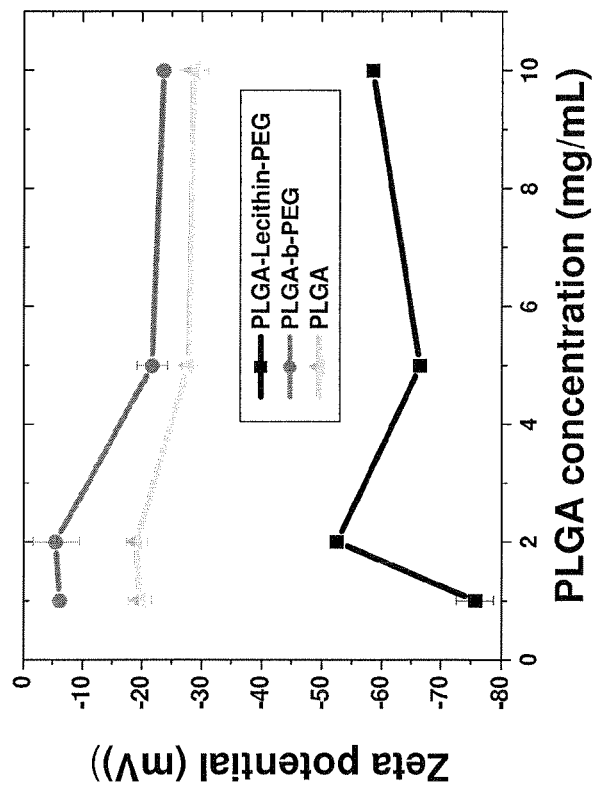
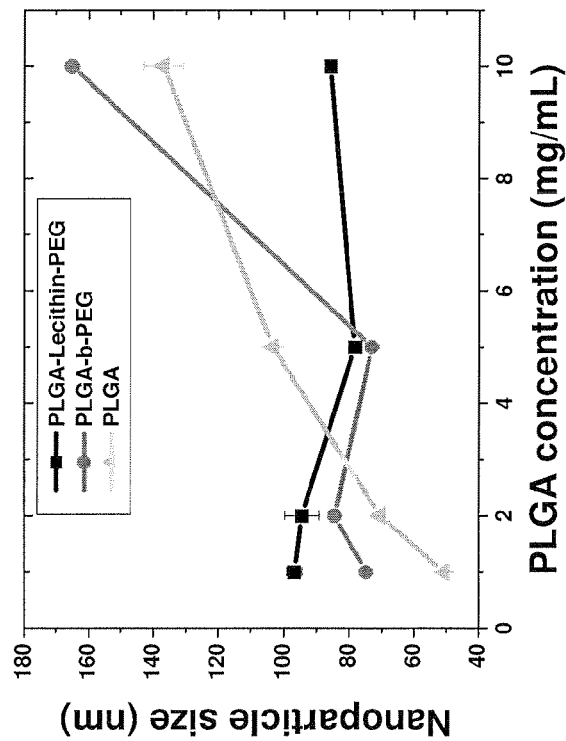
PLGA polymer concentration effect on nanoparticle size and zeta potential
Fig. 15B
Fig. 15A Stability of PLGA-Lipid-PEG, PLGA-PEG and PLGA nanoparticles in 10% BSA solution, respectively.

Stability of PLGA-Lipid-PEG, PLGA-PEG and PLGA nanoparticles in 10% plasma solution with heparin, respectively.

In vivo circulation profile of PLGA-Lipid-PEG NP and PLGA-PEG NP. The circulation half-life of them is about 20 hr and 3 hr respectively.

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Glu Arg Cys
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Arg Glu Lys Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Tyr Leu Gln Lys Leu Asn
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 4

Ala Xaa Tyr Leu Xaa Xaa Leu Asn
1               5

<210> SEQ ID NO 5
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaggacga ugcggaucag ccauguuuac gucacuccuu gucaauccuc aucggcagac    60
```

-continued

```
gacucgcccg a                                                           71

<210> SEQ ID NO 6
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggaggacga ugcggaccga aaaagaccug acuucuauac uaagucuacg uucccagacg      60
acucgcccga                                                             70

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Thr Trp Leu Pro Pro Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Cys Asp Cys Arg Gly Asp Cys Phe Cys Gly
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asn Gly Arg Cys
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Trp Gly Phe
1

<210> SEQ ID NO 11
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 11

Cys Thr Thr His Trp Gly Phe Thr Leu Cys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Gly Asn Lys Arg Thr Arg Gly Cys
1               5
```

AMPHIPHILIC COMPOUND ASSISTED NANOPARTICLES FOR TARGETED DELIVERY

RELATED APPLICATIONS

This application claims priority to U.S. Provisional Application No. 60/910,097, filed Apr. 4, 2007, titled "Amphiphilic compound assisted polymeric particles for targeted delivery;" U.S. Provisional Application No. 60/985,104, filed Nov. 2, 2007, titled "Lipid-Stabilized Polymeric Nanoparticles for Targeted Drug Delivery;" U.S. Provisional Application No. 60/938,590, filed May 17, 2007, titled "Poly(Amino Acid)-Targeted Drug Delivery;" U.S. Provisional Application No. 60/986,202, filed Nov. 7, 2007, titled "Poly(Amino Acid)-Targeted Drug Delivery;" and U.S. Provisional Application No. 60/990,250, filed Nov. 26, 2007, titled "Poly(Amino Acid)-Targeted Drug Delivery;" all of which are incorporated herein by reference in their entirety. Additionally, the contents of any patents, patent applications, and references cited throughout this specification are hereby incorporated by reference in their entireties.

STATEMENT REGARDING FEDERALLY SPONSORED RESEARCH OR DEVELOPMENT

This invention was made with government support under grant numbers EB003647 and U54CA119349 awarded by the National Institutes of Health. The government has certain rights in this invention.

FIELD OF INVENTION

The present invention generally relates to controlled-release systems comprising target-specific stealth nanoparticles useful in the treatment of diseases.

BACKGROUND

The delivery of a drug to a patient with controlled-release of the active ingredient has been an active area of research for decades and has been fueled by the many recent developments in polymer science. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs, as well as protein and peptide drugs and nucleic acids. The drugs are typically encapsulated in a polymer matrix which is biodegradable and biocompatible. As the polymer is degraded and/or as the drug diffuses out of the polymer, the drug is released into the body. Typically, polymers used in preparing these particles are polyesters such as poly(lactide-co-glycolide) (PLGA), polyglycolic acid, poly-beta-hydroxybutyrate, polyacrylic acid ester, etc. These particles can also protect the drug from degradation by the body. Furthermore, these particles can be administered using a wide variety of administration routes.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating a condition such as cancer, where it is desirable that a cytotoxic dose of the drug is delivered to cancer cells without killing the surrounding non-cancerous tissue. Effective drug targeting should reduce the undesirable and sometimes life threatening side effects common in anticancer therapy.

While many controlled release particle systems can accommodate significant quantities of drug, it can be difficult to encapsulate sufficient amounts of drug in nanoparticles. Identification of targeted nanoparticles that can encapsulate sufficient drug while still retaining therapeutic, targeting and stealth properties is desired.

SUMMARY OF THE INVENTION

There remains a need for compositions useful in the treatment, prevention or amelioration of one or more symptoms of diseases, such as cancer and vulnerable plaque, including cancers that express prostate specific membrane antigen (PSMA). Thus, in one aspect, the invention provides a controlled-release system, comprising a plurality of target-specific stealth nanoparticles; wherein the nanoparticles comprise a polymeric matrix, an amphipilic layer within or outside of the polymeric matrix, targeting moieties covalently attached to the outer surface of the nanoparticle; and a therapeutic agent. Cancers that can be treated by the nanoparticles of the invention include, but are not limited to, prostate cancer, breast cancer, non-small cell lung cancer, colorectal carcinoma, and glioblastoma, as well as solid tumors expressing PSMA in the tumor neovasculature. Atherosclerotic plaques, restenosis, and atherosclerosis can also be treated by the nanoparticles of the invention.

In one embodiment, the ratio of the amphipilic component of the amphipilic layer to the polymeric matrix of the nanoparticle is tailored for the effective treatment of diseases in a subject in need thereof. In another embodiment, the ratio of the amphipilic component of the amphipilic layer to the polymeric matrix is tailored to give a nanoparticle of a desired size. In a particular embodiment, the ratio of the amphipilic component of the amphipilic layer to the polymeric matrix is about 0.05 to about 0.50. In another embodiment, the ratio of the amphipilic component of the amphipilic layer to the polymeric matrix is about 0.12 to about 0.34. The nanoparticle can be nonimmunogenic.

In one embodiment, the nanoparticles are about 40 nm to about 500 nm in size. In another embodiment, the nanoparticles are about 40 nm to about 80 nm in size. In still another embodiment, the nanoparticles are about 40 nm to about 60 nm in size. In another embodiment, the nanoparticle is between 40 and 100 nm in diameter, and the targeting moiety is less than 10 nm in length, or the nanoparticle is between 40 and 80 nm in diameter, and the targeting moiety is less than 10 nm in length. In another embodiment, the nanoparticles have a surface zeta potential ranging from −80 mV to −30 mV.

In one embodiment, the amphipilic layer of the nanoparticle of the invention is a monolayer. The amphipilic layer can be comprised of naturally derived lipids, surfactants, or synthesized compounds with both hydrophilic and hydrophobic moieties. The amphipilic layer can comprise lecithin. The amphiphilic layer can be any thickness, such as about 1 nm to about 5 nm, or about 2.5 nm.

The nanoparticle of the invention has a polymeric matrix that can comprise two or more polymers. The polymeric matrix can comprise polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In one embodiment of the matrix, at least one polymer is a polyalkylene glycol, such as polyethylene glycol. In another embodiment of the matrix, at least one polymer is a polyester, such as PLGA. In another embodiment, the polymeric matrix comprises a copolymer of two or more polymers, such as a copolymer of a polyalkylene glycol and a polyester, e.g., a copolymer of PLGA and PEG.

In another embodiment, the polymeric matrix comprises a lipid-terminated polyalkylene glycol and a polyester, such as lipid-terminated PEG, and PLGA. As described below, the lipid can be of the Formula I, and can be 1,2 distearoyl-sn-glycero-3-phosphoethanolamine (DSPE), and salts thereof. The lipid of the lipid-terminated PEG can self-assemble with PLGA.

In another embodiment, the nanoparticle comprises a copolymer of PEG and PLGA, wherein an amphiphilic compound is disposed between the PEG and PLGA.

The nanoparticle can have any variety of targeting moieties, such as nucleic acid aptamers, growth factors, hormones, cytokines, interleukins, antibodies, integrins, fibronectin receptors, p-glycoprotein receptors, peptides and cell binding sequences. In one embodiment, the targeting moiety is a peptide, and wherein the peptide is less than 8 amino acids in length. In another embodiment, the targeting moiety is AKERC (SEQ ID NO: 1), CREKA (SEQ ID NO: 2), ARYLQKLN (SEQ ID NO: 3) or AXYLZZLN (SEQ ID NO: 4), wherein X and Z are variable amino acids. In still another embodiment, the targeting moiety is the A 10 RNA aptamer. In one embodiment, the polymer matrix of the nanopartiele is covalently bound to the targeting moiety via a maleimide functional group at the free terminus of PEG.

The pharmaceutical composition of the invention is suitable for target-specific treatment of a disease or disorder and delivery of a therapeutic agent. The therapeutic agent can be associated with the surface of, encapsulated within, surrounded by, or dispersed throughout the nanoparticle. In a particular embodiment, the therapeutic agent is encapsulated within the hydrophobic core of the nanoparticle. The therapeutic agent can be a biomolecule, bioactive agent, small molecule, drug, protein, vaccine, or polynucleotide. In a particular embodiment, the therapeutic agent is selected from the group consisting of mitoxantrone and docetaxel.

In another embodiment, the therapeutic agent is selected from the group consisting of VEGF, fibroblast growth factors, monocyte chemoatractant protein 1(MCP-1), transforming growth factor alpha (TGF-alpha), transforming growth factor beta (TGF-beta), DEL-1, insulin like growth factors (IGF), placental growth factor (PLGF), hepatocyte growth factor (HGF), prostaglandin E1(PG-E1), prostaglandin E2(PG-E2), tumor necrosis factor alpha (TNF alpha), granulocyte stimulating growth factor (G-CSF), granulocyte m acrophage colony-stimulating growth factor (GM-CSF), angiogenin, follistatin, and proliferin, PR39, PR11, nicotine, hydroxymethylglutaryl coenzyme A (HMG CoA) reductase inhibitors, statins, niacin, bile acid resins, fibrates, antioxidants, extracellular matrix synthesis promoters, inhibitors of plaque inflammation and extracellular degradation, and estradiol.

The invention also provides a method of treating prostate cancer in a subject in need thereof, comprising administering to the subject an effective amount of the pharmaceutical composition of the invention, such as when the targeting moiety of the nanoparticle of the invention is A10 RNA aptamer. The invention also provides a method of treating atherosclerotic plaques, restenosis, or atherosclerosis in a subject in need thereof, comprising administering to the subject an effective amount of the pharmaceutical composition of the invention. For disease treatment, the controlled-release system can administered systemically, such as via intravenous administration.

In another embodiment, the invention provides a method of preparing a nanoparticle comprising a polymeric matrix and an amphipilic layer associated with the polymeric matrix, comprising: conjugating a first polymer to a targeting moiety to form a first conjugate; adding the first conjugate and an amphiphilic component to a water miscible solvent to form a first solution; combining a second polymer with a therapeutic agent in a partially water miscible organic solvent to form a second solution; and combining the first and second solution such that the nanoparticle is formed. The water miscible solvent can be acetone, ethanol, methanol, or isopropyl alcohol. The partial water miscible organic solvent can be acetonitrile, tetrahydrouran, ethyl acetate, isopropyl alcohol, isopropyl acetate or dimethylformamide. In one embodiment of the method, the first polymer is PEG, the targeting moiety is an aptamer, the amphiphilic component is lecithin, and the second polymer is PLGA. The first polymer can be conjugated to DSPE, or salts thereof.

The invention also provides a nanoparticle, comprising a copolymer of PLGA and PEG, a targeting moiety, and a therapeutic agent, wherein lecithin is disposed between the PLGA and PEG. In another aspect, the invention provides a nanoparticle, comprising a polymeric matrix comprising a complex of a phospholipid bound-PEG and PLGA; a targeting moiety, and a therapeutic agent, wherein lecithin is disposed between the PLGA and PEG. The targeting moieties of these nanoparticles can be an A10 RNA aptamer or CREKA. The therapeutic agent for these nanoparticles can be docetaxel.

BRIEF DESCRIPTION OF THE DRAWINGS

FIGS. 15A and 15B demonstrate a PLGA polymer concentration effect on nanoparticle size and zeta potential, respectively.

DETAILED DESCRIPTION OF THE INVENTION

Figure 1:
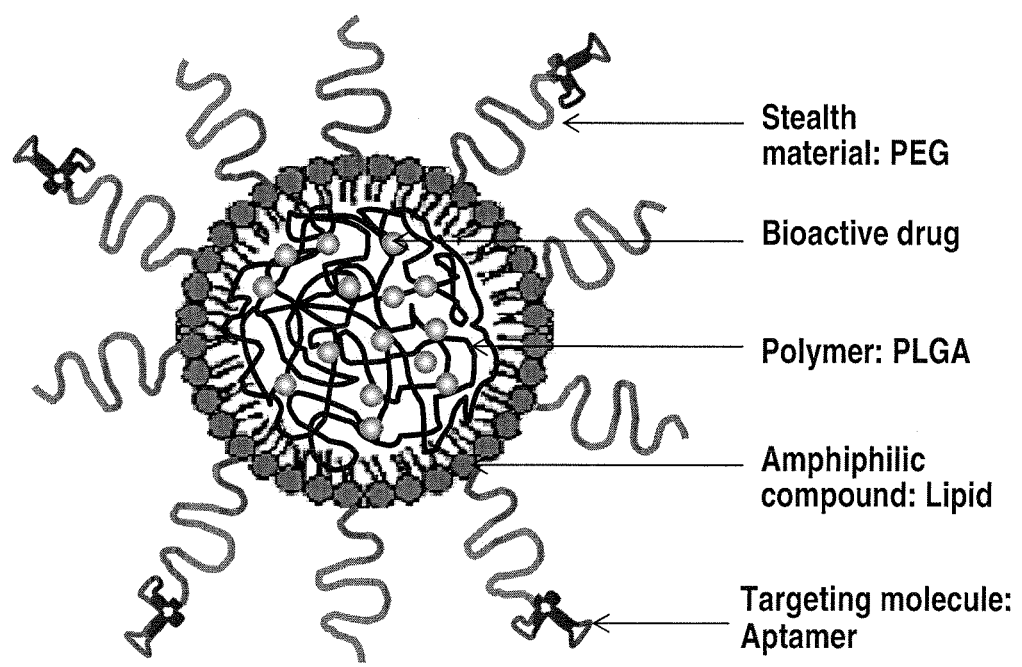
FIG. 1 shows a schematic illustration of an amphiphilic layer-protected polymeric nanoparticle for targeted drug delivery.

The present invention generally relates to amphipilic layer-protected nanoparticles, wherein the nanoparticles comprise a controlled-release system for the targeted delivery of a therapeutic agent. Thus, described herein are target-specific stealth nanoparticles with an amphiphilic layer that can reduce water penetration into the nanoparticle, thereby enhancing drug encapsulation efficiency and slowing drug release. Further, these amphipilic layer protected nanoparticles can provide therapeutic advantages by releasing the encapsulated drug and polymer at appropriate times.

Target-Specific Stealth Nanoparticles Comprising an Amphiphilic Compound

The amphipilic layer-protected nanoparticles of the invention have the following main components: 1) a polymeric matrix, which comprises a stealth polymer; 2) an amphiphilic compound or layer that surrounds or is dispersed within the polymeric matrix forming a continuous or discontinuous shell for the particle; and 3) a covalently attached targeting molecule that can bind to a unique molecular signature on cells, tissues, or organs of the body. In a particular embodiment, the polymeric matrix is comprised of a stealth polymer that can allow the particles to evade recognition by immune system components and increase particle circulation half life (e.g., PEG, as well as the other polymers described below), and a biodegradable polymeric material that forms the core of the particle (e.g., PLGA, as well as the other polymers described below), which can carry therapeutic agents and release them at a sustained rate after administration (e.g., cutaneous, subcutaneous, mucosal, intramuscular, ocular, systemic, oral or pulmonary administration).

In one embodiment, these particles would be useful in drug delivery for therapeutic applications. In an alternative embodiment, these particles would be useful for molecular imaging, for diagnostic applications, or for a combination thereof.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

The amphiphilic lipid can have a molecular weight of 200 to 1000, e.g., 700-900. An advantage of the nanoparticles of the present invention is that they require a relatively low amount of lipid to be effective. For example, as shown in Example 8, a nanoparticle of approximately 90 nm of polymer (e.g., PEG and PLGA) comprises only about 12 to about 15% lipid. By containing a relatively small amount of lipid, the nanoparticles of the invention avoid the negative impact that a tri, tetra or higher layer of lipid could have on a nanoparticle, such as an adverse effect on drug release. Thus, in one embodiment, the nanoparticles of the invention comprise approximately 10% to 40% lipid (by weight), and will have a size of about 90 nm to about 40 nm in diameter.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices.

The amphiphilic component of the nanoparticle of the invention can comprise a combination of lipids, which has some advantages over a single lipid.

In one embodiment, the invention comprises a nanoparticle comprising 1) a polymeric matrix, which comprises a stealth polymer; 2) an amphiphilic compound or layer that surrounds or is dispersed within the polymeric matrix forming a continuous or discontinuous shell for the particle; and 3) a covalently attached targeting molecule. In one embodiment, the invention comprises a nanoparticle comprising 1) a polymeric matrix, which comprises a stealth polymer; 2) an amphiphilic compound or layer that surrounds or is dispersed within the polymeric matrix forming a continuous or discontinuous shell for the particle; and 3) a covalently attached targeting molecule, wherein the nanoparticle diameter is between 40-80 nm and wherein the ratio of amphiphilic compound to polymer is between 14:1 and 34:1, by weight. In another embodiment, the invention comprises a nanoparticle comprising 1) a polymeric matrix, which comprises a stealth polymer; 2) lecithin; and 3) a covalently attached targeting molecule. In another embodiment, the invention comprises a nanoparticle comprising 1) a polymeric matrix, which comprises a stealth polymer; 2) lecithin; and 3) a covalently attached targeting molecule, wherein the nanoparticle diameter is between 40-80 nm and wherein the ratio of lecithin to polymer is between 14:1 and 34:1 by weight. In another embodiment, the invention comprises a nanoparticle comprising 1) a polymeric matrix, which comprises a stealth polymer; 2) a mixture of two or more amphiphilic compounds selected from phosphatidyl choline, phosphatidyl inositol, phosphatidyl ethanolamine, and phosphatidic acid; and 4) a covalently attached targeting molecule. In further embodiment, the invention comprises a nanoparticle comprising 1) a polymeric matrix, which comprises a stealth polymer; 2) a mixture of three or more amphiphilic compounds selected from phosphatidyl choline, phosphatidyl inositol, phosphatidyl ethanolamine, and phosphatidic acid; and 4) a covalently attached targeting molecule. In a still further embodiment, the invention comprises a nanoparticle comprising 1) a polymeric matrix, which comprises PLGA and PEG; 2) an amphiphilic compound or layer that surrounds or is dispersed within the polymeric matrix forming a continuous or discontinuous shell for the particle; and 4) a covalently attached targeting molecule. In another embodiment, the invention comprises a nanoparticle comprising 1) a polymeric matrix, which comprises PLGA and PEG; 2) lecithin; and 3) a covalently attached targeting molecule. In another embodiment, the invention comprises a nanoparticle comprising 1) a polymeric matrix, which comprises PLGA and PEG; 2) a mixture of two or more amphiphilic compounds selected from phosphatidyl choline, phosphatidyl inositol, phosphatidyl ethanolamine, and phosphatidic acid; and 4) a covalently attached targeting molecule. In one embodiment, the invention comprises a nanoparticle comprising 1) a polymeric matrix, which comprises PLGA and PEG; 2) lecithin; and 3) a covalently attached targeting molecule, wherein the nanoparticle diameter is between 40-80 nm and wherein the ratio of lecithin to polymer is between 14:1 and 34:1 by weight. In one embodiment of the aforementioned embodiments, the polymeric matrix comprises a biocompatible polymer, such as PLGA.

In certain embodiments of the invention, the amphiphilic layer of the nanoparticle, e.g., the layer of lecithin, is a monolayer, meaning the layer is not a phospholipid bilayer, but exists as a single continuous or discontinuous layer around, or within, the nanoparticle. A monolayer has the advantage of allowing the nanoparticles to be smaller in size, which makes them easier to prepare. The amphiphilic layer is "associated with" the nanoparticle of the invention, meaning it is positioned in some proximity to the polymeric matrix, such as surrounding the outside of the polymeric matrix (e.g., PLGA), or dispersed within the polymers that make up the nanoparticle.

In one embodiment, the nanoparticle of the controlled release system has an amount of targeting moiety (e.g., an aptamer or peptide) effective for the treatment of a disease in a subject in need thereof. The targeting moiety can be covalently bonded to the stealth polymer of the nanoparticle of the invention, or the amphiphilic component itself (e.g., lecithin). For example, when the polymeric matrix comprises PLGA and a PEG stealth polymer, the targeting moiety is covalently bonded to some or all of the PEG. The nanoparticle can have an optimized ratio of the functional and non-functional polymers (e.g., aptamer bound PEG and PEG with no aptamer), such that an effective amount of ligand is associated with the nanoparticle for a disease. For example, increased ligand density (e.g., on PEG) will increase target binding (cell binding/target uptake), making the nanoparticle "target specific." Alternatively, a certain concentration of non-functionalized polymer (e.g., non-functionalized PEG) in the nanoparticle can control inflammation and/or immunogenicity (i.e., the ability to provoke an immune response), and allow the nanoparticle to have a circulation half-life that is adequate for the treatment of a disease (e.g., cancer). Furthermore, the non-functionalized polymer can lower the rate of clearance from the circulatory system via the reticuloendothelial system. Thus, the non-functionalized polymer gives the nanoparticle "stealth" characteristics. Additionally, the non-functionalized polymer balances an otherwise high concentration of ligands, which can otherwise accelerate clearance by the subject, resulting in less delivery to the target cells.

In one embodiment, the invention is a nanoparticle comprising a targeting molecule covalently bound to a stealth polymer (e.g., PEG) and wherein the stealth polymer is covalently bound to the amphiphilic component. In another embodiment, the invention is a nanoparticle comprising a targeting molecule covalently bound to polyethylene glycol and wherein the polyethylene glycol is covalently bound to the amphiphilic component. In a further embodiment, the invention is a nanoparticle comprising a targeting molecule covalently bound to a stealth polymer and wherein the stealth polymer is covalently bound to lecithin. In a further embodiment, the invention is a nanoparticle comprising a targeting molecule covalently bound to a stealth polymer and wherein the stealth polymer is covalently bound to a mixture of two or more amphiphilic compounds selected from phosphatidyl choline, phosphatidyl inositol, phosphatidyl ethanolamine, and phosphatidic acid. In a further embodiment, the invention is a nanoparticle comprising a targeting molecule covalently bound to polyethylene glycol and wherein the polyethylene glycol is covalently bound to lecithin. In another embodiment, the invention comprises a nanoparticle comprising a molecule of the general formula: Targeting Molecule—Polyethylene Glycol—Amphiphilic Component; wherein "—" is a covelant bond.

In a further embodiment, the invention comprises a nanoparticle comprising a molecule of the general formula: Targeting Molecule—Polyethylene Glycol—Amphiphilic Component; wherein "—" is a covelant bond, and wherein the nanoparticle diameter is between 40-80 nm.

In a still further embodiment, the invention comprises a nanoparticle comprising a molecule of the general formula: Targeting Molecule—Polyethylene Glycol—Lecithin; wherein "—" is a covelant bond and wherein the nanoparticle diameter is between 40-80 nm.

In an additional embodiment, the invention comprises a nanoparticle comprising a polymer and molecule of the general formula: Targeting Molecule—Polyethylene Glycol—Lecithin; wherein "—" is a covelant bond and wherein the nanoparticle diameter is between 40-80 nm, and wherein the ratio of lecithin to polymer is between 14:1 and 34:1 by weight.

In one embodiment, the invention comprises a nanoparticle comprising a polymer and molecule of the general formula: Targeting Molecule—Polyethylene Glycol—Amphiphilic Component, wherein "—" is a covelant bond and wherein the nanoparticle diameter is between 40-80 nm and wherein the ratio of lecithin to polymer is between 14:1 and 34:1 by weight.

In another embodiment, the nanoparticle of the invention does not contain PEG.

The nanoparticles of the invention comprise an amphiphilic component. The amphiphilic component can form a layer around the outside of the nanoparticle, or disposed within the polymeric matrix of the nanoparticle. The amphiphilic component can exist as a continuous or discontinuous layer in the nanoparticle. As used herein, "discontinuous layer" refers to the fact that the layer can exists over a portion (or portions) of the nanoparticle.

Figure 12:
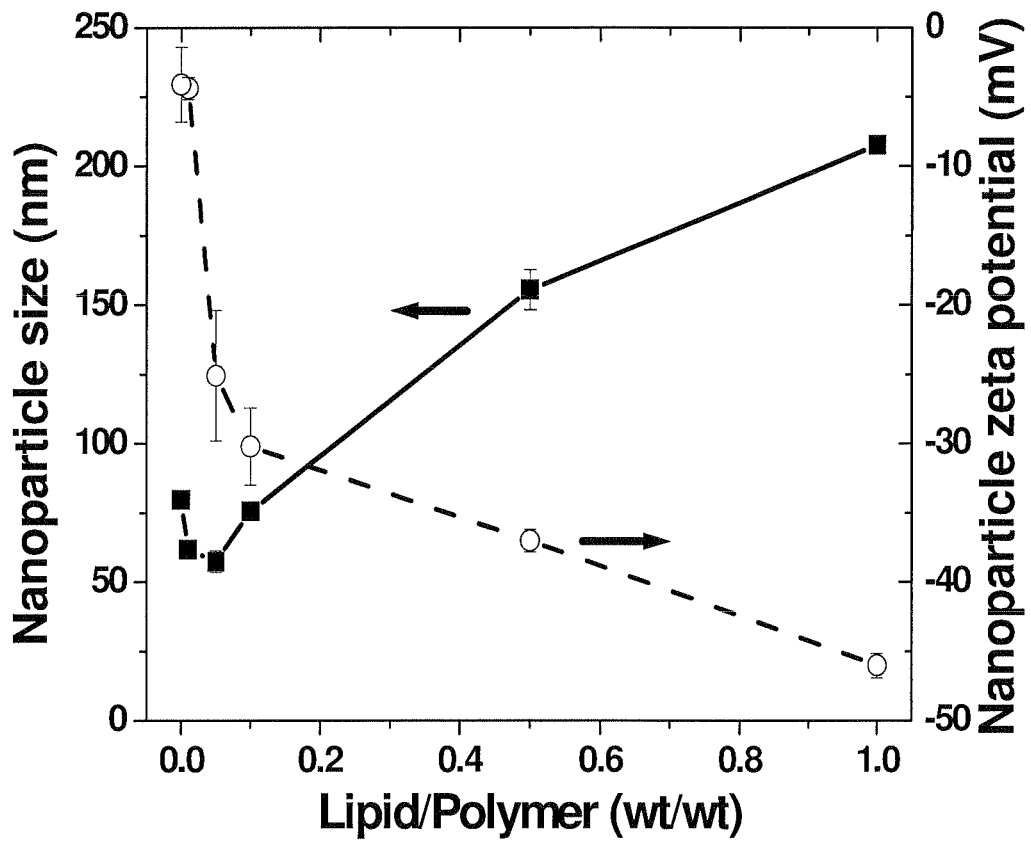
FIG. 12 demonstrates the effects of the ratio of lipid to polymer weight ratio on size and surface zeta potential on the amphiphilic layer-protected polymeric nanoparticles of the invention.

As shown in FIG. 12, as the ratio of amphiphilic component (e.g., lipid) to polymeric component is increased, the size of the nanoparticles increases. Additionally, as the ratio of amphiphilic component (e.g., lipid) to polymeric component is increased, the surface zeta potential decreases. In general, the nanoparticles of the present invention are about 40 nm to about 500 nm in size. In one embodiment, the nanoparticles of the invention are less than or equal to about 90 nm in size, e.g., about 40 nm to about 80 nm, e.g., about 40 nm to about 60 nm. Because the nanoparticles of the invention can be less than 90 nm in size, liver uptake by the subject is reduced, thereby allowing longer circulation in the bloodstream.

In one embodiment, a nanoparticle of this invention is between 40 nm and 80 nm in diameter and contains an amphiphilic component to polymer ratio of between 14:1 to 34:1. As discussed herein, the concentration of lipid in the nanoparticle will effect the size of the nanoparticle. Thus, in one embodiment, a nanoparticle that is approximately 10% to 40% lipid (by weight) will have a corresponding size of about 90 nm to about 40 nm.

The nanoparticles of the invention also have a surface zeta potential ranging from about −80 mV to 50 mV. Zeta potential is a measurement of surface potential of a particle. In some embodiments, the particles have a zeta potential ranging between 0 mV and −50 mV, e.g., between −1 mV and −50 mV. In some embodiments, the particles have a zeta potential ranging between −1 mV and −25 mV. In some embodiments, the particles have a zeta potential ranging between −1.1 mV and −10 mV.

In some embodiments, a therapeutic agent can be associated with the polymeric matrix. In some embodiments, the therapeutic agent can be associated with the surface of, encapsulated within, surrounded by, and/or dispersed throughout the polymeric matrix.

Such a nanoparticle is shown as a non-limiting example in FIG. 1. In this figure, two polymers and an amphiphilic component form a nanoparticle. The nanoparticle includes a biodegradable polymeric material (e.g., PLGA) that will form the polymeric matrix core of the nanoparticle, as well as a stealth polymer (e.g., PEG). The nanoparticle also includes an amphiphilic compound (e.g., a lipid, e.g., lecithin) dispersed within the biodegradable polymer and the stealth polymer. The polymer forming the stealth material includes an aptamer for targeting purposes. In some cases, as shown here, the targeting moiety (e.g., aptamer) is covalently conjugated to the stealth polymer (e.g., PEG). The non-limiting example in FIG. 1 shows a nanoparticle that is completely surrounded by an amphiphilic layer. It should be noted that the amphipilic layer-protected nanoparticles of the invention can be surrounded by a continuous layer of amphiphilic compound, or, alternatively, only partially surrounded by such a layer (i.e., a discontinuous layer). The amount of amphiphilic component in the nanoparticle can be adjusted by the user by altering the ratio of amphiphilic component to polymer when preparing the nanoparticle. As discussed herein, this ratio can be altered by the user to adjust the properties of the nanoparticles of the invention, such as, but not limited to, size and zeta potential.

It should be noted that not all of the stealth polymer is shown conjugated to a targeting moiety. By controlling the ratio of the polymer matrix to the targeting moiety, particles having different properties may be formed, and in some cases, libraries of such particles may be formed.

As is also shown in the non-limiting example shown in FIG. 1, contained within the center of the nanoparticle is a therapeutic agent. In some cases, the therapeutic agent may be contained within the particle due to hydrophobic effects. For instance, the interior of the particle may be relatively hydrophobic with respect to the surface of the particle, and the drug may be a hydrophobic drug that associates with the relatively hydrophobic center of the particle. In one embodiment, the therapeutic agent is associated with the surface of, encapsulated within, surrounded by, or dispersed throughout the nanoparticle. In another embodiment, the therapeutic agent is encapsulated within the hydrophobic core of the nanoparticle.

In one embodiment, upon being administered to a subject, the amphipilic layer of the nanoparticle of the invention can degrade, such that the polymer core is eventually "unshielded." Such a process, particularly when occurring after penetration into target tissue, can lead to more efficient delivery of the therapeutic agent, thereby affording an enhanced therapeutic effect.

Polymers

A wide variety of polymers and methods for forming particles therefrom are known in the art of drug delivery. In some embodiments of the invention, the matrix of a particle comprises one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples of biopolymers include peptides or proteins (i.e., polymers of various amino acids), or nucleic acids such as DNA or RNA. In some cases, additional moieties may also be present in the polymer, for example biological moieties such as those described below.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Various embodiments of the present invention are directed to copolymers, which, in particular embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers.

For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties). Alternatively, as described below, a copolymer can be formed using a lipid linker (e.g., DSPE).

In one set of embodiments, a polymer (e.g., copolymer, e.g., block copolymer) of the present invention includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the nanoparticles of the present invention can be "non-immunogenic." The term "non-immunogenic" as used herein refers to endogenous growth factor in its native state which normally elicits no, or only minimal levels of, circulating antibodies, T-cells, or reactive immune cells, and which normally does not elicit in the individual an immune response against itself.

It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, PLGA, polycaprolactone, or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly(serine ester), poly(4-hydroxy-L-proline ester), poly[a-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In particular embodiments, by optimizing the ratio of lactic acid to glycolic acid monomers in the polymer of the nanoparticle (e.g., the PLGA block copolymer or PLGA-PEG block copolymer), nanoparticle parameters such as water uptake, therapeutic agent release (e.g., "controlled release") and polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7), polyethylene imine) (PEI; Boussif et al, 1995, *Proc. Natl. Acad. Sci., USA*, 1995, 92:7297), and poly(amidoamine) dendrimers (Kukowska-Latallo et al., 1996, *Proc. Natl. Acad. Sci., USA*, 93:4897; Tang et al., 1996, *Bioconjugate Chem.*, 7:703; and Haensler et al., 1993, *Bioconjugate Chem.*, 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules*, 32:3658; Barrera et al., 1993, *J. Am. Chem. Soc.*, 115:11010; Kwonef al, 19%9, *Macromolecules*, 22325Q-, Urn et al., 1999, *J. Am. Chem. Soc.*, 121:5633; and Zhou et al, 1990, *Macromolecules*, 23:3399). Examples of these polyesters include poly(L-lactide-co-L-lysine) (Barrera et al, 1993, *J. Am. Chem. Soc.*, 115:11010), poly(serine ester) (Zhou et al., 1990, *Macromolecules*, 23:3399), poly(4-hydroxy-L-proline ester) (Putnam et al., 1999, *Macromolecules*, 32:3658; and Lim et al., 1999, *J. Am. Chem. Soc.*, 121:5633). Poly(4-hydroxy-L-proline ester) was demonstrated to condense plasmid DNA through electrostatic interactions, and to mediate gene transfer (Putnam et al, 1999, *Macromolecules*, 32:3658; and Lim et al., 1999, *J. Am. Chem. Soc.*, 121:5633). These new polymers are less toxic than poly(lysine) and PEI, and they degrade into non-toxic metabolites.

A polymer (e.g., copolymer, e.g., block copolymer) containing poly(ethylene glycol) repeat units is also referred to as a "PEGylated" polymer. Such polymers can control inflammation and/or immunogenicity (i.e., the ability to provoke an immune response) and/or lower the rate of clearance from the circulatory system via the reticuloendothelial system, due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly (ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether).

In a particular embodiment, the molecular weight of the polymers of the nanoparticles of the invention are optimized for effective treatment of diseases, e.g., cancer. For example, the molecular weight of the polymer influences nanoparticle degradation rate (particularly when the molecular weight of a biodegradable polymer is adjusted), solubility, water uptake, and drug release kinetics (e.g. "controlled release"). As a further example, the molecular weight of the polymer can be adjusted such that the nanoparticle biodegrades in the subject being treated within a reasonable period of time (ranging from a few hours to 1-2 weeks, 3-4 weeks, 5-6 weeks, 7-8 weeks, etc.). In particular embodiments of a nanoparticle comprising a copolymer of PEG and PLGA, the PEG has a molecular weight of 1,000-20,000, e.g., 5,000-20,000, e.g., 10,000-20,000, and the PLGA has a molecular weight of 5,000-100,000, e.g., 20,000-70,000, e.g., 20,000-50,000.

In another embodiment, the invention provides an amphiphilic layer-protected nanoparticle, and methods of making the nanoparticle, wherein one polymer of the polymeric matrix (e.g., PEG), is conjugated to a lipid that will self assemble with another polymer (e.g., PLGA), such that the polymers of the polymeric matrix are not covalently bound, but are bound through self-assembly. "Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. The lipid that is used for self-assembly of the polymers is in addition to the amphiphilic component of the nanoparticle.

In certain embodiments, the polymers of the nanoparticles may be conjugated to a lipid, i.e., a lipid in addition to the amphiphilic component of the nanoparticle of the invention. The polymer may be, for example, a lipid-terminated PEG. The present invention also provides methods for forming amphiphilic-protected nanoparticles with a lipid-terminated PEG. For example, such a method comprises providing a first polymer that is reacted with a lipid, to form a polymer/lipid conjugate. The polymer/lipid conjugate is then reacted with a targeting moiety to prepare a targeting moiety-bound polymer/lipid conjugate; and mixing the ligand-bound polymer/lipid conjugate with a second, non-functionalized polymer, an amphiphilic component, and a therapeutic agent; such that an amphiphilic layer-protected nanoparticle is formed. In certain embodiments, the first polymer is PEG, such that a lipid-terminated PEG is formed. The lipid-terminated PEG can then, for example, be mixed with PLGA to form a nanoparticle.

As described above, the lipid portion of the polymer can be used for self assembly with another polymer, facilitating the formation of a nanoparticle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid, i.e., the lipid in addition to the amphiphilic component of the nanoparticle of the invention, is of the Formula I:

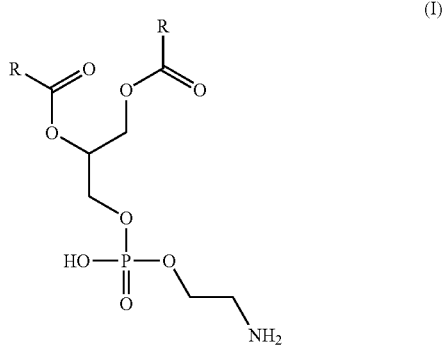

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al, 2001, *J. Am. Chem. Soc.*, 123:9480; Lim et al., 2001, *J. Am. Chem. Soc.*, 123:2460; Langer, 2000, *Ace. Chem. Res.*, 33:94; Langer, 1999, *J. Control. Release*, 62:7; and Uhrich et al., 1999, *Chem. Rev.*, 99:3181). More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al, 1997, *Nature*, 390:386; and in U.S. Pat. Nos. 6,506,577, 6,632,922, 6,686,446, and 6,818,732.

Therapeutic Agents

In still another set of embodiments, the amphiphilic protected nanoparticle of the present invention includes a therapeutic agent, i.e., an agent that has a therapeutic or prophylactic effect when given to a subject. Examples of therapeutic moieties to be used with the nanoparticles of the present invention include antineoplastic or cytostatic agents or other agents with anticancer properties, or a combination thereof.

For instance, the targeting moiety may target or cause the particle to become localized at specific portions within a subject, and the therapeutic agent may be delivered to those portions. In a particular embodiment, the drug or other payload is released in a controlled release manner from the particle and allowed to interact locally with the particular targeting site (e.g., a tumor). The term "controlled release" (and variants of that term) as used herein (e.g., in the context of "controlled-release system") is generally meant to encompass release of substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

In one set of embodiments, the therapeutic agent is a drug or a combination of more than one drug. Such particles may be useful, for example, in embodiments where a targeting moiety may be used to direct a particle containing a drug to a particular localized location within a subject, e.g., to allow localized delivery of the drug to occur. Exemplary therapeutic agents include chemotherapeutic agents such as doxorubicin (adriamycin), gemcitabine (gemzar), daunorubicin, procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11,10-hydroxy-7-ethylcamptothecin (SN38), dacarbazine, S—I capecitabine, ftorafur, 5' deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxy-camptothecin, karenitecin, 9-nitrocamptothecin, TAS103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

Suitable non-genetic therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, and (ff) phospholipids including phosphorylcholine, phosphatidylinositol and phosphatidylcholine.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Suitable genetic therapeutic agents for use in connection with the present invention include anti-sense DNA and RNA as well as DNA coding for the various proteins (as well as the proteins themselves) and may be selected, for example, from one or more of the following: (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Further therapeutic agents, not necessarily exclusive of those listed above, have been identified as candidates for vascular treatment regimens, for example, as agents targeting restenosis (anti-restenotic agents). Suitable agents may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD (orgotein), SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic for the practice of the present invention may be selected from suitable therapeutic agents disclosed in U.S. Pat. No. 5,733,925 to Kunz.

Non-limiting examples of potentially suitable drugs include anti-cancer agents, including, for example, docetaxel, mitoxantrone, and mitoxantrone hydrochloride. In another embodiment, the payload may be an anti-cancer drug such as 20-epi-1, 25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In another embodiment, the nanoparticles of the invention can be used to treat vulnerable plaque in a subject in need thereof. In particular, the drug associated with, i.e., encapsulated within, the nanoparticle of the invention is a biologically active agent used to stabilize a vulnerable plaque. Such agents are described in U.S. Pat. No. 7,008,411, which is incorporated herein by reference in its entirety.

In another embodiment, the nanoparticles of the invention can be used to treat restenosis or atherosclerosis in a subject in need thereof. Restenosis is the reobstruction of an artery following interventional procedures such as balloon angioplasty or stenting.

In one embodiment, when the targeting moiety is a peptide that targets tissue basement membrane (e.g., the basement membrane of a blood vessel), such as CREKA (SEQ ID NO: 2), therapeutic or biologically active agents can be released by the nanoparticles of the invention to induce therapeutic angiogenesis, which refers to the processes of causing or inducing angiogenesis and arteriogenesis, either downstream, or away from the vulnerable plaque. Arteriogenesis is the enlargement of pre-existing collateral vessels. Collateral vessels allow blood to flow from a well-perfused region of the vessel into an ischemic region (from above an occlusion to downstream from the occlusion). Angiogenesis is the promotion or causation of the formation of new blood vessels downstream from the ischemic region. Having more blood vessels (e.g., capillaries) below the occlusion may provide for less pressure drop to perfuse areas with severe narrowing caused by a thrombus. In the event that an occlusive thrombus occurs in a vulnerable plaque, the myocardium perfused by the affected artery is salvaged. Representative therapeutic or biologically active agents include, but are not limited to, proteins such as vascular endothelial growth factor (VEGF) in any of its multiple isoforms, fibroblast growth factors, monocyte chemoatractant protein 1(MCP-1), transforming growth factor alpha (TGF-alpha), transforming growth factor beta (TGF-beta) in any of its multiple isoforms, DEL-1, insulin like growth factors (IGF), placental growth factor (PLGF), hepatocyte growth factor (HGF), prostaglandin E1(PG-E1), prostaglandin E2(PG-E2), tumor necrosis factor alpha (TNF alpha), granulocyte stimulating growth factor (G-CSF), granulocyte macrophage colony-stimulating growth factor (GM-CSF), angiogenin, follistatin, and proliferin, genes encoding these proteins, cells transfected with these genes, pro-angiogenic peptides such as PR39 and PR11, and pro-angiogenic small molecules such as nicotine. The nanoparticles of the invention may also include lipid lowering agents (e.g., hydroxy-methylglutaryl coenzyme A (HMG CoA) reductase inhibitors, statins, niacin, bile acid resins, and fibrates), antioxidants (e.g., vitamin E ($\alpha$-tocopherol), vitamin C, and $\beta$-carotene supplements), extracellular matrix synthesis promoters, inhibitors of plaque inflammation and extracellular degradation, estradiol drug classes and its derivatives.

In some cases, the interior of the particle is more hydrophobic than the surface of the particle. For instance, the interior of the particle may be relatively hydrophobic with respect to the surface of the particle, and a therapeutic agent or drug may be hydrophobic, and readily associates with the relatively hydrophobic center of the particle. The drug or other payload may thus be contained within the interior of the particle, which may thus shelter it from the external environment surrounding the particle (or vice versa). For instance, a drug or other payload contained within a particle administered to a subject will be protected from a subject's body, and the body will also be isolated from the drug. A targeting moiety present on the surface of the particle may allow the particle to become localized at a particular targeting site, for instance, a tumor, a disease site, a tissue, an organ, a type of cell, etc. The drug or other payload may then, in some cases, be released from the particle and allowed to interact locally with the particular targeting site.

Other therapeutic agents to be delivered in accordance with the present invention include, but are not limited to, nucleic acids (e.g., siRNA, RNAi, and mircoRNA agents), proteins (e.g. antibodies), peptides, lipids, carbohydrates, hormones, metals, radioactive elements and compounds, vaccines, immunological agents, etc., and/or combinations thereof. In some embodiments, the agent to be delivered is an agent useful in the treatment of cancer (e.g., prostate cancer).

Targeting Moieties

In yet another set of embodiments a polymeric conjugate of the present invention includes a targeting moiety, i.e., a moiety able to bind to or otherwise associate with a biological entity, for example, a membrane component, a cell surface receptor, prostate specific membrane antigen, or the like. For example, a targeting portion may cause the particles to become localized to a tumor, a disease site, a tissue, an organ, a type of cell, etc. within the body of a subject, depending on the targeting moiety used. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

The targeting moiety (e.g., an aptamer) can be covalently bonded the polymeric matrix and/or the amphiphilic component of the nanoparticle. In some embodiments, the targeting moiety can be covalently associated with the surface of a polymeric matrix (e.g., PEG). In some embodiments, covalent association is mediated by a linker. In some embodiments, the therapeutic agent can be associated with the surface of, encapsulated within, surrounded by, and/or dispersed throughout the polymeric matrix.

A targeting moiety may be a nucleic acid, polypeptide, glycoprotein, carbohydrate, lipid, etc. For example, a targeting moiety can be a nucleic acid targeting moiety (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain targeting moieties can be identified, e.g., using procedures such as phage display. This widely used technique has been used to identify cell specific ligands for a variety of different cell types.

In some embodiments, targeting moieties bind to an organ, tissue, cell, extracellular matrix component, and/or intracellular compartment that is associated with a specific developmental stage or a specific disease state. In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In certain specific embodiments, a target is a tumor marker. In some embodiments, a tumor marker is an antigen that is present in a tumor that is not present in normal tissue. In some embodiments, a tumor marker is an antigen that is more prevalent in a tumor than in normal tissue. In some embodiments, a tumor marker is an antigen that is more prevalent in malignant cancer cells than in normal cells.

In some embodiments, a target is preferentially expressed in tumor tissues versus normal tissues. For example, when compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al., 1997, *Clin. Cancer Res.*, 3:81).

In some embodiments, inventive targeted particles comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

In some embodiments, the targeting moieties are covalently associated with the nanoparticle. In some embodiments, covalent association is mediated by a linker.

Nucleic Acid Targeting Moieties

As used herein, a "nucleic acid targeting moiety" is a nucleic acid that binds selectively to a target. In some embodiments, a nucleic acid targeting moiety is a nucleic acid that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

One of ordinary skill in the art will recognize that any aptamer that is capable of specifically binding to a target can be used in accordance with the present invention. In some embodiments, aptamers to be used in accordance with the present invention may target cancer-associated targets. In some embodiments, aptamers to be used in accordance with the present invention may target tumor markers.

In certain embodiments, aptamers to be used in accordance with the present invention may target prostate cancer associated antigens, such as PSMA. Exemplary PSMA-targeting aptamers to be used in accordance with the present invention include, but are not limited to, the A10 aptamer, having a nucleotide sequence of 5'-GGGAGGACGAUGCG-GAUCAGCCAUGUUUACGUCACUCCUUGUCAAU CCUCAUCGGCAGACGACUCGCCCGA-3' (SEQ ID NO: 5) (Lupold et al, 2002, Cancer Res,, 62:4029), the A9 aptamer, having nucleotide sequence of 5'-GGGAGGAC-GAUGCGGACCGAAAAAGACCUGACUUC-UAUACUAAGUC UACGUUCCCAGACGACUCGC-CCGA-3' (SEQ ID NO: 6) (Lupold et al, 2002, Cancer Res., 62:4029; and Chu et at, 2006, Nuc. Acid Res., 34:e73), derivatives thereof, and/or characteristic portions thereof.

In some embodiments, a nucleotide sequence that is homologous to a nucleic acid targeting moiety may be used in accordance with the present invention. In some embodiments, a nucleotide sequence is considered to be "homologous" to a nucleic acid targeting moiety if it comprises fewer than 30, 25, 20, 15, 10, 5, 4, 3, 2, or 1 nucleic acid substitutions relative to the aptamer. In some embodiments, a nucleotide sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% identical. In some embodiments, a nucleic acid sequence is considered to be 35%, 40%, 45%, 50%, 55%, 60%, 65%, 70%, 75%, 80%, 85%, 90%, 95%, or 99% similar. Nucleic acids of the present invention (including nucleic acid targeting moieties and/or functional RNAs to be delivered, e.g., RNAi agents, ribozymes, tRNAs, etc., described in further detail below) may be prepared according to any available technique including, but not limited to, chemical synthesis, enzymatic synthesis, enzymatic or chemical cleavage of a longer precursor, etc. Methods of synthesizing RNAs are known in the art (see, e.g., Gait, M.J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005).

The nucleic acid that forms the nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g., the dissociation constant of the nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) *Antisense Drug Technology: Principles, Strategies, and Applications* ($1^{st}$ ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, $NH_2$, NHR, $NR_2$ or CN, wherein R is $C_1$-$C_6$ alkyl, alkenyl, or alkynyl, and halo is F, Cl, Br or I. Examples of modified linkages include phosphorothioate and 5'-N-phosphoramidite linkages.

Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 0(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and S'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of an aptamer such that the ability of the aptamer to specifically bind to the aptamer target is not substantially affected. The modified region may be at the 5'-end and/or the 3'-end of one or both strands. For example, modified aptamers in which approximately 1-5 residues at the 5' and/or 3' end of either of employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic agent, improved specific binding of an aptamer to an aptamer target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the aptamer are inverted to yield a such as a 3'-3' linkage or a 5'-5' linkage.

In some embodiments, nucleic acids in accordance with the present invention are not synthetic, but are naturally-occurring entities that have been isolated from their natural inments.

Protein Targeting Moieties

In some embodiments, a targeting moiety in accordance with the present invention may be a protein or peptide. In certain embodiments, peptides range from about 5 to 100, 10 to 75, 15 to 50, or 20 to 25 amino acids in size. In some embodiments, a peptide sequence a random arrangement of amino acids. In a particular embodiment, the targeting peptide to be used with the nanoparticles of the invention is less than 8 amino acids in length.

The terms "polypeptide" and "peptide" are used interchangeably herein, with "peptide" typically referring to a polypeptide having a length of less than about 100 amino acids. Polypeptides may contain L-amino acids, D-amino acids, or both and may contain any of a variety of amino acid modifications or analogs known in the art. Useful modifications include, e.g., terminal acetylation, amidation, lipidation, phosphorylation, glycosylation, acylation, farnesylation, sulfation, etc.

In another embodiment, the targeting moiety can be a targeting peptide or targeting peptidomimetic has a length of at most 50 residues. In a further embodiment, a nanopaticle of the invention contains a targeting peptide or peptidomimetic that includes the amino acid sequence AKERC (SEQ ID NO: 1), CREKA (SEQ ID NO: 2), ARYLQKLN (SEQ ID NO: 3) or AXYLZZLN (SEQ ID NO: 4), wherein X and Z are variable amino acids, or conservative variants or peptidomimetics thereof. In particular embodiments, the targeting moiety is a peptide that includes the amino acid sequence AKERC (SEQ ID NO: 1), CREKA (SEQ ID NO: 2), ARYLQKLN (SEQ ID NO: 3) or AXYLZZLN (SEQ ID NO: 4), wherein X and Z are variable amino acids, and has a length of less than 20, 50 or 100 residues. The CREKA (SEQ ID NO: 2) peptide is known in the art, and is described in U.S. Patent Application No. 2005/0048063, which is incorporated herein by reference in its entirety. The octapeptide AXYLZZLN (SEQ ID NO: 4) is described in Dinkla et al., The Journal of Biological Chemistry, Vol. 282, No. 26, pp. 18686-18693, which is incorporated herein by reference in its entirety.

In one embodiment, the targeting moiety is an isolated peptide or peptidomimetic that has a length of less than 100 residues and includes the amino acid sequence CREKA (Cys Arg Glu Lys Ala) (SEQ ID NO: 2) or a peptidomimetic thereof. Such an isolated peptide-or peptidomimetic can have, for example, a length of less than 50 residues or a length of less than 20 residues. In particular embodiments, the invention provides a peptide that includes the amino acid sequence CREKA (SEQ ID NO: 2) and has a length of less than 20, 50 or 100 residues.

Moreover, the authors of The Journal of Biological Chemistry, Vol. 282, No. 26, pp. 18686-18693 describe a binding motif in streptococci that forms an autoantigenic complex with human collagen IV. Accordingly, any peptide, or conservative variants or peptidomimetics thereof, that binds or forms a complex with collagen IV, or the targets tissue basement membrane (e.g., the basement membrane of a blood vessel), can be used as a targeting moiety for the nanoparticles of the invention.

Exemplary proteins that may be used as targeting moieties in accordance with the present invention include, but are not limited to, antibodies, receptors, cytokines, peptide hormones, proteins derived from combinatorial libraries (e.g. avimers, affibodies, etc.), and characteristic portions thereof.

In some embodiments, any protein targeting moiety can be utilized in accordance with the present invention. To give but a few examples, IL-2, transferrin, GM-CSF, a-CD25, a-CD22, TGF-a, folic acid, a-CEA, a-EpCAM scFV, VEGF, LHRH, bombesin, somatostin, Gal, α-GD2, α-EpCAM, α-CD20, M0v19, scFv, α-Her-2, and α-CD64 can be used to target a variety of cancers, such as lymphoma, glioma, leukemia, brain tumors, melanoma, ovarian cancer, neuroblastoma, folate receptor-expressing tumors, CEA-expressing tumors, EpCAM-expressing tumors, VEGF-expressing tumors, etc. (Eklund et al, 2005, *Expert Rev. Anticancer Ther.*, 5:33; Kreitman et al., 2000, *J. Clin. OncoL*, 18:1622; Kreitman et al, 2001, *N. Engl. J. Med*, 345:241; Sampson et al., 2003, J. *Neurooncol*, 65:27; Weaver et al., 2003, *J. Neurooncol*, 65:3; Leamon et al., 1993, *J. Biol. Chem.*, 268:24847; Leamon et al., 1994, *J. Drug Target.*, 2:101; Atkinson et al., 2001, *J. Biol. Chem.*, 276:27930; Frankel et al., 2002, *Clin. Cancer Res.*, 8:1004; Francis et al, 2002, *Br. J. Cancer*, 87:600; de Graaf et al., 2002, *Br. J. Cancer*, 86:811; Spooner et al., 2003, *Br. J. Cancer*, 88:1622; Liu et al, 1999, *J. Drug Target.*, 7:43; Robinson et al, 2004, *Proc. Natl. Acad. Sci., USA*, 101:14527; Sondel et al, 2003, *Curr. Opin. Investig. Drugs*, 4:696; Connor et al., 2004, *J. Immunother.*, 27:211; Gillies et al, 2005, *Blood*, 105:3972; Melani et al, 1998, *Cancer Res.*, 58:4146; Metelitsa et al, 2002, *Blood*, 99:4166; Lyu et al, 2005, *Mol Cancer Ther.*, 4:1205; and Hotter et al, 2001, *Blood*, 97:3138).

In some embodiments, protein targeting moieties can be peptides. One of ordinary skill in the art will appreciate that any peptide that specifically binds to a desired target can be used in accordance with the present invention. In some embodiments, peptides targeting tumor vasculature are antagonists or inhibitors of angiogenic proteins that include VEGFR (Binetruy-Tournaire et al, 2000, EMBO J, 19:1525), CD36(Reiher et al, 2002, Int. *J Cancer*, 98:682) and Kumar et al, 2001, *Cancer Res.*, 61:2232) aminopeptidase N (Pasqualini et al, 2000, *Cancer Res.*, 60:722), and matrix metalloproteinases (Koivunen et al., 1999, *Nat. Biotechnol*, 17:768). For instance, ATWLPPR (SEQ ID NO: 7) peptide is a potent antagonist of VEGF (Binetruy-Tournaire et al, 2000, EMBO J., 19:1525); thrombospondin-1(TSP-1) mimetics can induce apoptosis in endothelial cells (Reiher et al , 2002, Int. J Cancer, 98:682); ROD-motif mimics (e.g. cyclic peptide ACDCRGDCFCG (SEQ ID NO: 8) and ROD peptidomimetic SCH 221153) block integrin receptors (Koivunen et al, 1995, Biotechnology (NY), 13:265; and Kumar et al, 2001, Cancer Res., 61:2232); NOR-containing peptides (e.g. cyclic CNGRC (SEQ ID NO: 8)) inhibit aminopeptidase N (Pasqualini et al, 2000, Cancer Res., 60:722); and cyclic peptides containing the sequence of HWGF (SEQ ID NO: 9) (e.g. CTTHWGFTLC (SEQ ID NO: 10)) selectively inhibit MMP-2 and MMP-9(Koivunen et al., 1999, Nat. Biotechnol., 17:768); and a LyP-1 peptide has been identified (CGNKRTRGC (SEQ ID NO: 11)) which specifically binds to tumor lymphatic vessels and induces apoptosis of endothelial cells (Laakkonen et al, 2004, Proc. Nail Acad. Sci., USA, 101:9381).

In some embodiments, peptide targeting moieties include peptide analogs that block binding of peptide hormones to receptors expressed in human cancers (Bauer et al., 1982, Life Sci., 31:1133). Exemplary hormone receptors (Reubi et al, 2003, Endocr. Rev., 24:389) include (1) somatostatin receptors (e.g. octreotide, vapreotide, and lanretode) (Froidevaux et al, 2002, Biopolymers, 66:161); (2) bombesin/gastrin-releasing peptide (GRP) receptor (e.g. RC-3940 series) (Kanashiro et al, 2003, Proc. Natl. Acad. Sci., USA, 100:15836); and (3) LHRH receptor (e.g. Decapeptyf, Lupron®, Zoladex®, and Cetrorelix®) (Schally et al., 2000, Prostate, 45:158).

In some embodiments, peptides that recognize IL-11 receptor-a can be used to target cells associated with prostate cancer tumors (see, e.g., U.S. Patent Publication 2005/0191294).

In some embodiments, a targeting moiety may be an antibody and/or characteristic portion thereof. The term "antibody" refers to any immunoglobulin, whether natural or wholly or partially synthetically produced and to derivatives thereof and characteristic portions thereof. An antibody may be monoclonal or polyclonal. An antibody may be a member of any immunoglobulin class, including any of the human classes: IgG, IgM, IgA, IgD, and IgE. One of ordinary skill in the art will appreciate that any antibody that specifically binds to a desired target can be used in accordance with the present invention.

In some embodiments, antibodies that recognize PSMA can be used to target cells associated with prostate cancer tumors. Such antibodies include, but are not limited to, scFv antibodies A5, GO, G1, G2, and G4 and mAbs 3/B7, 3/F11, 3/A12, K7, K12, and D20 (Elsasser-Beile et al, 2006, Prostate, 66:1359); mAbs E99, J591, J533, and J415 (Liu et al, 1997, Cancer Res., 57:3629; Liu et al, 1998, Cancer Res., 58:4055; Fracasso et al., 2002, Prostate, 53:9; McDevitt et al, 2000, Cancer Res., 60:6095; McDevitt et al., 2001, Science, 294:1537; Smith-Jones et al, 2000, Cancer Res., 60:5237; Vallabhajosula of al., 2004, Prostate, 58:145; Bander er a/., 2003, J. C/ro/., 170:1717; Patri et al., 2004, Bioconj. Chem., 15:1174; and U.S. Pat. No. 7,163,680); mAb 7E11-05.3 (Horoszewicz et al., 1987, Anticancer Res., 7:927); antibody 7E11 (Horoszewicz et al, 1987, Anticancer Res., 7:927; and U.S. Pat. No. 5,162,504); and antibodies described in Chang et al, 1999, Cancer Res., 59:3192; Murphy et al., 1998, J. Urol, 160:2396; Grauer et al, 1998, Cancer Res., 58:4787; and Wang era/., 2001, M J. Cancer, 92:871. One of ordinary skill in the art will appreciate that any antibody that recognizes and/or specifically binds to PSMA may be used in accordance with the present invention.

In some embodiments, antibodies which recognize other prostate tumor-associated antigens are known in the art and can be used in accordance with the present invention to target cells associated with prostate cancer tumors (see, e.g., Vihko et al, 1985, Biotechnology in Diagnostics, 131; Babaian et al, 1987, J. Urol, 137:439; Leroy et al., 1989, Cancer, 64:1; Meyers et al, 1989, Prostate, 14:209; and U.S. Pat. Nos. 4,970,299; 4,902,615; 4,446,122 and Re 33,405; 4,862,851; 5,055,404). To give but a few examples, antibodies have been identified which recognize transmembrane protein 24P4C12 (U.S. Patent Publication 2005/0019870); calveolin (U.S. Patent Publications 2003/0003103 and 2001/0012890); L6 (U.S. Patent Publication 2004/0156846); prostate specific reductase polypeptide (U.S. Pat. No. 5,786,204; and U.S. Patent Publication 2002/0150578); and prostate stem cell antigen (U.S. Patent Publication 2006/0269557).

In some embodiments, protein targeting moieties that may be used to target cells associated with prostate cancer tumors include conformationally constricted dipeptide mimetics (Ding et al, 2004, Org. Lett., 6:1805).

As used herein, an antibody fragment (i.e., characteristic portion of an antibody) refers to any derivative of an antibody which is less than full-length. In general, an antibody fragment retains at least a significant portion of the full-length antibody's specific binding ability. Examples of antibody fragments include, but are not limited to, Fab, Fab", F(ab')$_2$, scFv, Fv, dsFv diabody, and Fd fragments.

An antibody fragment can be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multimolecular complex. A functional antibody fragment will typically comprise at least about 50 amino acids and more typically will comprise at least about 200 amino acids. In some embodiments, antibodies may include chimeric (e.g., "humanized") and single chain (recombinant) antibodies. In some embodiments, antibodies may have reduced effector functions and/or bispecific molecules. In some embodiments, antibodies may include fragments produced by a Fab expression library.

Single-chain Fvs (scFvs) are recombinant antibody fragments consisting of only the variable light chain (VL) and variable heavy chain (VH) covalently connected to one another by a polypeptide linker. Either VL or VH may comprise the NH2-terminal domain. The polypeptide linker may be of variable length and composition so long as the two variable domains are bridged without significant steric interference. Typically, linkers primarily comprise stretches of glycine and serine residues with some glutamic acid or lysine residues interspersed for solubility.

Diabodies are dimeric scFvs. Diabodies typically have shorter peptide linkers than most scFvs, and they often show a preference for associating as dimers.

An Fv fragment is an antibody fragment which consists of one VH and one VL domain held together by noncovalent interactions. The term "dsFv" as used herein refers to an Fv with an engineered intermolecular disulfide bond to stabilize the VH-VL pair.

A Fab' fragment is an antibody fragment essentially equivalent to that obtained by reduction of the disulfide bridge or bridges joining the two heavy chain pieces in the F(ab')$_2$ fragment. The Fab' fragment may be recombinantly produced.

A Fab fragment is an antibody fragment essentially equivalent to that obtained by digestion of immunoglobulins with an enzyme (e.g. papain). The Fab fragment may be recombinantly produced. The heavy chain segment of the Fab fragment is the Fd piece.

Carbohydrate Targeting Moieties

In some embodiments, a targeting moiety in accordance with the present invention may comprise a carbohydrate. To give but one example, lactose and/or galactose can be used for targeting hepatocytes.

In some embodiments, a carbohydrate may be a polysaccharide comprising simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucdronic acid, galactoronic acid, mannuronic acid, glucosamine, galatosatnine, and neuramic acid. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, algin and alginic acid, starch, chitin, heparin, konjac, glucommannan, pustulan, heparin, hyaluronic acid, curdlan, and xanthan.

In some embodiments, the carbohydrate may be aminated, carboxylated, and/or sulfated. In some embodiments, hydropbilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

Lipid Targeting Moieties

In some embodiments, a targeting moiety in accordance with the present invention may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

The targeting moiety can be conjugated to the polymeric matrix or amphiphilic component using any suitable conjugation technique. For instance, two polymers such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly (ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as an aptamer or peptide, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

Preparation of Amphiphilic Layer-Protected Polymeric Nanoparticles

Another aspect of the invention is directed to systems and methods of producing such amphiphilic layer-protected polymeric nanoparticles. In some embodiments, a solution containing a polymer is contacted with a liquid, such as an immiscible liquid, to form nanoparticles containing the polymeric conjugate.

As discussed, one aspect of the invention is directed to a method of developing nanoparticles with desired properties, such as desired chemical, biological, or physical properties. In one set of embodiments, the method includes producing libraries of nanoparticles having highly controlled properties, which can be formed by mixing together two or more polymers, as well as an amphiphilic component (e.g., lecithin) in different ratios. By mixing together two or more different polymers (e.g., homopolymers or copolymers) and an amphiphilic component in different ratios and producing particles from these components, particles having highly controlled properties may be formed. For example, one polymer (e.g., PEG) may include a targeting moiety (e.g., aptamer), while another polymer (e.g., PLGA) may be chosen for its biocompatibility and/or its ability to control immunogenicity of the resultant particle. These polymers can be combined with an amphiphilic component (e.g., lecithin) at a particular ratio to produce a nanoparticle with desired physical properties (e.g., drug release, size and zeta potential). For example, as described herein, by increasing the amount of amphiphilic component (e.g., lecithin) to polymeric component, nanoparticle size increases and zeta potential decreases.

In a certain embodiment, the nanoparticles of the invention can be prepared by dissolving the components of the nanoparticles (i.e., one or more polymers, an amphiphilic component, and a therapeutic agent), individually or combined, in one or more solvents to form one or more solutions. For example, a first solution comprising one or more of the components may be poured into a second solution comprising one or more of the components (at a suitable rate or speed). In some cases, nanoparticles can be formed as the first solution contacts the second solution, e.g., precipitation of the polymer upon contact causes the polymer to form nanoparticles. The control of such particle formation can be readily optimized by one of ordinary skill in the art using only routine experimentation.

In one set of embodiments, the nanoparticles are formed by providing one or more solutions comprising one or more polymers and amphiphilic components, and contacting the solutions with certain solvents to produce the particle. In a non-limiting example, a first polymer (e.g., a stealth polymer, e.g., PEG), is conjugated to a targeting moiety (e.g., an aptamer) to form a conjugate. The polymer of the conjugate is optionally conjugated to a lipid (e.g., DSPE) that can be used for self assembly with a second polymer. This polymer-targeting moiety conjugate (or polymer-targeting moiety-lipid conjugate) is added, in a water miscible solvent, to an amphiphilic component (e.g., lecithin). Separately, a second polymer (e.g., a biodegradable polymer, e.g., PLGA) and a therapeutic agent are dissolved in a partially water miscible organic solvent. The water miscible organic solvent and partially water miscible organic solvent solutions are then combined, forming the amphiphilic layer-protected polymeric nanoparticles of the invention. Once the solutions are combined, the formed nanoparticles can be exposed to further processing techniques to remove the solvents or purify the nanoparticles. Such further processing steps include, but are not limited to, dialyzation. For purposes of the aforementioned process, water miscible solvents include, but are not limited to, acetone, ethanol, methanol, and isopropyl alcohol; and partially water miscible organic solvents include, but are not limited to, acetonitrile, tetrahydrouran, ethyl acetate, isopropyl alcohol, isopropyl acetate or dimethylformamide.

Yet another aspect of the invention is directed to polymer particles having more than one polymer or macromolecule present, and libraries involving such polymers or macromolecules. For example, in one set of embodiments, the polymeric matrix of the amphiphilic layer-protected nanoparticles may contain more than one distinguishable polymer (e.g., multiple homopolymers, copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle, as well as control of the amount of amphiphilic component, e.g., lecithin, with respect to the amount of polymer(s), may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

Libraries of such particles may also be formed. For example, by varying the ratios of the amphiphilic component (e.g., lecithin) to the polymer component (e.g., PEG and/or PLGA), libraries of particles may be formed, which may be useful, for example, for screening tests, high-throughput assays, or the like. Entities within the library may vary by properties such as those described above, and in some cases, more than one property of the particles may be varied within the library. Accordingly, one embodiment of the invention is directed to a library of nanoparticles having different ratios of polymers with differing properties. The library may include any suitable ratio(s) of the polymers to the amphiphilic component. For example, in a particle having a polymer and an amphiphilic component, the polymer and amphiphilic component can present in a ratio of about 0.2:0.8, about 0.3:0.7, about 0.4:0.6, and about 1:1.

In some cases, a population of particles may be present. For example, a population of particles may include at least 20 particles, at least 50 particles, at least 100 particles, at least 300 particles, at least 1,000 particles, at least 3,000 particles, or at least 10,000 particles. Various embodiments of the present invention are directed to such populations of particles. For instance, in some embodiments, the particles may each be substantially the same shape and/or size ("monodisperse"). For example, the particles may have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater man the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

By creating a library of such particles, particles having any desirable properties may be identified. For example, properties such as surface functionality, surface charge, size, zeta ($\zeta$) potential, hydrophobicity, ability to control immunogenicity, and the like, may be highly controlled. For instance, a library of particles may be synthesized, and screened to identify the particles having a particular ratio of polymers that allows the particles to have a specific density of targeting moieties present on the surface of the particle. This allows particles having one or more specific properties to be prepared, for example, a specific size and a specific surface density of moieties, without an undue degree of effort. Accordingly, certain embodiments of the invention are directed to screening techniques using such libraries, as well as any particles identified using such libraries. In addition, identification may occur by any suitable method. For instance, the identification may be direct or indirect, or proceed quantitatively or qualitatively.

More generally, the polymers chosen to be used to create the library of particles may be any of a wide variety of polymers, such as described in detail below. Generally, two, three, four, or more polymers are mixed, in a wide range of ratios (e.g., each ranging from 0% to 100%), to form particles such as nanoparticles having different ratios of each of the polymers. The two or more polymers may be distinguishable in some fashion, e.g., having different polymeric groups, having the same polymeric groups but with different molecular weights, having some polymeric groups in common but having others that are different (e.g., one may have a polymeric group that the other does not have), having the same polymeric groups but in different orders, etc. The library of particles may have any number of members, for example, the library may have 2, 3, 5, 10, 30, 100, 300, 1000, 3000, 10,000, 30,000, 100,000, etc. members, which can be identified in some fashion. In some cases, the library may exist contemporaneously; for example, the library may be contained in one or more microtiter plates, vials, etc., or in some embodiments, the library may have include members created at different times.

The library of particles can then be screened in some fashion to identify those particles having one or more desired properties, for example, surface functionality, surface charge, size, zeta ($\zeta$) potential, hydrophobicity, ability to control immunogenicity, and the like. One or more of the polymers can be chosen to be biocompatible or biodegradable, and one or more of the polymers can be chosen to reduce immunogenicity. The nanoparticles within the library can comprise some or all of these polymers, in any suitable combination (including, but not limited to, combinations in which a first polymer comprises a targeting moiety and a second polymer does not contain any of these species).

The nanoparticles of the library can be comprised of a first biocompatible hydrophobic polymer, a biocompatible hydrophilic polymer, a targeting moiety (e.g., an aptamer), a lipid for self assembly of the two polymers, and an amphiphilc component. The targeting moiety can be covalently bonded to some or all of the hydrophilic polymer, such that the resulting nanoparticle is partially or completely surrounded by targeting moieties covalently bound to its surface. Nanoparticles with varying densities of targeting moieties can be achieved by altering the ratio of targeting moiety functionalized to non-functionalized hydrophilic polymer. As the amount of the functionalized hydrophilic polymer is increased, relative to the non-functionalized polymer, the amount of targeting moiety (e.g., an aptamer) present on the surface of the nanoparticle can be increased. Thus, any suitable concentration of moiety on the surface may be achieved simply by controlling the ratio of functionalized and non-functionalized polymers in the particles. Accordingly, such a library of particles may be useful in selecting or identifying particles having a particular functionality. The nanoparticle will also have a continuous or discontinuous amphiphilic layer (e.g., lecithin) surrounding or dispersed throughout the polymeric matrix.

Figure 2:
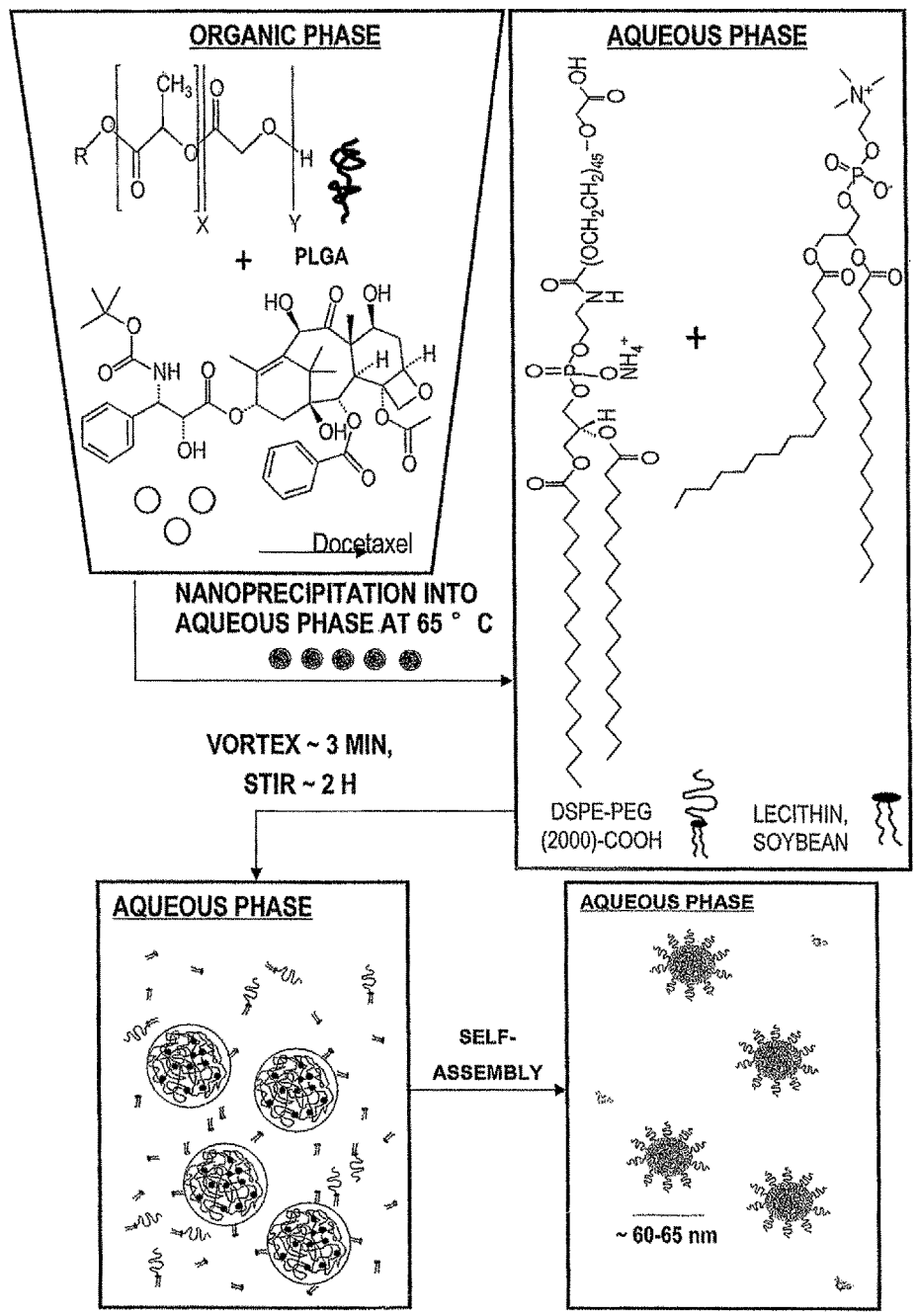
FIG. 2 shows a schematic illustration of an example of a synthesis procedure of an amphiphilic layer-protected polymeric nanoparticle of the invention.

FIG. 2 shows a schematic illustration of an example of a synthesis procedure of an amphiphilic layer-protected polymeric nanoparticle of the invention.

Methods of Treatment

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, the targeted nanoparticles of the invention can be used to treat cancer, e.g., prostate or breast cancer, and/or cancer cells, e.g., prostate or breast cancer cells in a subject in need thereof. In other embodiments, the targeted nanoparticles of the invention can be used to treat atherosclerotic plaques, restenosis, and atherosclerosis in a subject in need thereof.

The term "subject" is intended to include organisms, e.g., prokaryotes and eukaryotes, which are capable of suffering from or afflicted with a disease or disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a disease or disorder.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. breast or prostate cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. breast or prostate cancer) is provided. In some embodiments, particles to a subject in such amounts and for such time as is necessary to achieve the desired result (i.e., treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In other embodiments, the nanoparticles of the present invention can be used to inhibit the growth of cancer cells, e.g., prostate or breast cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

The present invention is also directed, in part, to the discovery that a collagen IV alpha-2 chain related polypeptide can act as a receptor for the CREKA (SEC) ID NO: 2) tumor targeting peptide. Collagens are a major component of the extracellular matrix (ECM), an interconnected molecular network providing mechanical support for cells and tissues and regulating biochemical and cellular processes such as adhesion, migration, gene expression and differentiation (see, e.g., U.S. Patent Application No. 2005/0048063, which is incorporated herein by reference in its entirety). In higher animals, at least 19 distinct collagen types differing in their higher order structures and functions have been identified based on the presence of the characteristic collagen triple-helix structure. The collagens are sometimes categorized into the fibrillar and nonfibrillar collagens. The fibrillar (interstitial) collagens include types I, II, III, V and XI, while the nonfibrillar collagens include types IV, VI, IX, X, XI, XII, XIV and XIII.

Targeting moieties useful in the invention include those which selectively target tumor vasculature and selectively bind non-helical collagen. Targeting moieties include those which selectively target to tumor vasculature and selectively bind collagen IV, and those which selectively target tumor vasculature and selectively bind denatured collagen IV in preference to native collagen IV. Such moieties include, but are not limited to, AKERC (SEQ ID NO: 1), CREKA (SEQ ID NO: 2), ARYLQKLN (SEQ ID NO: 3) or AXYLZZLN (SEQ ID NO: 4), wherein X and Z are variable amino acids. As such, the nanoparticles of the invention can be used for the treatment of cardiovascular related conditions, such as restenosis, vulnerable plaques and atherosclerosis in a subject in need thereof.

In a preferred embodiment, the nanoparticles of the invention can be delivered to or near a vulnerable plaque, particularly when the targeting moiety is a peptide that targets the tissue basement membrane (e.g., the basement membrane of a blood vessel) (e.g., CREKA (SEQ ID NO: 2)), using a medical device such as a needle catheter, drug eluding stent or stent graft. Such devices are well known in the art, and are described, for example, in U.S. Pat. No. 7,008,411, which is incorporated herein by reference in its entirety. In one embodiment, a drug eluting stent and/or needle catheter may be implanted at the region of vessel occlusion that may be upstream from a vulnerable plaque region. A medical device, such as a drug eluting stent, needle catheter, or stent graft may be used to treat the occlusive atherosclerosis (i.e., non-vulnerable plaque) while releasing the nanoparticle of the invention to treat a vulnerable plaque region distal or downstream to the occlusive plaque. The nanoparticle may be released slowly over time.

The nanoparticles of the invention can also be delivered to a subject in need thereof using the Genie™ balloon catheter available from Acrostak (http://www.acrostak.com/genie_en.htm). The nanoparticles of the invention can also be delivered to a subject in need thereof using delivery devices that have been developed for endovascular local gene transfer such as passive diffusion devices (e.g., double-occlusion balloon, spiral balloon), pressure-driven diffusion devices (e.g., microporous balloon, balloon-in-balloon devices, double-layer channeled perfusion balloon devices, infusion-sleeve catheters, hydrogel-coated balloons), and mechanically or electrically enhanced devices (e.g., needle injection catheter, iontophoretic electric current-enhanced balloons, stent-based system), or any other delivery system disclosed in Radiology 2003; 228:36-49, or Int J Nanomedicine 2007; 2(2):143-61, which are incorporated herein by reference in their entireties.

Pharmaceutical Compositions

As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes. In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the inventive conjugate with suitable non-irritating excipients or carriers such as cocoa butter, polyethylene glycol, or a suppository wax which are solid at ambient temperature but liquid at body temperature and therefore melt in the rectum or vaginal cavity and release the inventive conjugate.

Dosage forms for topical or transdermal administration of an inventive pharmaceutical composition include ointments, pastes, creams, lotions, gels, powders, solutions, sprays, inhalants, or patches. The inventive conjugate is admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive conjugates of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive conjugates in a proper medium. Absorption enhancers can also be used to increase the flux of the compound across the skin. The rate can be controlled by either providing a rate controlling membrane or by dispersing the inventive conjugates in a polymer matrix or gel.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive nanoparticles can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Ace. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive conjugates may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain embodiments, the adjuvant stimulates the immune response. Any adjuvant may be used in accordance with the present invention. A large number of adjuvant compounds is known in the art (Allison Dev. Biol. Stand. 92:3-11, 1998; Unkeless et al. Annu. Rev. Immunol. 6:251-281, 1998; and Phillips et al. Vaccine 10:151-158, 1992).

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the PSMA-targeted particle is chosen by the individual physician in view of the patient to be treated, in general, dosage and administration are adjusted to provide an effective amount of the PSMA-targeted particle to the patient being treated. As used herein, the "effective amount" of an PSMA-targeted particle refers to the amount necessary to elicit the desired biological response. As will be appreciated by those of ordinary skill in this art, the effective amount of PSMA-targeted particle may vary depending on such factors as the desired biological endpoint, the drug to be delivered, the target tissue, the route of administration, etc. For example, the effective amount of PSMA-targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles of the invention may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of naoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments.

The data obtained from cell culture assays and animal studies can be used in formulating a range of dosages for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the nanoparticle and the mode of use or administration. Suitable solvents for drug compositions are well known, for example as previously described, and are available in the literature. The solvent will depend on the nanoparticle and the mode of use or administration.

The invention also involves, in another aspect, promotion of the administration of any of the nanoparticles described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

The following examples are intended to illustrate certain embodiments of the present invention, but do not exemplify the full scope of the invention.

EXAMPLES

The invention is further illustrated by the following examples. The examples should not be construed as further limiting.

Example 1

Nanoparticle Preparation

In this example, the A10 RNA aptamer which binds to the Prostate Specific Membrane Antigen (PSMA) on the surface of prostate cancer cells is conjugated to DSPE (1,2-Distearoyl-sn-glycero-3-phosphoethanolamine)-PEG-COOH using EDC/NHS chemistry with a conjugate concentration of 0.7 mg/mL. 0.21 mg of this DSPE-PEG-Aptamer bioconjugate is mixed with 0.07 mg lecithin in 2 mL aqueous solution containing 4% ethanol. 1 mg poly(D,L-lactic-co-g!ycolic acid) (PLGA, Mw=100 kD) is dissolved in 1 mL tetrahydrofuran (THF) solvent, to which 5% docetaxel of the mass of PLGA is added. This PLGA solution is then mixed with the aqueous solution of lecithin/DSPE-PEG-Aptamer. These mixtures are vortexed for 3 minutes, followed by stirring for 2 hours. In order to remove all organic solvents, these mixtures are then dialyzed for another 4 hours against PBS buffer. This procedure would yield nanoparticles targeting to prostate cancer cells expressing PSMA antigens.

Example 2

Nanoparticle preparation

In a second embodiment, the peptide CREKA (SEQ ID NO: 2) is conjugated to DSPE-PEG-Maleimide before formulating nanoparticles using the same protocol of Example 1. This peptide will target the delivery and uptake of the nanoparticles to extracellular basement membranes which are exposed under the leaky endothelial layer covering atherosclerotic plaques.

Example 3

Nanoparticle Preparation

Using poly ($_{D,L}$lactic-co-glycolic acid) (PLGA) as a polymeric core, lecithin monolayer (~2.5 nm) as a lipid shell, poly(ethylene glycol) (PEG) as a stealth material, and the A10 RNA aptamer which binds to the PSMA antigen on the surface of prostate cancer cells as a model aptamer targeting ligand, targeted PLGA-Lecithin-PEG nanoparticles were developed. Particle size could be tuned within the range from 40 nm to 500 nm, accompanied with a surface zeta potential ranging from −80 mV to −30 mV. Using docetaxel (a widely used chemotherapeutics for cancers) as a model small molecule hydrophobic drug, the PLGA-Lecithin-PEG nanoparticle had drug encapsulation efficiency around 65% as contrast to 19% for the conventional PLGA-b-PEG diblock copolymer nanoparticle. In addition, less than 20% drugs were released from the NP during the first 6 hours, which holds broad promise for clinical applications. Both in vitro and in vivo results demonstrated that the attached RNA aptamer effectively targeted PLGA-Lecithin-PEG NPs to prostate cancer cells which express PSMA antigen on their plasma membrane, such as LNCaP cells.

Example 4

Nanoparticle Preparation

Lipid-polymer hybrid nanoparticles (NPs) were prepared via self-assembly of PLGA (poly (D,L-lactic-co-glycolic acid); Lactel, Pelham, Ala.), lecithin (soybean, refined, molecular weight:—330 Da; Alfa Aesar, Ward Hill, Mass.), and DSPE-PEG (1,2-distearoyl-sn-glycero-3-phosphoethanolamine-N-carboxy (polyethylene glycol)2000); Avanti, Alabaster, Ala.) through a single-step nanoprecipitation method. Briefly, PLGA polymer was dissolved in acetonitrile with concentrations ranging from 1~5 mg/mL. Lecithin/DSPE-PEG (8.5/1.5, molar ratio) were dissolved in 4 wt % ethanol aqueous solution at desired concentrations and heated to 65° C. The resulting PLGA solution was then added into the preheated lipid solution dropwise under gentle stiffing. The mixed solution was vortexed vigorously for 3 minutes followed by gentle stiffing for 2 hours. The remaining organic solvent and free molecules were removed by washing the NP solution three times using an Amicon Ultra-4 centrifugal filter (Millipore, Billerica, Mass.) with a molecular weight cut-off of 10,000 Da. To prepare drug-encapsulated NPs, docetaxel (Sigma-Aldrich, St Louis, Mo.) with proper initial dosage was dissolved into the PLGA acetonitrile solution before the nanoprecipitation process. NP size (diameter, m) and surface charge (zeta potential, mV) were measured by Quasi-elastic laser light scattering with a ZetaPALS dynamic light scattering detector (15 mW laser, incident beam=676 nm; Brookhaven Instruments Corporation, Holtsville, N.Y.).

Example 5

Drug Loading and Release Study

To measure the drug loading yield and release profile of docetaxel (Dtxl) from each type of NPs from Example 4, 3 mL NP PBS solutions at a concentration of 5 mg/mL were split equally into 30 Slide-A-Lyzer MINI dialysis microtube with a molecular weight cut-off of 3,500 Da (Pierce, Rockford, Ill.). These microtubes were dialyzed in 4 L PBS buffer at 37° C. with gentle stirring. PBS buffer was changed periodically during the whole dialysis process. At each data point, NP solutions from three microtubes were collected separately and mixed with an equal volume of acetonitrile to dissolve the NPs. The resulting free Dtxl content in each microtube was assayed using an Agilent (Palo Alto, Calif.) 1100 HPLC equipped with a pentafluorophenyl column (Curosil-PFP, 250×4.6 mm, 5µ; Phenomenex, Torrance, Calif.). Dtxl absorbance was measured by a UV-vis detector at 227 nm and a retention time of 12 minutes in 1 mL/min 50/50 acetonitrile/water mobile phase.

Example 6

Nanoparticle In Vitro Stability

NPs from Example 4 were incubated with 10 wt % BSA (bovine serum albumin; Sigma-Aldrich, St Louis, Mo.) solution and 10 wt % human plasma/heparin (BioChemMed, Winchester, Va.) solutions respectively at 37° C. under gentle stiffing at a concentration of 1 mg/mL. At each time point, an aliquot of NP solutions was collected to measure NP size using Quasi-elastic laser light scattering. The measurements were performed in triplicate at room temperature.

Example 7

Fluorescence Microscopy

To visualize cellular uptake of aptamer-targeted lipid-polymer hybrid NPs from Example 4 using fluorescence microscopy, a hydrophobic fluorescent dye, NBD-cholesterol (22-(N-(7-nitrobenz-2-oxa-1,3-diazol-4-yl)amino)-23,24-bisnor-5-cholen-3β-ol; Invitrogen, Carlsbad, Calif.), was encapsulated inside the NPs. The fluorescence emission spectrum of NBD (Excitation/Emission=460 nm/534 nm) was detected in the green channel (490 nm/528 nm) of a Delta Vision RT Deconvolution Microscope. In the study, the prostate LNCaP and PC3 cell lines were grown in 8-well microscope chamber slides in RPMI-1640 and Ham's F-12K medium respectively, both supplemented with 100 units/ml aqueous penicillin G, 100 µg/mL streptomycin, and 10% FBS (fetal bovine serum) at concentrations to allow 70% confluence in 24 hours (i.e., 40,000 cells per cm$^2$). On the day of experiments, cells were washed with pre-warmed PBS buffer and incubated with pre-warmed fresh media for 30 minutes before adding NPs with a final concentration of ~250 µg/mL (n=4). Cells were incubated with the NPs for 2 hours at 37° C., washed two times with PBS (300 µL per well), fixed with 4% formaldehyde, and mounted with non-fluorescent mounting medium DAPI (Vector Laboratory, Inc. Burlingame, Calif.). The cells were then imaged using a Delta Vision RT Deconvolution Microscope.

Figure 3A:
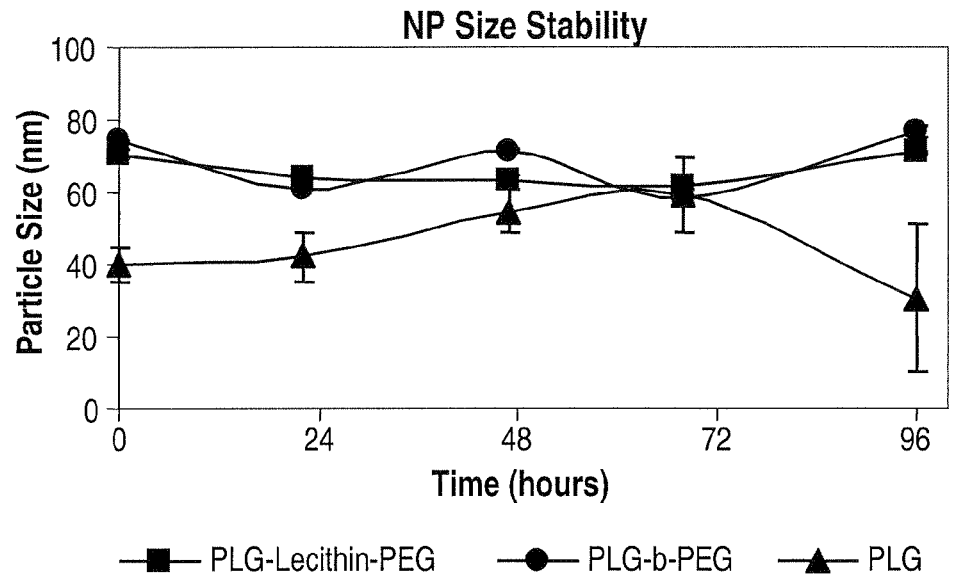
FIGS. 3A and 3B demonstrate size and zeta-potential stabilities of the amphiphilic layer-protected polymeric nanoparticles of the invention, respectively.
Figure 3B:
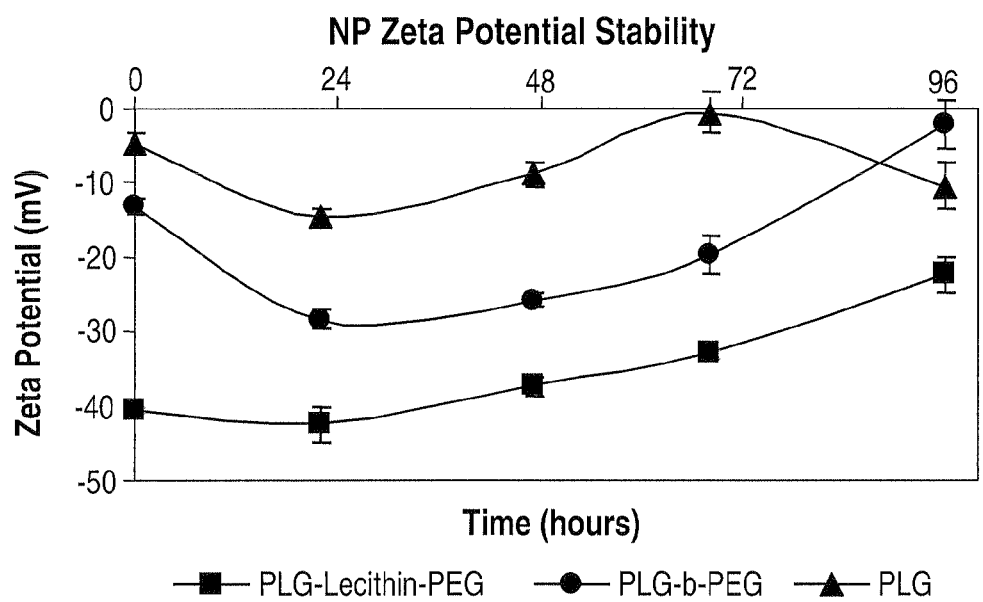

FIGS. 3A and 3B demonstrate size and zeta-potential stabilities of the amphiphilic layer-protected polymeric nanoparticles of the invention, respectively. [PLGA-Lecithin-PEG (squares), PLGA-b-PEG (circles), and pure PLGA (triangles)]

Figure 4:
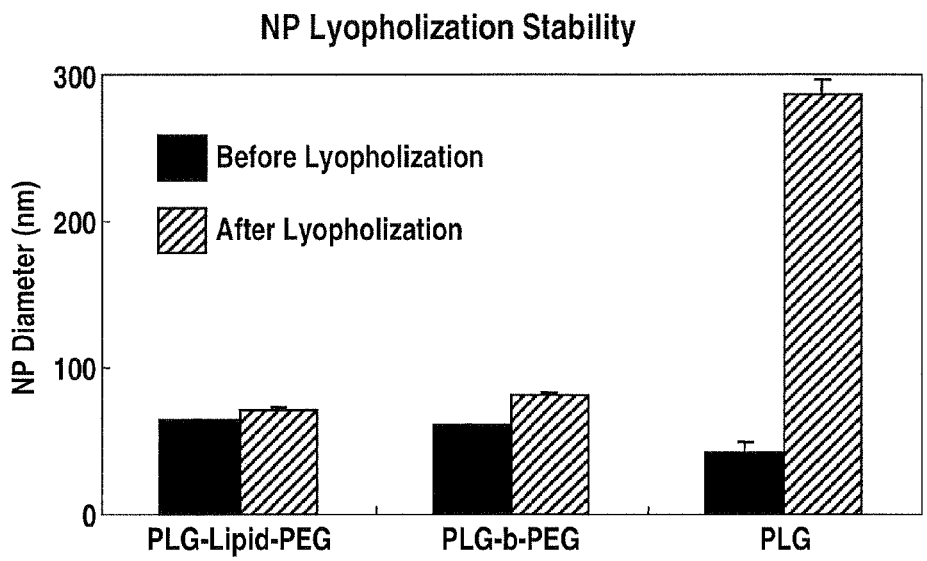
FIG. 4 demonstrates the size stability of the amphiphilic layer-protected polymeric nanoparticles of the invention after lypholization.

FIG. 4 demonstrates the size stability of the amphiphilic layer-protected polymeric nanoparticles of the invention after lypholization. [PLGA-Lecithin-PEG, PLGA-b-PEG, and pure PLGA. (Grey: before lypholization; Black: after lypholization)] All nanoparticles were lypholized after adding 10% sucrose. The nanoparticle powder was then dissolved into water again to test their size change before and after lypholization. Dynamic light scattering was used to measure nanoparticle size. The lipid-polymer hybrid nanoparticles were stable after lypholization.

Figure 5:
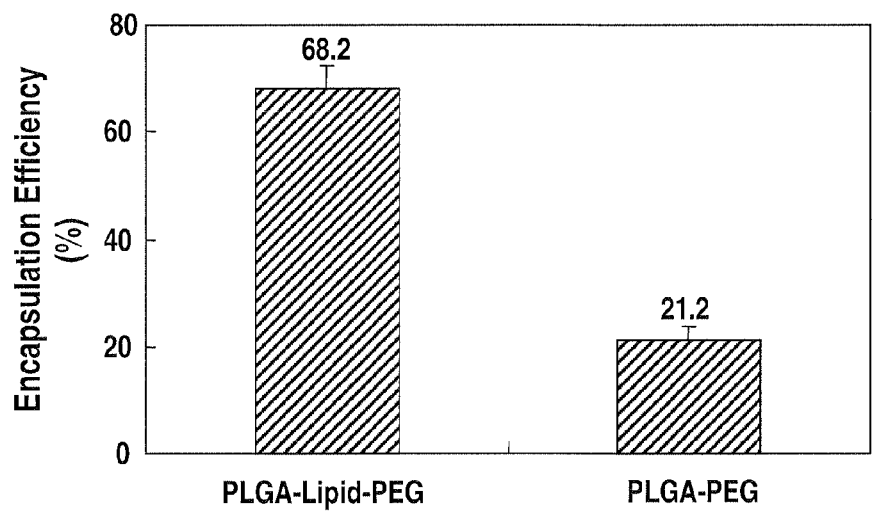
FIG. 5 demonstrates the high drug encapsulation efficiency of the amphiphilic layer-protected polymeric nanoparticles of the invention.

FIG. 5 demonstrates the high drug encapsulation efficiency of the amphiphilic layer-protected polymeric nanoparticles of the invention. By adding 10 wt % lipid to the interface of PLGA and PEG, the lipid-polymer NP has a drug encapsulation efficiency improved by approximately 300%.

Figure 6:
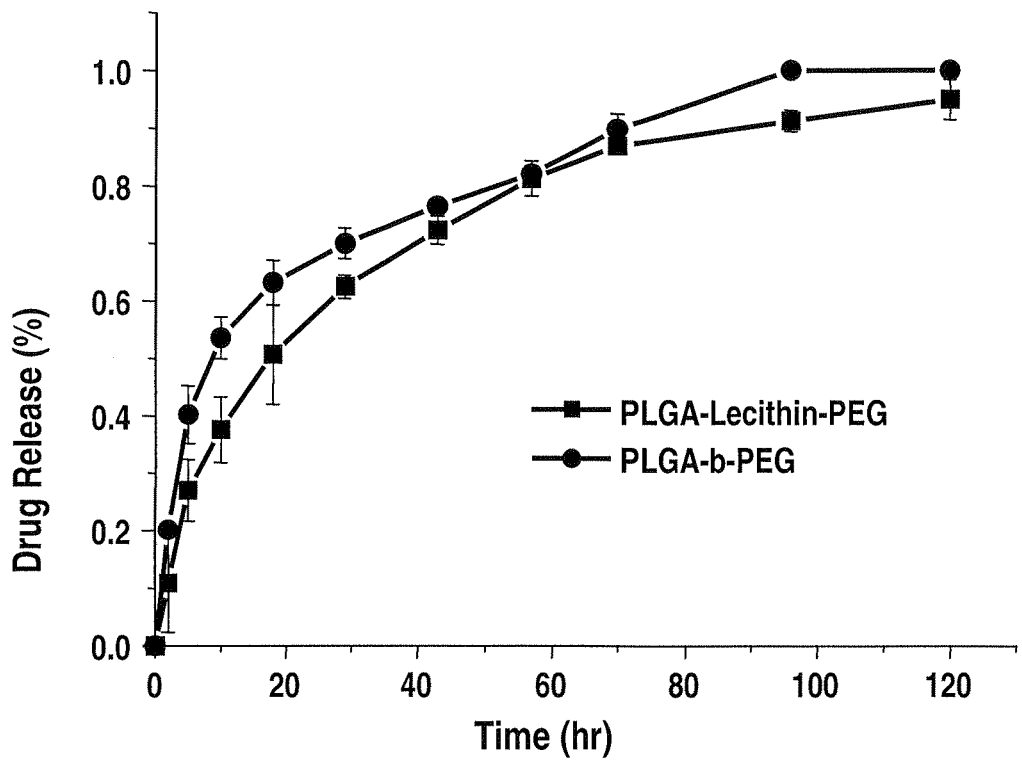
FIG. 6 demonstrates the improved drug release profile of the amphiphilic layer-protected polymeric nanoparticles of the invention.

FIG. 6 demonstrates the improved drug release profile of the amphiphilic layer-protected polymeric nanoparticles of the invention. [50% drug release time of liposome, PLGA-PEG NP and PLGA-Lipid-PEG NP is: 0.5 hr, 10 hr, and 20 hr respectively.]

Figure 7:
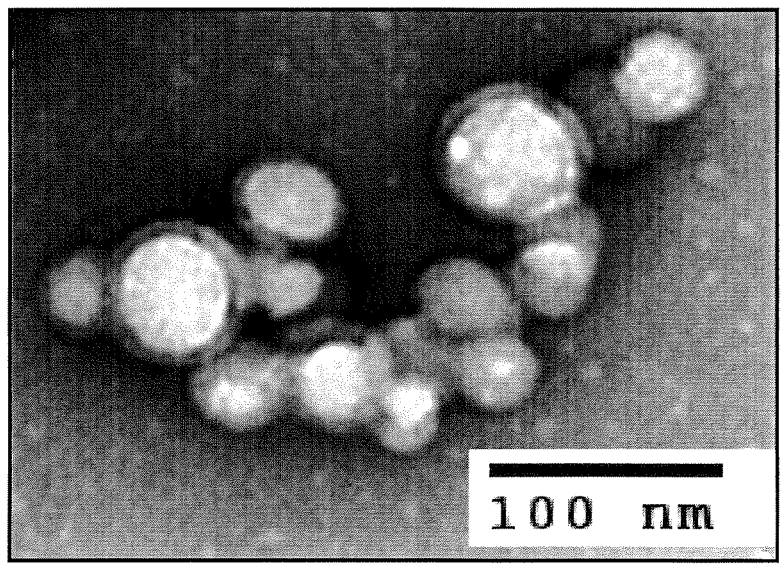
FIG. 7 shows an electron microscope image of the amphiphilic layer-protected polymeric nanoparticles of the invention.

FIG. 7 shows an electron microscope image of the amphiphilic layer-protected polymeric nanoparticles of the invention. [TEM images of the NPs with negative staining (uranyl acetate)]

Figure 8:
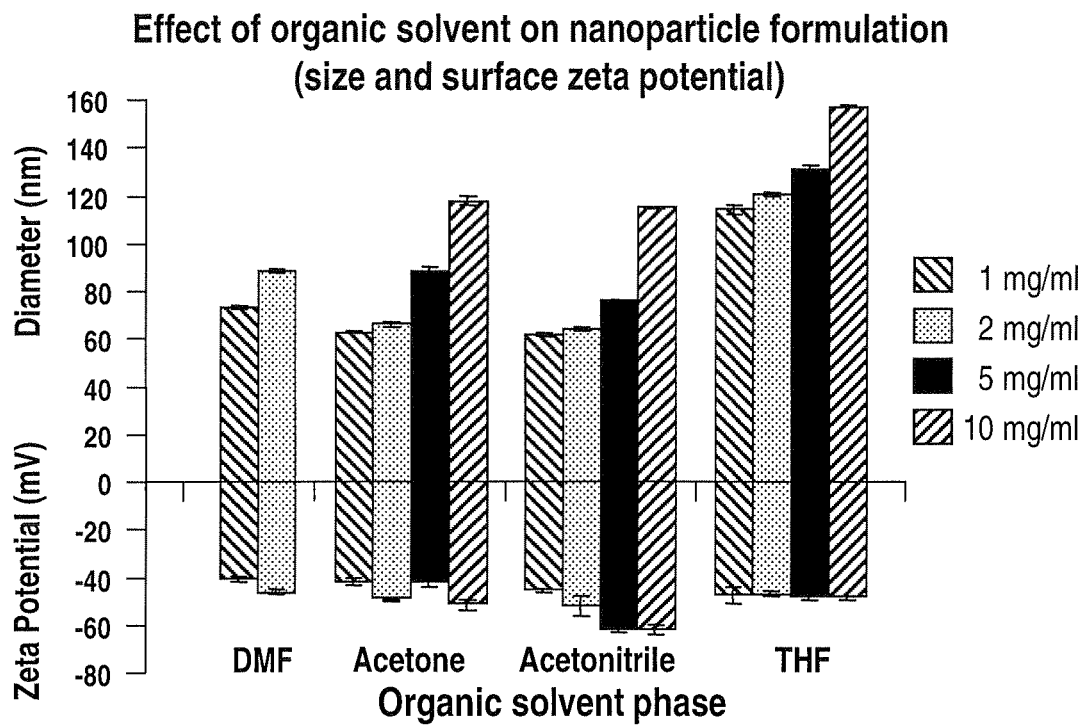
FIG. 8 demonstrates the effect of the use of various organic solvents on size and surface zeta potential in the preparation of the amphiphilic layer-protected polymeric nanoparticles of the invention.

FIG. 8 demonstrates the effect of the use of various organic solvents on size and surface zeta potential in the preparation of the amphiphilic layer-protected polymeric nanoparticles of the invention. The more polar the solvent is, the smaller the nanoparticle is formed after precipiation. But nanoparticle surface zeta potential is not considerably affected by solvent polarity.

Figure 9:
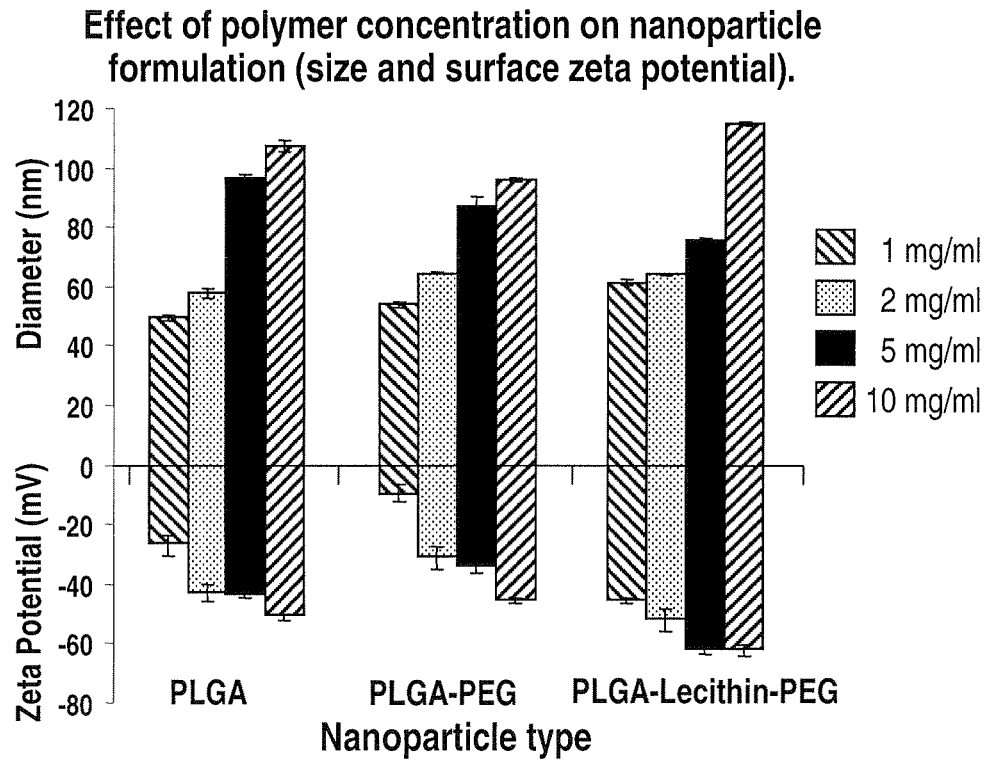
FIG. 9 demonstrates the effect of polymer concentration on size and surface zeta potential on the amphiphilic layer-protected polymeric nanoparticles of the invention.

FIG. 9 demonstrates the effect of polymer concentration on size and surface zeta potential on the amphiphilic layer-protected polymeric nanoparticles of the invention. When polymer concentration is higher than certain range, for example ~5 mg/mL, higher polymer concentration gives larger nanoparticle size, but doesn't dramatically affect nanoparticle surface zeta potential.

Figure 10:
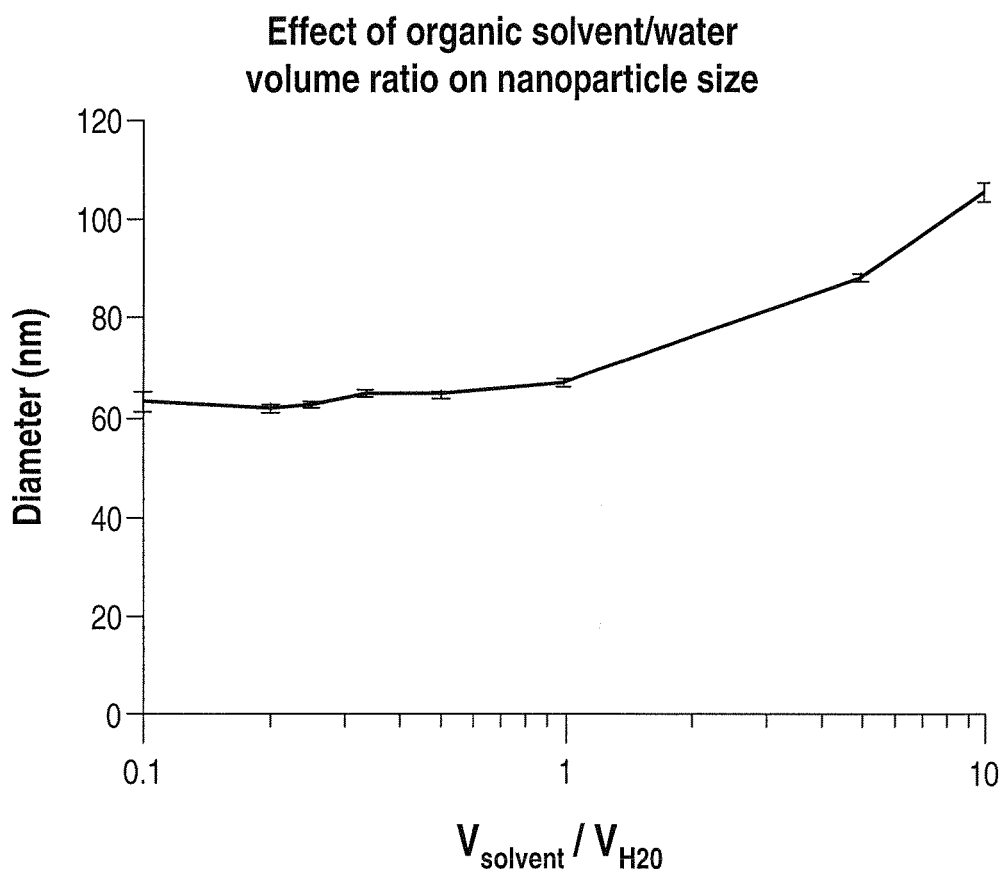
FIG. 10 demonstrates the effects of the ratio of organic solvent to water on the size of the amphiphilic layer-protected polymeric nanoparticles of the invention.

FIG. 10 demonstrates the effects of the ratio of organic solvent to water on the size of the amphiphilic layer-protected polymeric nanoparticles of the invention. Nanoparticle size becomes bigger when the volume ration of solvent to water is larger than 1.

Figure 11:
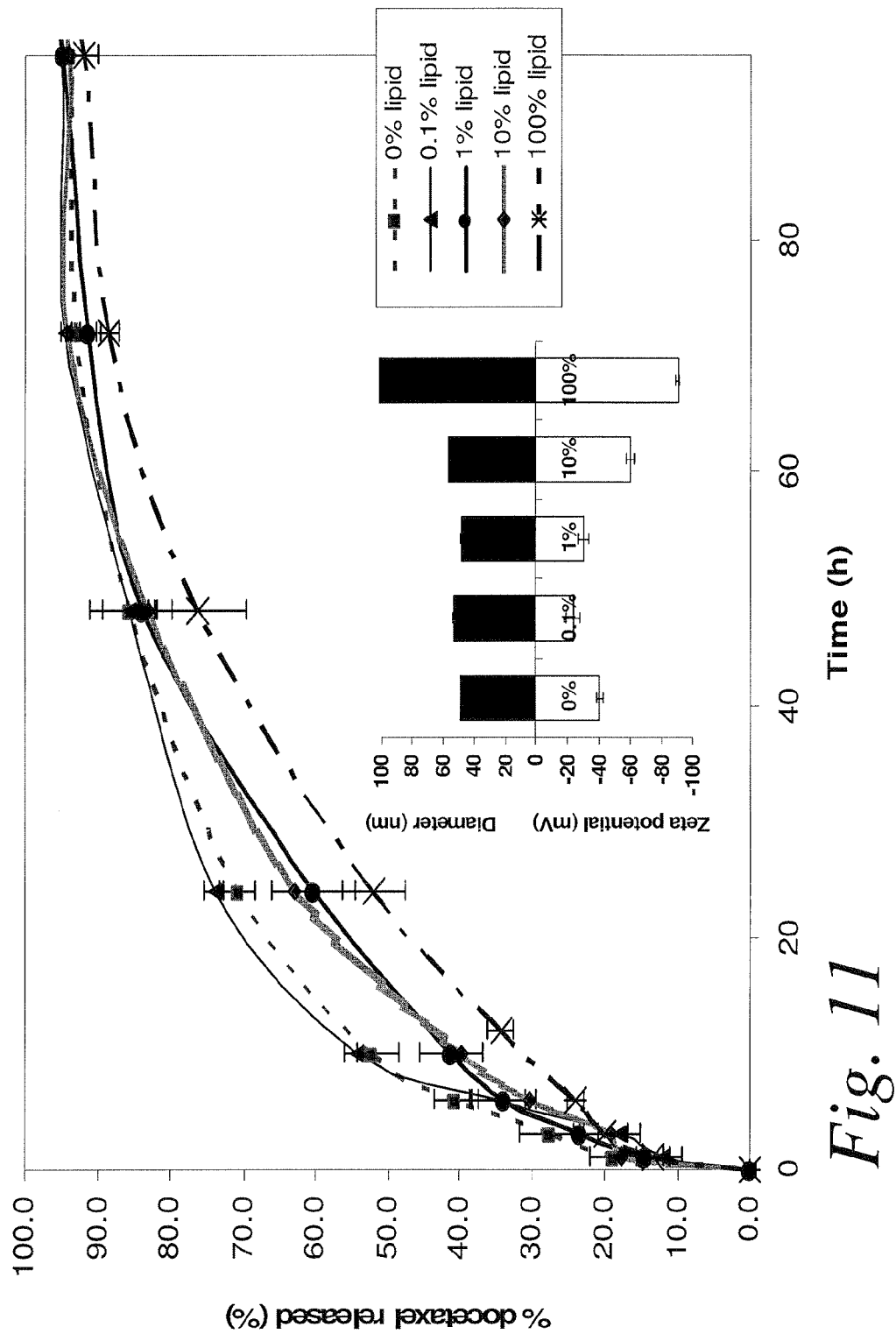
FIG. 11 demonstrates the effects of the ratio of lipid to polymer weight ratio on the therapeutic agent release rate of the amphiphilic layer-protected polymeric nanoparticles of the invention.

FIG. 11 demonstrates the effects of the ratio of lipid to polymer weight ratio on the therapeutic agent release rate of the amphiphilic layer-protected polymeric nanoparticles of the invention. Overall, higher lipid/polymer weight ratio results in slower drug release.

FIG. 12 demonstrates the effects of the ratio of lipid to polymer weight ratio on size and surface zeta potential on the amphiphilic layer-protected polymeric nanoparticles of the invention. With the increase of lipid/polymer weight ratio, nanoparticle size generally increases but surface zeta potential decreases.

Figure 13A:
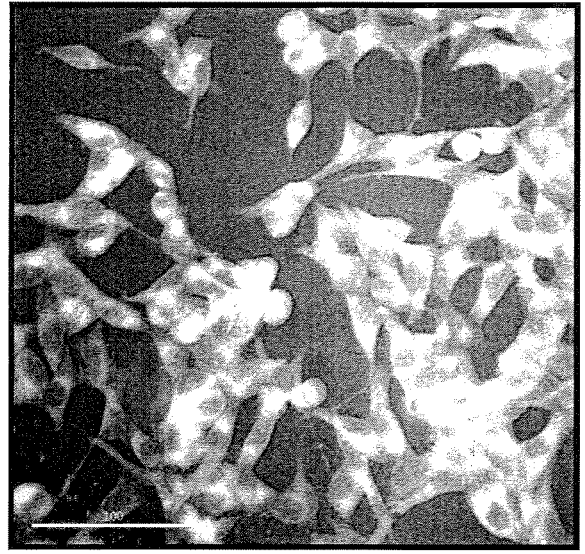
FIGS. 13A and 13B demonstrate the cellular uptake of the amphiphilic layer-protected polymeric nanoparticles of the invention.
Figure 13B:
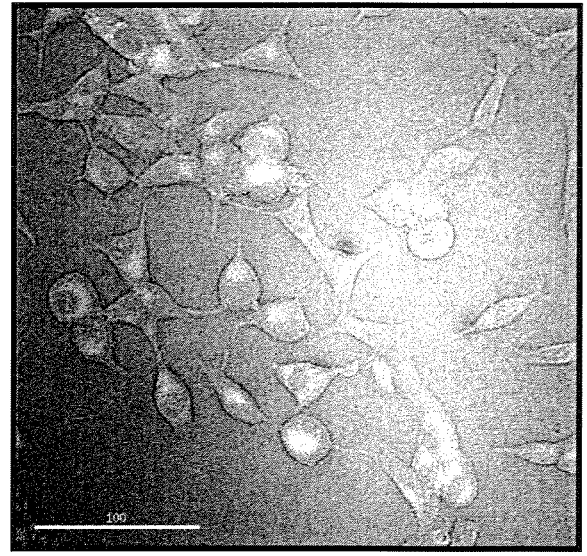

FIGS. 13A and 13B demonstrate the cellular uptake of the amphiphilic layer-protected polymeric nanoparticles of the invention.

Encapsulation efficiency is determined by taking a known amount of DNA, encapsulating it into a nanoparticle, removing any unencapsulated DNA by filtration, lysing the nanoparticle, then detecting the amount of DNA that was encapsulated by measuring its absorbance of light at 260 nm. The encapsulation efficiency is calculated by taking the amount of DNA that was encapsulated, then dividing it by the original amount of DNA. Stated alternatively, it is the fraction of initial DNA that is successfully encapsulated.

Zeta potential is determined by Quasi-elastic laser light scattering with a ZetaPALS dynamic light scattering detector (Brookhaven Instruments Corporation, Holtsville, N.Y.; 15 mW laser, incident beam=676 nm).

Figures 14A, 14B:
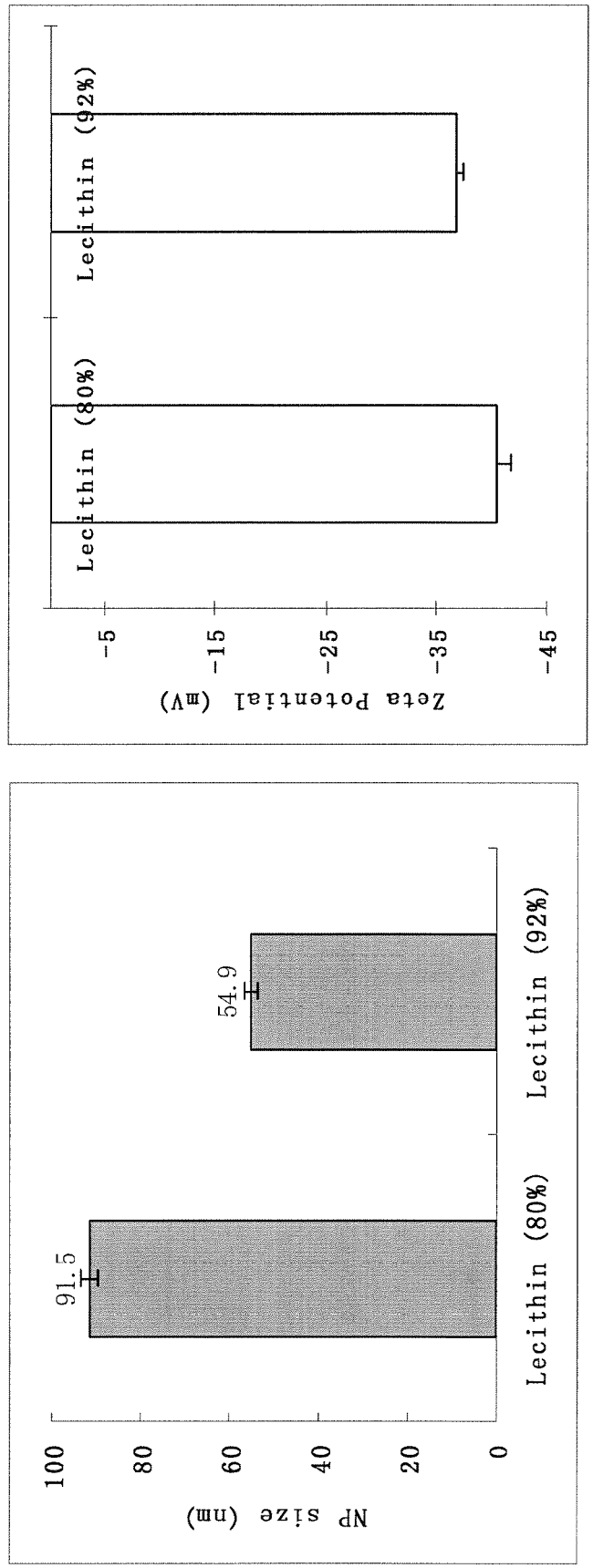
FIGS. 14A and 14B demonstrates a lecithin purity effect on PLGA-Lipid-PEG nanoparticle size and zeta potential.

FIGS. 14A and 14B demonstrate a lecithin purity effect on PLGA-Lipid-PEG nanoparticle size and zeta potential.

Figure 16:
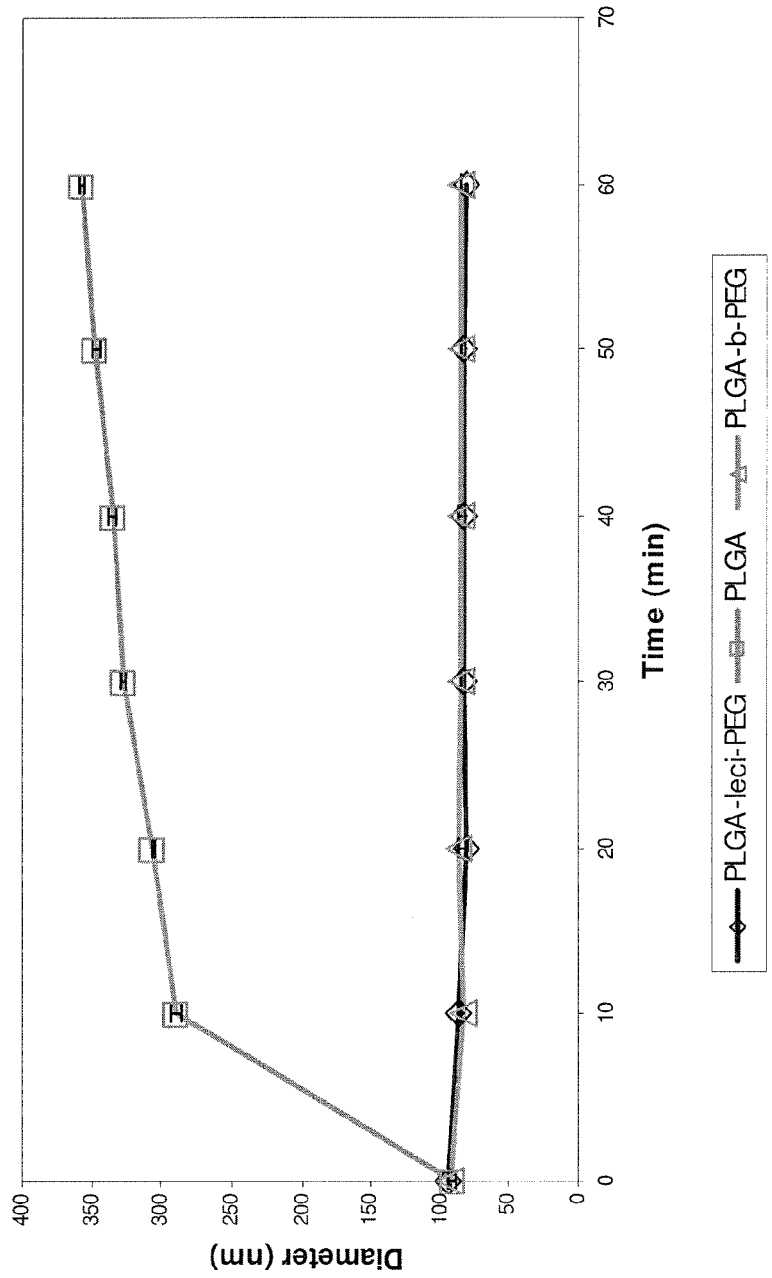
FIG. 16 demonstrates the stability of PLGA-Lipid-PEG, PLGA-PEG and PLGA nanoparticles in 10% BSA solution, respectively.

FIGS. 15A and 15B demonstrate a PLGA polymer concentration effect on nanoparticle size and zeta potential, respectively FIG. 16 demonstrates the stability of PLGA-Lipid-PEG, PLGA-PEG and PLGA nanoparticles in 10% BSA solution, respectively.

Figure 17:
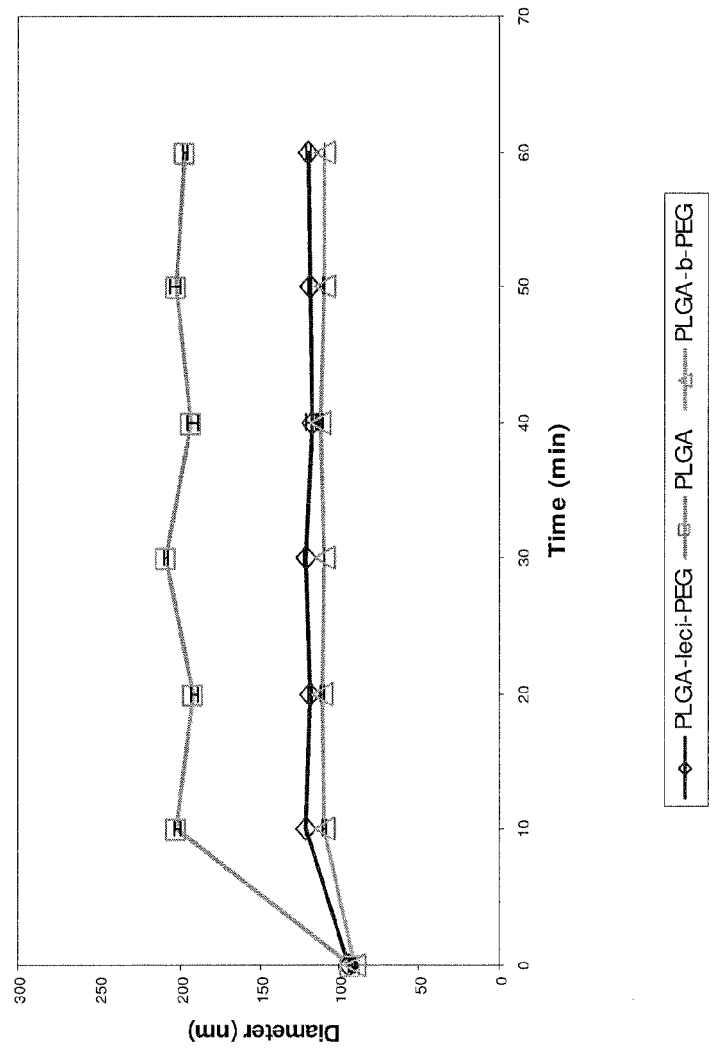
FIG. 17 demonstrates the stability of PLGA-Lipid-PEG, PLGA-PEG and PLGA nanoparticles in 10% plasma solution with heparin, respectively.

FIG. 17 demonstrates the stability of PLGA-Lipid-PEG, PLGA-PEG and PLGA nanoparticles in 10% plasma solution with heparin, respectively.

Figure 18:
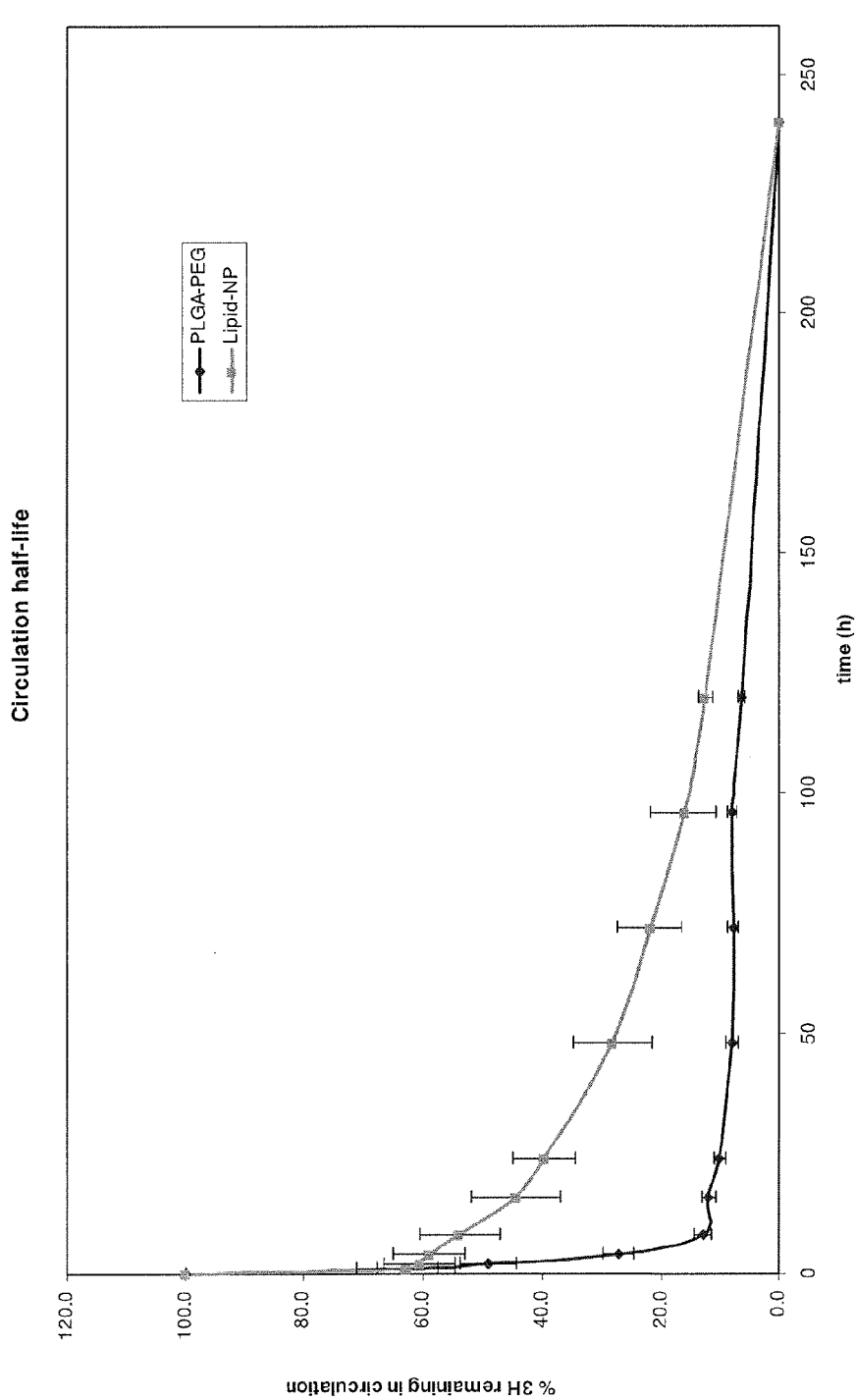
FIG. 18 demonstrates the in vivo circulation profile of PLGA-Lipid-PEG NP and PLGA-PEG NP. The circulation half-life of the particles is about 20 hr and 3 hr respectively.

FIG. 18 demonstrates the in vivo circulation profile of PLGA-Lipid-PEG NP and PLGA-PEG NP. The circulation half-life of the particles is about 20 hr and 3 hr respectively.

Example 8

Amphiphilic Protected Nanoparticle Characteristics

Estimated polymer weight per lipid-polymer hybrid nanoparticle at different size with an assumption that PLGA density is 1.2 g/cm$^3$

| | Polymer weight per NP | | |
|---|---|---|---|
| NP size (nm) | NP volume (nm$^3$) | PLGA density (g/cm$^3$) | Polymer weight per NP (g) |
| 40 | 33493.33333 | 1.2 | 4.0192E−17 |
| 50 | 65416.66667 | 1.2 | 7.85E−17 |
| 60 | 113040 | 1.2 | 1.35648E−16 |
| 70 | 179503.3333 | 1.2 | 2.15404E−16 |
| 80 | 267946.6667 | 1.2 | 3.21536E−16 |
| 90 | 381510 | 1.2 | 4.57812E−16 |

Estimated lipid weight per lipid-polymer hybrid nanoparticle at different size with an assumption that each lipid head group occupies an area of 0.5 nm$^2$.

| | Lipid weight per NP | | | |
|---|---|---|---|---|
| NP size (nm) | NP surface area (nm$^2$) | Amount of lipid per NP | Lipid Mw - Lecithin (g/mol) | Lipid weight per NP (g) |
| 40 | 5024 | 10048 | 758 | 1.22253E−17 |
| 50 | 7850 | 15700 | 758 | 1.91021E−17 |
| 60 | 11304 | 22608 | 758 | 2.7507E−17 |
| 70 | 15386 | 30772 | 758 | 3.74401E−17 |
| 80 | 20096 | 40192 | 758 | 4.89013E−17 |
| 90 | 25434 | 50868 | 758 | 6.18908E−17 |

Calculated lipid/polymer weight ratio of each lipid-polymer hybrid nanoparticle at different size:

| | Lipid/Polymer weight ratio at different lipid length & different NP size (%) | | | |
|---|---|---|---|---|
| NP size (nm) | Lipid Mw = 702 | Lipid Mw = 758 | Lipid Mw = 814 | Lipid Mw = 870 |
| 40 | 28.17014446 | 30.41733547 | 32.66452648 | 34.9117175 |
| 50 | 22.53611557 | 24.33386838 | 26.13162119 | 27.929374 |
| 60 | 18.78009631 | 20.27822365 | 21.77635099 | 23.27447833 |
| 70 | 16.09722541 | 17.38133456 | 18.66544371 | 19.94955285 |
| 80 | 14.08507223 | 15.20866774 | 16.33226324 | 17.45585875 |
| 90 | 12.52006421 | 13.51881577 | 14.51756733 | 15.51631889 |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A nanoparticle comprising:
a first covalent conjugate having the following formula: lipid—hydrophilic polymer—targeting moiety;
a second covalent conjugate having the following formula: lipid—hydrophilic polymer;
wherein the hydrophilic polymer of the first and second conjugates is a poly(ethylene glycol) polymer;
a hydrophobic core comprising a polyester and an agent selected from the group consisting of a therapeutic agent, a diagnostic agent, and a prophylactic agent;
an amphiphilic layer around the hydrophobic core, the layer comprising at least three amphiphilic components, wherein a first amphiphilic component of the layer is a phospholipid, and
wherein a second amphiphilic component and a third amphiphilic component of the layer are the lipid portions of the first and second covalent conjugates;
a hydrophilic outer layer comprising the hydrophilic polymer—targeting moiety portion of the first covalent conjugate and the hydrophilic polymer portion of the second covalent conjugate;
wherein the weight ratio of the amphiphilic components of the amphiphilic layer to the polyester is about 0.05 to 0.34; and
wherein the diameter of the nanoparticle is between about 40 and 500 nanometers.

2. The nanoparticle of claim 1, wherein the thickness of the amphiphilic layer is about 1 to about 5 nanometers.

3. The nanoparticle of claim 1, wherein the thickness of the amphiphilic layer is about 2.5 nanometers.

4. The nanoparticle of claim 1, wherein the lipid of the first covalent conjugate is selected from the group consisting of a phosphatidylcholine, a phosphatidylinositol, a phosphatidylethanolamine, and a phosphatidic acid.

5. The nanoparticle of claim 1, wherein the lipid of the first covalent conjugate is 1,2-distearoyl-sn-glycero-3-phosphoethanolamine.

6. The nanoparticle of claim 1, wherein the lipid of the second covalent conjugate is selected from the group consisting of a phosphatidylcholine, a phosphatidylinositol, a phosphatidylethanolamine, and a phosphatidic acid.

7. The nanoparticle of claim 1, wherein the lipid of the second covalent conjugate is 1,2-distearoyl-sn-glycero-3-phosphoethanolamine.

8. The nanoparticle of claim 1, wherein the targeting moiety of the first covalent conjugate is selected from the group consisting of nucleic acid aptamers, growth factors, hormones, cytokines, interleukins, antibodies, integrins, fibronectin receptors, p-glycoprotein receptors, and peptides.

9. The nanoparticle of claim 1, wherein the targeting moiety is a peptide having a length of fewer than 8 amino acids.

10. The nanoparticle of claim 1, wherein the targeting moiety comprises a peptide selected from the group consisting of AKERC (SEQ ID NO:1), CREKA (SEQ ID NO:2), ARYLQKLN (SEQ ID NO:3) and AXYLZZLN (SEQ ID NO:4); wherein X and Z are variable amino acids.

11. The nanoparticle of claim 1, wherein the targeting moiety is an aptamer.

12. The nanoparticle of claim 1, wherein the surface zeta potential of the nanoparticle is −80 mV to −30 mV.

13. The nanoparticle of claim 1, wherein the hydrophobic core comprises a therapeutic agent selected from the group consisting of a chemotherapeutic agent, an antineoplastic agent, and a cytostatic agent.

14. The nanoparticle of claim 1, wherein the hydrophobic core comprises a therapeutic agent selected from the group consisting of mitoxantrone and docetaxel.

15. The nanoparticle of claim 1, wherein the hydrophobic core comprises a therapeutic agent selected from the group consisting of vascular endothelial growth factor (VEGF), fibroblast growth factors, monocyte chemoattractant protein 1 (MCP-1), transforming growth factor alpha (TGF-alpha), transforming growth factor beta (TGF-beta), DEL-1, insulin like growth factors (IGF), placental growth factor (PLGF), hepatocyte growth factor (HGF), prostaglandin E1(PG-E1), prostaglandin E2(PG-E2), tumor necrosis factor alpha (TNF-alpha), granulocyte stimulating growth factor (G-CSF), granulocyte macrophage colony-stimulating growth factor (GM-CSF), angiogenin, follistatin, proliferin, PR39, PR11, nicotine, statins, niacin, bile acid resins, fibrates, and estradiol.

16. The nanoparticle of claim 1, wherein the polyester is poly(lactic-co-glycolic acid).

17. The nanoparticle of claim 1, wherein the first amphiphilic component is a lecithin.

18. A pharmaceutical composition comprising the nanoparticle of claim 1.

19. A pharmaceutical composition comprising the nanoparticle of claim 3.

* * * * *